United States Patent [19]

Hess et al.

[11] 4,152,527
[45] May 1, 1979

[54] 15-SUBSTITUTED-ω-PENTANORPROSTA-GLANDINS

[75] Inventors: Hans-Jürgen E. Hess; Thomas K. Schaaf, both of Old Lyme, Conn.

[73] Assignee: Pfizer Inc., New York, N.Y.

[21] Appl. No.: 428,673

[22] Filed: Dec. 27, 1973

Related U.S. Application Data

[63] Continuation-in-part of Ser. No. 304,750, Nov. 7, 1972, abandoned.

[51] Int. Cl.$^2$ .................................... C07C 177/00
[52] U.S. Cl. ................... 562/462; 260/308 D; 260/343.3 P; 260/346.22; 260/556 A; 260/556 AC; 260/557 B; 260/557 R; 260/559 R; 260/946; 424/269; 424/305; 424/308; 424/317; 424/320; 424/321; 424/324; 542/426; 542/428; 542/429; 560/53; 560/56; 560/116; 560/117; 560/118; 562/466; 562/498; 562/499; 562/500

[58] Field of Search .......... 260/240 R, 468 D, 514 D, 260/520, 345.8; 560/53, 56, 116, 117, 118; 562/462, 466, 498, 499, 500

[56] References Cited

U.S. PATENT DOCUMENTS

| 3,671,570 | 6/1972 | Bagli et al. | 260/514 D |
|---|---|---|---|
| 3,678,092 | 7/1972 | Finch | 260/520 |
| 3,746,728 | 7/1973 | Gordon et al. | 260/468 D |
| 3,751,463 | 8/1973 | Caton et al. | 260/240 R |
| 3,767,695 | 10/1973 | Pike et al. | 260/468 D |
| 3,798,275 | 3/1974 | Finch et al. | 260/468 D |

*Primary Examiner*—Robert Gerstl
*Attorney, Agent, or Firm*—Connolly and Hutz

[57] ABSTRACT

The 15-substituted-ω-pentanorprostaglandins and various intermediates employed in their preparation. The novel prostaglandins of this invention have been found to have activity profiles comparable to the parent prostaglandins, but exhibit a greater tissue specificity of action.

39 Claims, No Drawings

15-SUBSTITUTED-ω-PENTANORPROSTAGLANDINS

CROSS REFERENCE TO RELATED APPLICATIONS

This application is a continuation-in-part of our co-pending application Ser. No. 304,750, filed Nov. 7, 1972 now abandoned.

BACKGROUND OF THE INVENTION

This invention relates to certain novel analogs of the naturally occurring prostaglandins. In particular, it relates to novel 15-substituted-ω-pentanorprostaglandins and various novel intermediates useful in their preparation.

The prostaglandins are C-20 unsaturated fatty acids which exhibit diverse physiological effects. For instance, the prostaglandins of the E and A series are potent vasodilators (Bergstrom, et al., *Acta Physiol. Scand.* 64:332-33, 1965 and Bergstrom et al., *Life Sci.* 6:449-455, 1967) and lower systemic arterial blood pressure (vasodepression) on intravenous administration (Weeks and King, *Federation Proc.* 23:327, 1964; Bergstrom, et al., 1965, op. cit.; Carlson, et al., *Acta Med. Scand.* 183:423-430, 1968; and Carlson, et al., *Acta Physiol. Scand.* 75:161-169, 1969). Another well known physiological action for $PGE_1$ and $PGE_2$ is as a bronchodilator (Cuthbert, *Brit. Med. J.* 4:723-726, 1969).

Still another important physiological role for the natural prostaglandins is in connection with the reproductive cycle. $PGE_2$ is known to possess the ability to induce labor (Karim, et al., *J. Obstet. Gynaec. Brit. Cwlth.* 77:200-210, 1970), to induce therapeutic abortion (Bygdeman, et al., *Contraception,* 4, 293 (1971) and to be useful for control of fertility (Karim, *Contraception,* 3, 173 (1973)). Patents have been obtained for several prostaglandins of the E and F series as inducers of labor in mammals (Belgian Patent 754,158 and West Coast Patent 2,034,641), and on $PGF_1$, $F_2$, and $F_3$ for control of the reproductive cycle (South African Patent 69/6089). It has been shown that luteolysis can take place as a result of administration of $PGF_2\alpha$ [Labhsetwar, *Nature* 230,528 (1971)] and hence prostaglandins have utility for fertility control by a process in which smooth muscle stimulation is not necessary.

Still other known physiological activities for $PGE_1$ are in the inhibition of gastric acid secretion (Shaw and Ramwell, In: *Worcester, Symp. on Prostaglandins,* New York, Wiley, 1968, p. 55-64) and also of platelet aggregation (Emmons, et al., *Brit. Med. J.* 2:468-472, 1967).

It is now known that such physiological effects will be produced in vivo for only a short period, following the administration of a prostaglandin. A substantial body of evidence indicates that the reason for this rapid cessation of activity is that the natural prostaglandins are quickly and efficiently metabolically deactivated by β-oxidation of the carboxylic acid side-chain and by oxidation of the 15α-hydroxyl group (Anggard, et al., *Acta. Physiol. Scand.,* 81, 396 (1971) and references cited therein). It has been shown that placing a 15-alkyl group in the prostaglandins has the effect of increasing the duration of action possibly by preventing the oxidation of the C15-hydroxyl [Yankee and Bundy, JACS, 94, 3651 (1972)], Kirton and Forbes, *Prostaglandins,* 1, 319 (1972).

It was, of course, considered desirable to create analogs of the prostaglandins which would have physiological activities equivalent to the natural compounds, but in which the selectivity of action and the duration of the activity would be increased. Increased selectivity of action would be expected to alleviate the severe side effects, particularly gastrointestinal side effects, frequently observed following systemic administration of the natural prostaglandins (Lancet, 536, 1971).

SUMMARY OF THE INVENTION

The present invention comprises novel ω-pentanorprostaglandins of the formula:

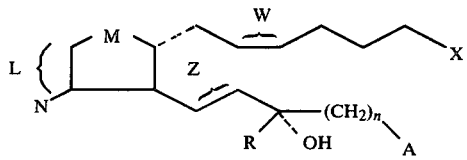

and the $C_{15}$ epimers;

wherein A is cycloalkyl from three to ten carbon atoms, 1-adamantyl, 2-norbornyl, 2-(1,2,3,4-tetrahydronaphthyl) wherein said group is racemic or optically active, 2-indanyl or substituted 2-indanyl wherein said substituent is halo, trifluoromethyl, lower alkyl or lower alkoxy;

R is hydrogen or lower alkyl;

n is an integer from 0 to 5;

W and L are each a single bond or cis double bond;

Z is single bond or trans double bond;

M is keto,

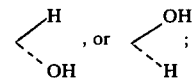

N is hydrogen or α-hydroxyl;

X is selected from:

a first sub-group comprising

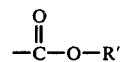

wherein R' is hydrogen, alkyl of from 1-10 carbon atoms; aralkyl of from 7 to 9 carbon atoms; cycloalkyl of from 3 to 8 carbon atoms; α- or β-naphthyl; phenyl, 5-indanyl; or monosubstituted phenyl, wherein said substituent is halo, lower alkyl, lower alkoxy or phenyl;

a second sub-group comprising 5-tetrazolyl; or a third sub-group comprising

wherein R" is alkanoyl having from 2-10 carbon atoms or cycloalkanoyl having from 4 to 8 carbon atoms; aryoyl or substituted aryoyl of from 7 to 11 carbon atoms wherein said substituent is methyl, halogen, or methoxy; alkylsulfonyl of from 1 to 7 carbon atoms; arylsulfonyl or substituted arylsulfonyl wherein said substituent is methyl, halogen, or methoxy;

and wherein L, M and N are so selected as to complete the structure of a prostaglandin of the A, E, or F series.

Preferred prostaglandins are as follows:

Compounds of formula 1 wherein said prostaglandins are of the E series, compounds of formula 1 wherein said prostaglandins are of the $F_\alpha$ series, compounds of formula 1 wherein said prostaglandins are of the $F_\beta$ series, compounds of formula 1 wherein said prostaglandins are of the A series, compounds of formula 1 wherein n is 0, compounds of formula 1 wherein n is 1, compounds of formula 1 wherein n is 2, compounds of formula 1 wherein n is 3, compounds of formula 1 wherein n is 4, compounds of formula 1 wherein n is 5, compounds of formula 1 wherein n is 0 and said prostaglandin is of the E series, compounds of formula 1 wherein n is 0 and said prostaglandin is of the F series, compounds of formula 1 wherein n is 1 and said prostaglandin is of the E series, compounds of formula 1 wherein n is 1 and said prostaglandin is of the F series, compounds of formula 1 wherein n is 2 and said prostaglandin is of the E series, compounds of formula 1 wherein n is 2 and said prostaglandin is of the F series, compounds of formula 1 wherein A is cycloalkyl of from 3 to 10 carbons, compounds of formula 1 wherein A is 2-norbornyl, compounds of formula 1 wherein A is 1-adamantyl, compounds of formula 1 wherein A is 2indanyl or substituted 2-indanyl wherein said substituent is halo, trifluoromethyl, lower alkyl or lower alkoxyl, compounds of formula 1 wherein A is 2-(5,6-dimethoxy indanyl), compounds of formula 1 wherein A is cyclohexyl, a compound of formula 1 wherein W is a cis double bond and Z is a trans double bond, a compound of formula 1 wherein W is a cis double bond and Z is a single bond, a compound of formula 1 wherein W is a single bond and Z is a trans double bond, a compound of formula 1 wherein W is a single bond and Z is a single bond, a compound of formula 1 wherein Ar is 2-indanyl, n is 0, and the prostaglandin is $PGE_2$; a compound of formula 1 wherein Ar is 2-indanyl, n is 0, and the prostaglandin is $PGF_{2\alpha}$, a compound of formula 1 wherein Ar is 2-(5,6-dimethoxy indanyl), n is 0, and the prostaglandin is $PGE_2$, a compound of formula 1 wherein Ar is 2-(5,6-dimethoxy indanyl), n is 0, and the prostaglandin is $PGF_{2\alpha}$, a compound of formula 1 wherein Ar is 1-adamantyl, n is 2, and the prostaglandin is $PGE_2$, and a compound of formula 1 wherein Ar is 1-adamantyl, n is 2, and the prostaglandin is $PGF_{2\alpha}$, a compound of formula 1 wherein Ar is 2-indanyl, n is 0, said prostaglandin is $PGF_{2\alpha}$, X is selected from the second subgroup, and R is hydrogen, a compound of formula 1 wherein Ar is 2-indanyl, n is 0, said prostaglandin is $PGF_{2\alpha}$, X is selected from the third subgroup, R" is methyl sulfonyl, and R is hydrogen, a compound of formula 1 wherein Ar is 2-indanyl, n is 0, said prostaglandin is $PGE_2$, X is selected from the second subgroup, and R is hydrogen, a compound of formula 1 wherein Ar is 2-indanyl, n is 0, said prostaglandin is $PGE_2$, R" is methyl sulfonyl and R is hydrogen, a compound of formula 1 wherein Ar is 2-(1,2,3,4-tetrahydronaphthyl), X is selected from the second subgroup, R is hydrogen, said prostaglandin is $PGF_{2\alpha}$ and n is zero, a compound of formula 1 wherein Ar is 2-(1,2,3,4-tetrahydronaphthyl), X is selected from the third subgroup, R" is methyl sulfonyl, n is zero, R is hydrogen, and said prostaglandin is $PGF_{2\alpha}$, a compound of formula 1 wherein Ar is cyclohexyl, n is one, X is selected from the first subgroup, R' and R are each hydrogen and said prostaglandin is $PGE_2$, a compound of formula 1 wherein X is selected from the first subgroup, 15-(2-indanyl)-ω-pentanorprostaglandin $E_2$, 15-(2-indanyl)-ω-pentanorprostaglandin $F_{2\alpha}$, 15-[2-(5,6-dimethoxy indanyl)]-ω-pentanorprostaglandin $E_2$, 15-[2-(5,6-dimethoxy indanyl)]-107-pentanorprostaglandin $F_{2\alpha}$, and 17-(1-adanantyl)-ω-trinorprostaglandin $F_{2\alpha}$.

Novel intermediates of the formula below are also a feature of this invention.

A compound of the structure:

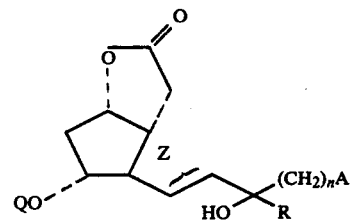

wherein R is hydrogen or lower alkyl; and Q is hydrogen or p-phenylbenzoyl;

a compound of the structure:

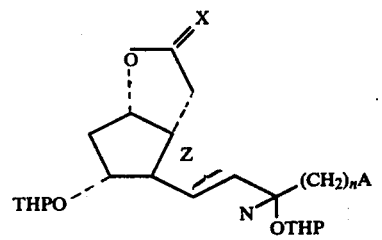

a compound of the structure:

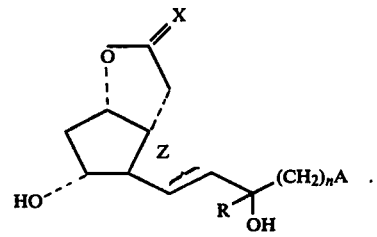

wherein THP is tetrahydropyranyl, n is an integer from 0 to 5; Z is a single bond or trans double bond and X is =O or

;

A compound of the structure:

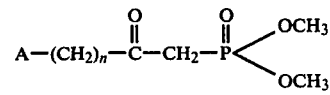

A compound of the structure:

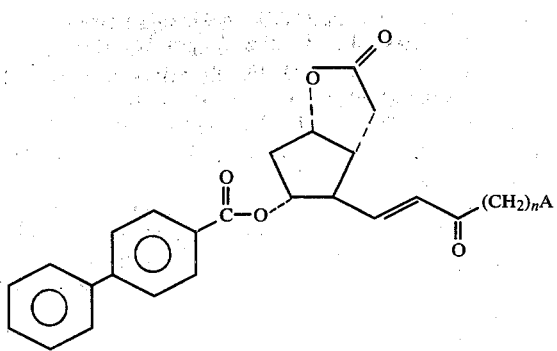

wherein A has the definition given above; and compounds of the structure:

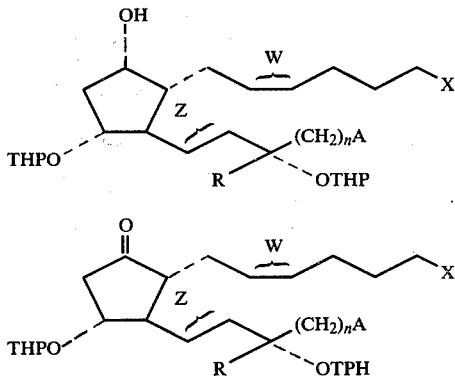

and the $C_9$ and $C_{15}$ epimers thereof;

wherein A is cycloalkyl from three to ten carbon atoms, 1-adamantyl, 2-norbornyl, 2-(1,2,3,4-tetrahydronaphthyl) wherein said groups is racemic or optically active, 2-indanyl or substituted 2-indanyl wherein said substituent is halo, trifluoromethyl, lower alkyl or lower alkoxy;

R is hydrogen or lower alkyl;
THP is 2-tetrahydropyranyl;
n is an integer from 0 to 5;
W is a single bond or cis double bond;
Z is a single bond or trans double bond; and
X is selected from:
a first sub-group comprising

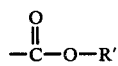

wherein R' is alkyl of from 1-10 carbon atoms; aralkyl of from 7 to 9 carbon atoms; cycloalkyl of from 3 to 8 carbon atoms; α- or β-naphthyl; phenyl or monosubstituted phenyl, wherein said substituent is halo, lower alkyl, lower alkoxy or phenyl;

a second sub-group comprising tetrazolyl; or
a third sub-group comprising

wherein R" is alkanoyl having from 2-10 carbon atoms; or cycloalkanoyl having from 4 to 8 carbon atoms; aryoyl or substituted aryoyl of from 7 to 11 carbon atoms wherein said substituent is methyl, halogen, or methoxy; alkylsulfonyl of from 1 to 7 carbon atoms; arylsulfonyl or substituted arylsulfonyl wherein said substituent is methyl, halogen, or methoxy.

It will be understood by those skilled in the art that in structures depicting hemiacetals, no sterochemistry is implied at the lactol carbon.

It will be further understood that as herein used, the expression "prostaglandin of the 'zero' series," for example $PGE_0$, refers to prostaglandin in which the 5–6 and 13–14 double bonds have been saturated, i.e.: $PGE_0$ is 5,6-13,14 - tetrahydro $PGE_2$. In addition, the phrases "one series" or "two series" as herein employed refer to the degree of unsaturation in the side chains, e.g., $PGE_2$, $PGA_2$, and $PGF_{2\beta}$, are prostaglandins of the "two series" whereas $PGE_1$, $PGF_1$ and $PGA_1$ are prostaglandins of the "one series". As used herein and in the claims, the term prostaglandin is understood to embrace both epimers at $C_{15}$. Furthermore as herein employed the phrase lower "alkyl group" refers to alkyl groups containing from 1 to 4 carbon atoms.

DETAILED DESCRIPTION OF THE INVENTION

The starting material for the various novel compounds of this invention are available commercially or are made by methods well known to those skilled in the art. For example, to make dimethyl 2-oxo-2-(2-indanyl-)ethylphosphonate, the starting material for the synthesis of the 15-(2-indanyl) prostaglandins, one cools a solution of dimethyl methylphosphonate in tetrahydrofuran to −78° in a dry nitrogen atmosphere and then adds n-butyllithium in hexane dropwise, slowly. After stirring, ethyl indane-2-carboxylate is added dropwise. After 3 to 4 hours at −78° the reaction mixture is warmed to ambient temperature, neutralized with acetic acid and rotary evaporated to a white gel. The gelatinous material is taken up in water, the aqueous phase is extracted in chloroform and the combined organic extracts are backwashed, dried, and concentrated to give the desired product.

To make the desired 15-substituted-ω-pentanorprostaglandins, one converts the appropriate acids as described below to esters by the usual methods and thence into phosphonates as described above for the 15-(2-indanyl) starting compound.

To make the 16-cyclohexyl prostaglandins, cyclohexylacetic acid is purchased from Aldrich Chem. Co. (No. C10,450-F), converted to the ester and thence to the phosphonate as for the 15-(2-indanyl) compound.

To prepare the 20-cyclopentyl prostaglandins, one requires 6-cyclopentylhexanoic acid which is prepared by the method of Goryaeu, et al., *Tr. Inst. Khim. Nauk, Akad, Nauk. Kee. SSR*, 19, 77(1967); C.A., 69, 18646 Z (1968) and converted to the ester by standard means and thence to the phosphonate by the method described for the 15-(2-indanyl) compound.

To prepare the 15-(2-(+)-(1,2,3,4-tetrahydronaphthyl)) prostaglandins, (+)-2-(1,2,3,4-tetrahydronaphthyl) carboxylic acid is prepared by the method of Cohen, et. al., *J. Biol. Chem.*, 10, 2664 (1969), converted to the ester and thence to the phosphonate as described for the 15-(2-indanyl) case.

To prepare the 15-(2-)(−)-(1,2,3,4-tetrahydronaphthyl)) prostaglandins, (−)-2-(1,2,3,4-tetrahydronaphthyl) carboxylic acid is prepared by the method of Cohen, et. al., *J. Biol. Chem.*, 10, 2664 (1969), converted to the ester and thence to the phosphonate as described for the 15-(2-indanyl) compound.

When 15-(2-indanyl prostaglandins are desired, one makes indane-2-carboxylic acid by, for example, the method of Bergman and Hoffman, *J. Org. Chem.*, 26, 3555 (1961), converts it to the ester and thence to the phosphonate as described above.

To make 16-(2-indanyl) prostaglandins, one prepares 2-indanylacetic acid as described by Bergman and Hoffman, *J. Org. Chem.*, 26, 3555 (1961), converts it to the ester and thence to the phosphonate as described for the 15-(2-indanyl) case.

To make 15-(2-(5,6-dimethoxyindanyl) prostaglandins, one must prepare the requisite 5,6-dimethoxyindane-2-carboxylic acid. Condensation of 4,5-bischloromethylveratrole (prepared as described by Wood, Perry, and Tung, *J. Am. Chem. Soc.*, 72, 2989 (1950)) with ethyl t-butylmalinate in the presence of sodium hydride provides the 2-carboethoxy-2-carbo-t-butoxy-5,6-dimethoxyindane. Treatment of this diester with p-toluenesulfonic acid in refluxing benzene followed by decarboxylative distillation of the product affords ethyl 5,6-dimethoxyindane-2-carboxylate which is converted into the phosphonate as described for the 15-(2-indanyl) compound.

To prepare the 19-cyclopropyl prostaglandins, 5-cyclopropylvaleric acid is prepared by the method of Turnbull and Wallis, *J. Org. Chem.* 21, 663 (1956) and converted to the ester and thence to the phosphonate by the method described for the 15-(2-indanyl) compound.

To prepare the 15-cyclodecyl prostaglandins, cyclodecanecarboxylic acid is prepared by the method of Marshall and Scanio, *J. Org. Chem.*, 30, 3019 (1965), converted to the ester and thence to the phosphonate as described for the 15-(2-indanyl) case.

To prepare the 16-(1-adamantyl) prostaglandins, (1-adamantyl) acetic acid is purchased from Aldrich Chem. Co. (No. 12, 727-2), converted to the ester and thence to the phosphonate as for the 15-(2-indanyl) compound.

To prepare the 17-(1-adamantyl) prostaglandins, 3-(1-adamantyl) propionic acid is prepared by the method of Fieser, et. al., *J. Med. Chem.*, 10, 517 (1967), converted to the ester and thence to the phosphonate as described for the 15-(2-indanyl) case.

When 16-(2-norbornyl) prostaglandins are desired, one purchases 2-norbornylacetic acid from Aldrich Chem. Co. (No. 12, 726-4), converts it to the ester and thence to the phosphonate as for the 15-(2-indanyl) compound.

To prepare the 15-(2-(±)-(1,2,3,4-tetrahydronaphthyl)) prostaglandins, (±)-2-(1,2,3,4-tetrahydronaphthyl) carboxylic acid is prepared by the method of Cohen, et. al., *J. Biol. Chem.*, 10, 2664 (1969), converted to the ester and thence to the phosphonate as described for the 15-(2-indanyl) case.

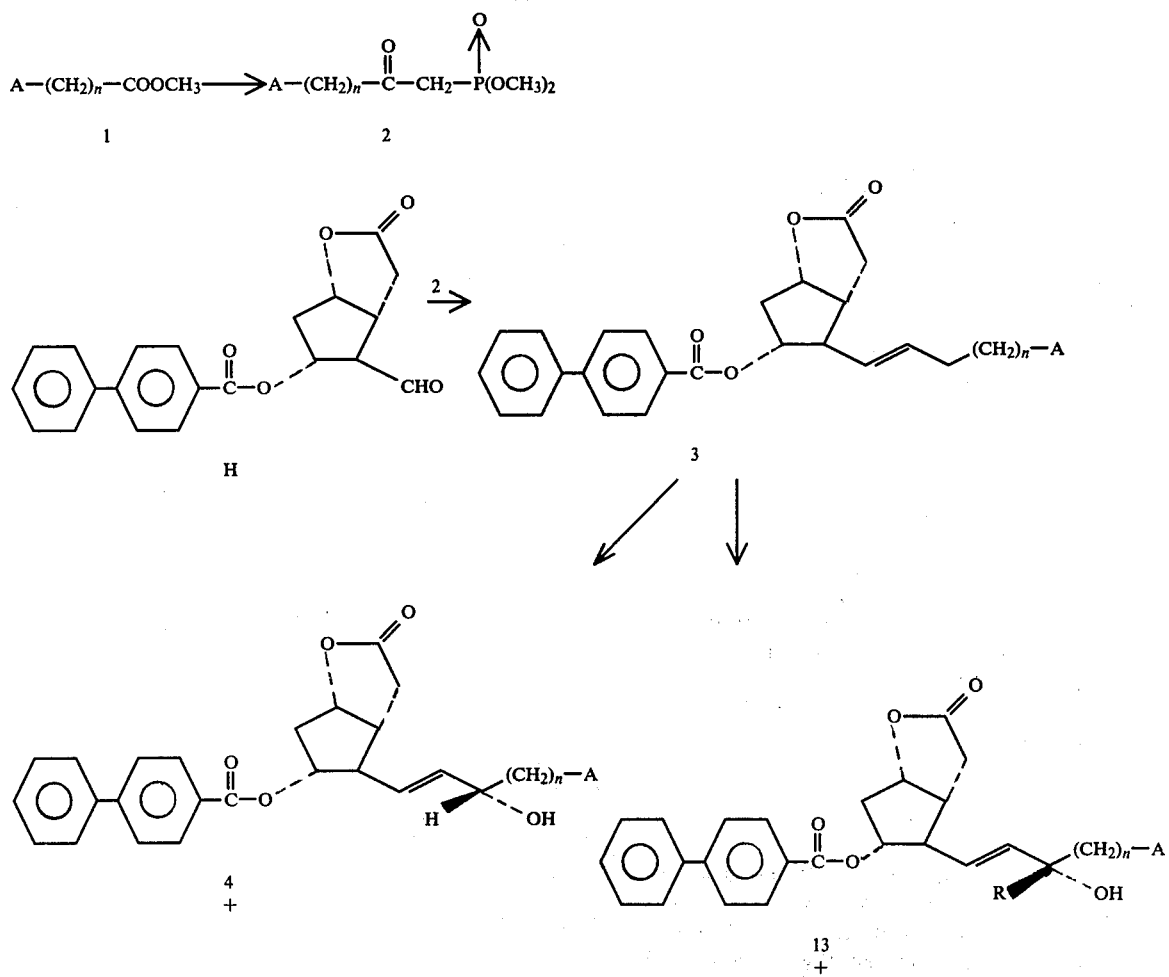

-continued

Scheme A

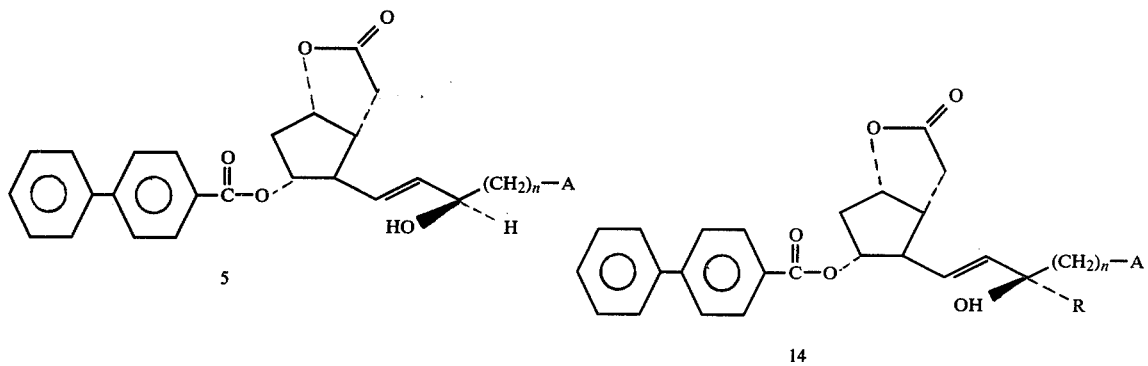

As shown in scheme A, the first step (1 →2) is the condensation of the appropriate ester with a dialkyl methylphosphonate to produce ketophosphonate 2. Typically, the desired methyl ester is condensed with dimethyl methyl phosphonate.

In 2 →3 the ketophosphonate 2 is caused to react with the known [Corey, et al., J. Am. Chem. Soc., 93, 1491 (1971)] aldehyde H to produce, after chromatography or crystallization, the enone 3. The compound in which the p-biphenyl carbonyl group is replaced with a p-biphenyl carbamoyl protecting group is also useful as a substitute for H and has the added benefit that is the reduction step (3 →4) a higher percentage of the desired α isomer is produced.

The enone 3 can be converted to a mixture of tertiary alcohols 13 and 14 by reaction with the appropriate metallo alkyl and the isomeric 13 and 14 can be separated by column chromatography. The enone 3 can be reduced with zinc borohydride or with lithium trialkyl-borohydrides, such as lithium triethylborohydride, to a mixture of alcohols, 4 and 5 which can be separated as above. In this reaction ethers such as tetrahydrofuran or 1,2-dimethoxyethane are usually employed as solvents, although occasionally methanol is preferred to ensure specificity of reduction. Further transformations of 4 are shown on scheme B.

4 →6 is a base catalyzed transesterification in which the p-biphenyl-carbonyl protecting group is removed. This is most conveniently conducted with potassium carbonate in methanol or methanol-tetrahydrofuran solvent. 6 → 7 involves the protection of the two free hydroxyl groups with an acid-labile protecting group. Any sufficiently acid-labile grou is satisfactory; however, the most usual one is tetrahydropyranyl, which can be incorporated in the molecule by treatment with dihydropyran and an acid catalyst in an anhydrous medium. The catalyst is usually p-toluenesulfonic acid.

Scheme B

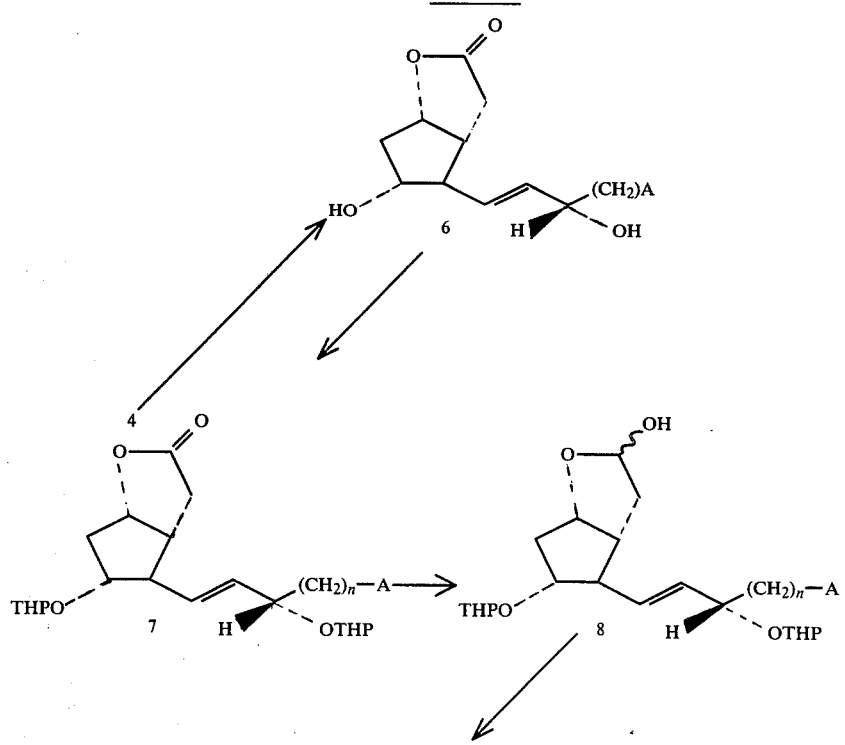

Scheme B

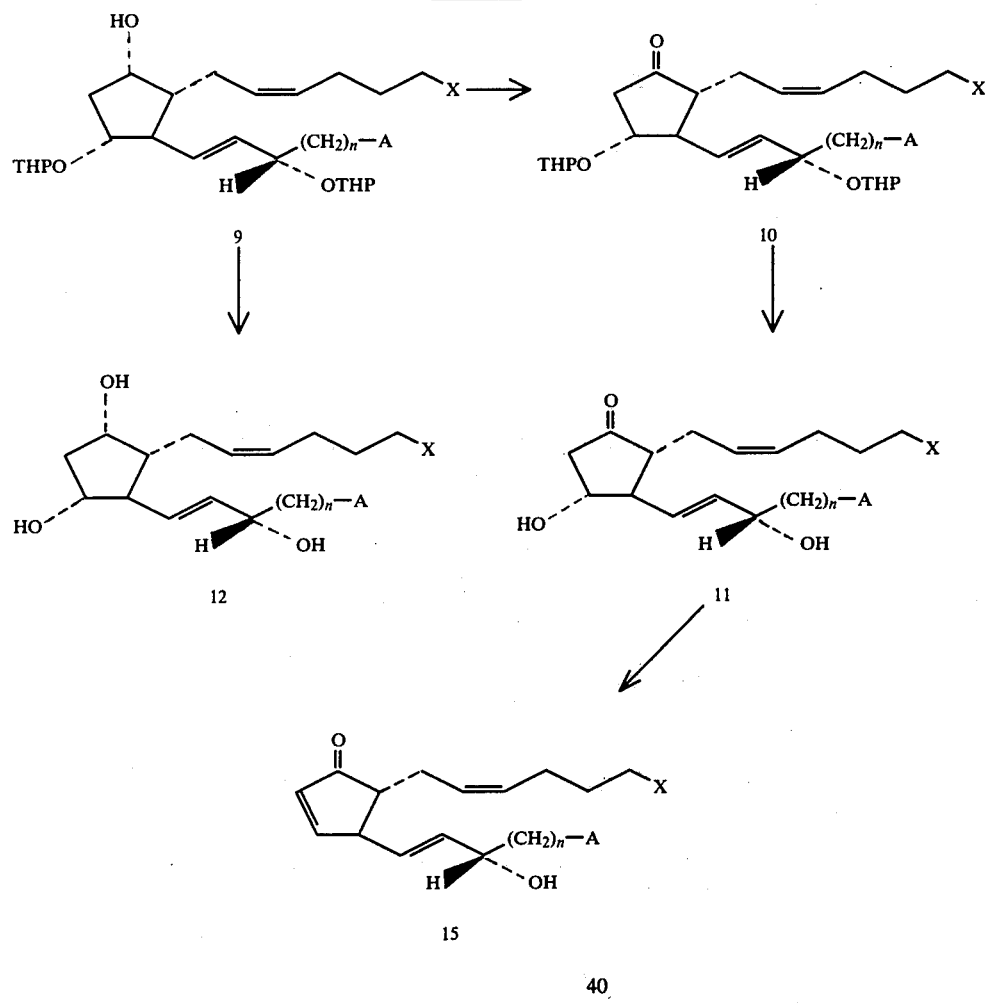

7 → 8 is a reduction of the lactone 7 to the hemiacetal 8 using diisobutyl aluminum hydride in an inert solvent. Low reaction temperatures are preferred and −60° to 70° C. are usual. However, higher temperatures may be employed if over-reduction does not occur. 8 is purified, if desired, by column chromatography.

8 → 9 is a Wittig condensation in which hemiacetal 8 is reacted with, for example, (4-carbohydroxy-n-butyl)-triphenylphosphonium bromide in dimethyl sulfoxide, in the presence of sodium methylsulfinyl methide. 9 is purified as above.

The conversion 9 →12 is an acidic hydrolysis of the tetrahydropyranyl groups. Any acid may be used which does not cause destruction of the molecule in the course of the removal of the protecting group; however, this is accomplished most often by use of 65% aqueous acetic acid. The product is purified as above.

9 → 10 is an oxidation of the secondary alcohol 9 to the ketone 10. This may be accomplished using any oxidizing agent which does not attack double bonds; however, the Jones reagent is usually preferred. The product is purified as above.

10 → is carried out in the same manner as 9 → 12. The product is purified as above. Reduction of the compound 11 with sodium borohydride will provide the 9β isomer of prostaglandin analogs of the F series, i.e. $PGF_{2\beta}$ compunds. These may also be obtained via sodium borohydride reduction of 10 followed by hydrolysis as described above for 10 → 11.

11 → 15 is an acid-catalyzed dehydration. Any acid may be used for the process which does not cause extensive decomposition of the product, but the most usual procedure consists of dissolving

Scheme C
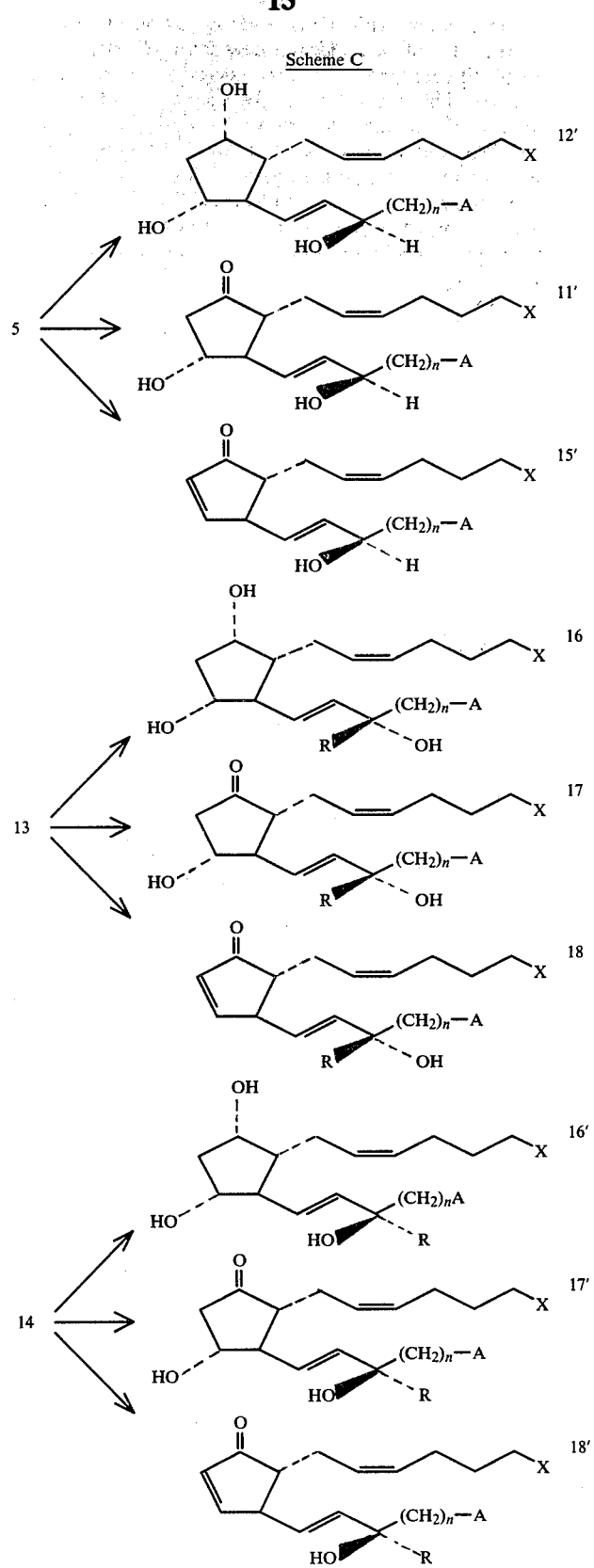
11 in an excess of glacial acetic acid at 70° followed by dilution with ice water and extraction of the product after the starting material has been consumed. The product is purified as above.
As is illustrated in Scheme C, 5, 13 and 14 may be substituted for 4 in scheme B to provide prostaglandin derivatives 12'-18.

Scheme D illustrates the synthesis of precursors to the 13,14-dihydro-15-substituted-pentanorprostaglandins.

In 3 →19 + 19' the enone 3 is reduced to the tetrahydro compound through the use of any of the complex metal hydride reducing agents, LiAlH$_4$, NaBH$_4$, KBH$_4$, LiBH$_4$ and Zn(BH$_4$)$_2$. Especially preferred is NaBH$_4$. The products, 19 and 19', are separated from each other by column chromatography.

Furthermore, the compounds 4 and 5 of Scheme A can be reduced catalytically with hydrogen to 19 and 19' respectively. The stage at which the double bond is reduced is not critical, and hydrogenation of 6 or 7 of Scheme B will also afford useful intermediates for the 13,14 dihydro prostaglandin analogs of the present invention. This reduction may be achieved with either a homogeneous catalyst such as tri-tri-phenylphosphinechlororhodium (I), or with a heterogeneous catalyst such as platinum, palladium or rhodium. In a similar way the precursors to the 15-lower alkyl-15-substituted-ω-pentanorprostaglandins are synthesized by substituting compounds 13 and 14 for 4 and 5 respectively, in the synthesis

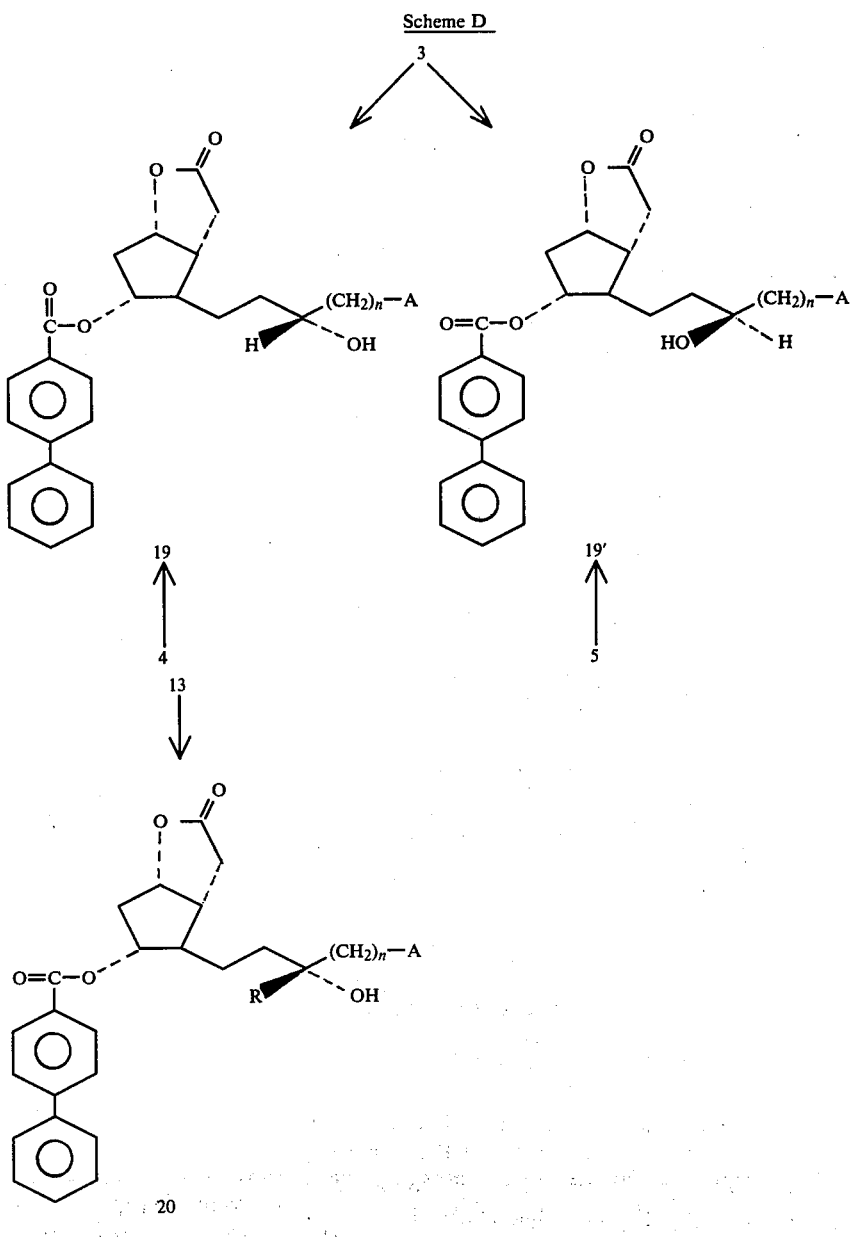

Scheme D

Scheme D

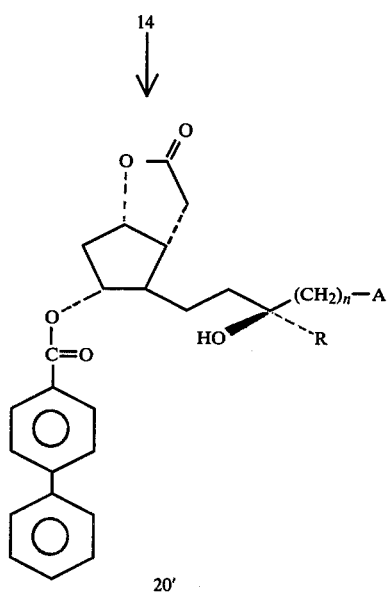

just described. The conversion of 19, 19', 20'and 20 to their respective prostaglandins follows the route shown in scheme B when 4 is replaced by 19, 19', 20' and 20 to yield the 13,14-dihydro PGE₂, PGA₂ and PGF₂ series of prostaglandin derivatives containing hydrogen or lower alkyl group at carbon 15.

Scheme E illustrates the preparation of the various reduced 15-substituted-ω-pentanorprostaglandin precursors:

19 → 22 is carried out as illustrated on Scheme B for 4 → 9, 22 can be used as both a precursor to a 13,14-dihydro 15-substituted-ω-pentanorprostaglandin of the "2-series" or as an intermediate to 23, a precursor to a 13,14-dihydro-15-substituted-ω-pentanorprostaglandin of the "1-series". 22 → 23 is carried out by catalytic hydrogenation using the catalyst described for the reduction of 4 → 19 of Scheme D. Intermediates of the type 21 are prepared by selective reduction of the 5-6 cis double bond at low temperature using catalysts such as those described for 4 → 19 and 17 → 23. Especially prepared for this reduction is the use of palladium on carbon as a catalyst and a reaction temperature of −20°. Intermediates of the type 21 are not only precursors to 15-substituted-ω-pentanorprostaglandins of the "1-series" through the route 9 → 15 of scheme B, but also as a precursor to compounds of the type 23 through the route already discussed for 22 → 23. Furthermore, the 15-substituted-ω-pentanorprostaglandins

Scheme E

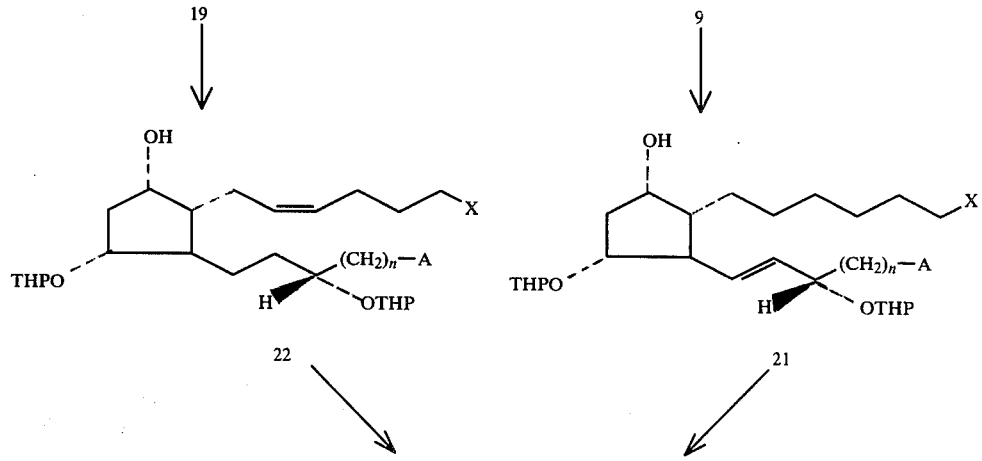

Scheme E

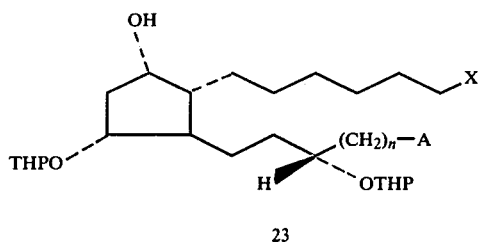

of the $E_1$ and $F_{1\alpha}$ series may be obtained directly from the of corresponding prostaglandin analog of the "2-series" by first protecting the hydroxyl by introducing dimethyl isopropyl silyl groups, reducing selectively the cis double bond, and removing the protecting group.

The introduction of the protecting group is usually accomplished by treatment of the prostaglandin analog with dimethyl isopropyl chlorosilane and triethylamine, the reduction is accomplished as discussed above for 9 → 21 and removal of the protecting group is accomplished by contacting the reduced protected compound with 3:1 acetic acid:water for 10 minutes or until reaction is substantially complete.

The $C_{15}$ epimers of 21, 22 and 23 can be used as precursors to the 15-epi series of prostaglandin derivatives described above, and 15-lower-alkyl-15-substituted-ω-pentanorprostaglandins reduced at the 5-6 and/or the 13,14-position and their $C_{15}$ epimers can be prepared from the appropriately substituted analogs of 9 and 19 whose syntheses follow those of Scheme A and B.

13,14-dihydro-15-lower alkyl-15-substituted-ω-pentanorprostaglandins are available from the appropriately substituted precursors via Scheme E.

The novel esters of this invention can be prepared in several different ways. These differ from one another in that the esterifying group is attached to the prostaglandin or its precurser at different stages of its synthesis.

SCHEME F

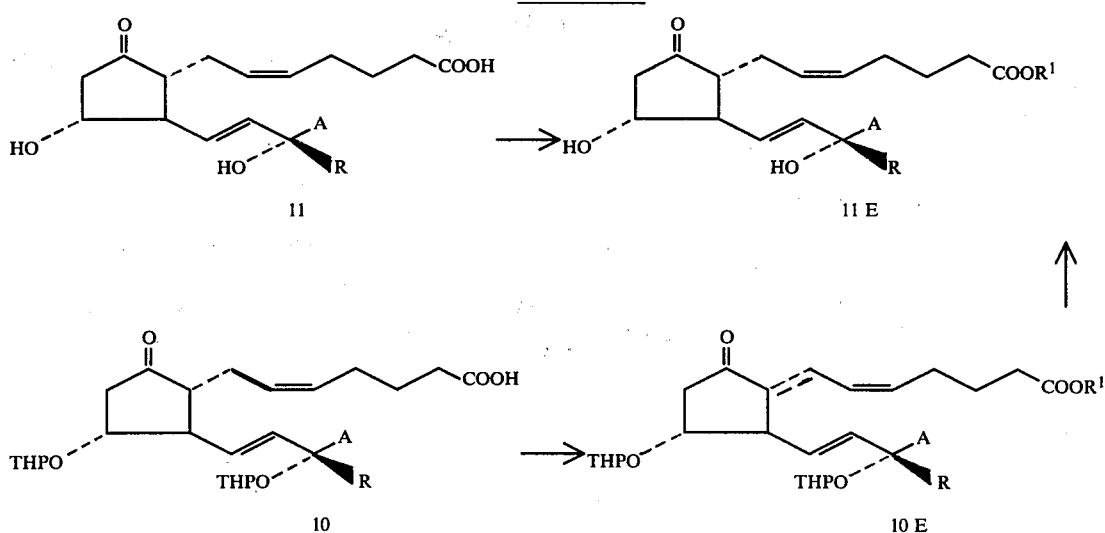

-continued
SCHEME F

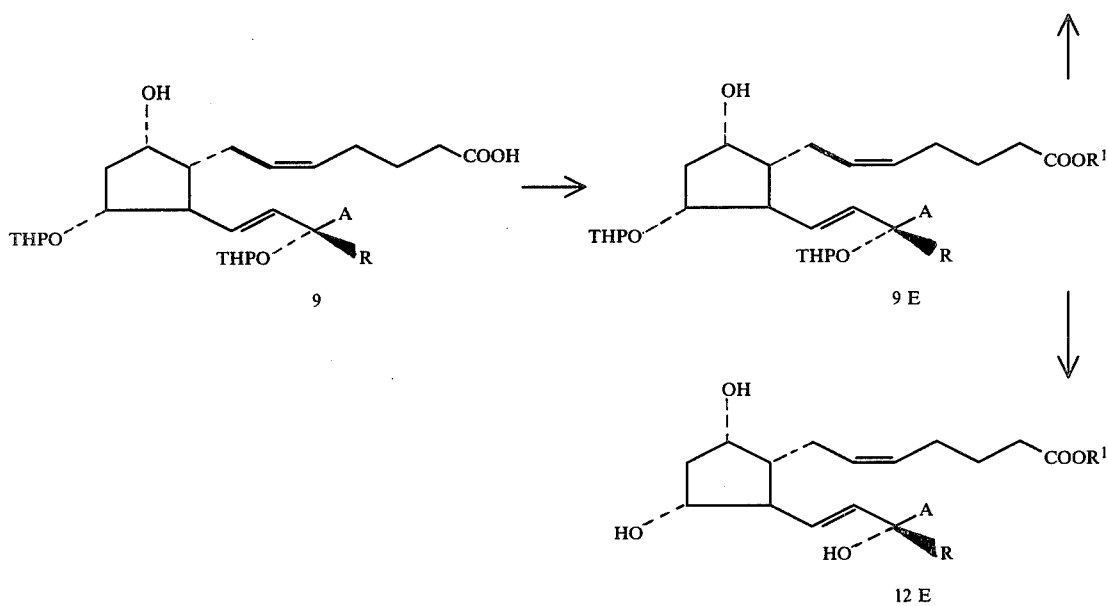

For example Scheme F shows three different routes to the ester "E".

In each case the esterifying group is introduced by an esterification reaction which may be conducted by contacting the appropriate prostaglandin analog or its precursor with the alcohol or phenol in the presence of a catalyst. Alternatively, the prostaglandin or its precursor may be treated with a diazo alkane or cycloalkane in reactions inert solvent to provide the desired ester. Any prostaglandin analog may be used as a substrate for the above esterification reactions, and additionally precursors to such prostaglandins or prostaglandin analogs may also be used as illustrated in Scheme F. For example, 9 may be converted to 9E by the esterification reaction alluded to above and 9E may then be converted to 10E and 12E by the same methods used to convert 9 to 10 and 12 as previously discussed. Compound 10E may be converted to 11E by reactions described for the conversion of 10 to 11.

As is obvious from the above, the esters such as 9E, 10E, 11E and 12E may be used as substrates for the various reductive schemes previously described for the production of the prostaglandin analogs of the "one" and "zero" series.

The prostaglandin analogs of this invention and their esters which are acylated at $C_{11}$ and $C_{15}$ are readily prepared from the corresponding parent by acylation which is usually carried out using carboxylic acid anhydride or carboxylic acid chloride as the acylation agents. To prepare formyloxy derivatives the mixed anhydrides (e.g. formicacetic anhydride) is employed. The $C_9$, $C_{11}$ and $C_{15}$ acyloxy prostagaldnin analogs and their esters are prepared in the same way from the desired PGF precursor.

Various modifications are possible on the upper side chain of the prostaglandins of this invention. A 5-tetrazolyl moiety may be placed at the $C_1$ position as described in one copending application U.S. Ser. No. 177,102 filed Sept. 1, 1971, and in the appended examples. For example, compound 8 may be caused to react with the ylide generated from (4-(tetrazol-5-yl)-n-butyl)-triphenylphosphonium bromide and sodium methylsulfinylmethide to provide the $C_1$ tetrazole-substituted compound 9. Conversion of 9 into the corresponding prostaglandins proceeds as described above.

Another upper side chain modification which may be made in the prostaglandins of this invention is substitution of the carboxylate moiety at the $C_1$ position by a carboximide or carbox-sulfonamide moiety. The methods for preparing these compounds are disclosed in one copending application U.S. Ser. No. 260,518 filed June 7, 1972, and in the appended examples. For example 8 may be caused to react with the ylide generated from (methanesulfonylaminocarboxyl-n-butyl)triphenylphosphonium bromide and sodium methylsulfinylmethide to afford the $C_1$ N-methanesulfonyl carboxamide substituted compound 9. Conversion of 9 into the corresponding prostaglandins proceeds as described above. Alternatively, the novel compounds of this invention represented by structures 9 and 10 of scheme B (where X is

and wherein R" is as previously defined), can be prepared, for example, from compounds 9 and 10 of Scheme B (where X is EOH) by reaction with appropriate acyl- or sulfonyl isocyanates, followed by hydrolysis with dilute acid.

In the foregoing procedures, where purification by chromatography is desired, appropriate chromatographic supports include neutral alumina, silica gel, and fluoracil. The chromatography is suitably conducted in reaction-inert solvents such as ether, ethyl acetate, benzene, chloroform, methylene chloride, cyclohexane, n-hexane, and methanol as further illustrated in the appended examples.

It will be seen that the foregoing formulae depict optically active compounds. It will be clear, however, that the corresponding racemates will exhibit valuable biological activity by virtue of their content of the above-mentioned biologically active optical isomer, and it is intended that such racemates also be embraced by the foregoing formulae herein and in the appended claims. The racemic mixtures are readily prepared by the same methods employed herein to synthesize the optically active species, by mere substitution of corresponding racemic precursors in place of optically active starting materials.

In numerous in vivo and in vitro tests we have demonstrated that the new prostaglandins analogs possess selective physiological activities comparable to those exhibited by the natural prostaglandins. These tests include, among others, a test for effect on isolated smooth muscle from guinea pig uterus, guinea pig ileum and rat uterus, stimulation of diarrhea in mice, inhibition of histamine-induced bronchospasm in the guinea pig, effect on dog blood pressure, inhibition of stress-induced ulceration in the rat, inhibition of gastric acid secretion in the rat and dog, inhibition of lipolysis antiarrhythmic activity, cardiac stimulant activity, inhibition of collagen or ADP-induced blood platelet aggregation and abortifacient activity in rats and guinea pigs by luteolytic and non-luteolytic mechanisms.

The physiological responses observed in these tests are useful in determining the utility of the test substance for the treatment of various natural and pathological conditions. Such determined utilities include: antihypertensive activity, bronchodilator activity, antithrombogenic activity, antiulcer activity, smooth muscle activity [useful as an anti-fertility agent, for the induction of laor, and as an abortifacient], and anti-fertility activity through a mechanism not affecting smooth muscle, for example, luteolytic mechanisms, and the synchronization of the estrous cycle in farm animals.

The novel compounds of this invention possess more selective activity profiles than the corresponding naturally occurring prostaglandins, and in many cases are more potent and exhibit a longer duration of action. For example, 15-(2-indanyl)-$\omega$-pentanorprostaglandin $F_{2\alpha}$- which exhibits guinea pig uterine, smooth muscle stimulating activity comparable to $PGF_{2\alpha}$, has only 8% the guinea pig ileum stimulting activity, and is at least 30 times more potent than $PGF_{2\alpha}$ in abortifacient activity in rats.

The 15-substituted-$\omega$-pentanorprostaglandins of the $PGF_{1\alpha}$, $PGF_{o\alpha}$, and 13,14-dihydro PGFhd 2$\alpha$are similarly selective regarding smooth muscle stimulant activity.

The various modifications of the upper side chain of the prostaglandins of this invention as a rule do not alter the basic biological activity, although they may increase selectivity and duration of action further and reduce toxicity.

Particularly useful forfertility control, abortion and inducation of labor are the 15-(2-indanyl)-$\omega$-pentanorprostaglandins, the 15-(1,2,3,4-tetrahydronaphthyl)-$\omega$-pentanorprostaglandins, the 15-(2-(5,6-dimethylindany-l))-$\omega$-pentanorprostaglandins, 17-(1-adamantyl)-$\omega$-trisnorprostaglandin, and 16-(1-adamantyl)-$\omega$-tetranorprostaglandins of the $E_2$ and $F_{2\alpha}$series based on potent smooth muscle stimulating activity, and abortifacient activity in rats and at the same time reduced blood pressure and diarrhocal effects. Similarly, the substituted-$\omega$-pentanorprostaglandins of the $PGE_1$, $PGF_{o\alpha}$, $PGF_{1\alpha}$, and 13,14-dihydro $PGF_{2\alpha}$series are useful for fertility control including abortion and induction of labor on the basis of their selective smooth muscle stimulant activity. The novel prostaglandins with a $\beta$-OH at the 15-position are in general less potent, although frequently more selective than the corresponding $\alpha$-hydroxyl epimers. Additionally, the prostaglandins having a $\beta$-hydroxyl at C-15 are valuable intermediates to prostaglandins having a $\alpha$-hydroxyl at C-15 through a recycling process involving an oxidation and reduction at C-15. The novel prostaglandin analogs of this invention wherein said prostaglandins are of the A, E, or F series have useful antifertility properties and are further useful synchronization of the estrous cycle in animals.

The novel 15 lower alkyl compounds of this invention have the same profile of activity as the prostaglandin analogs of this invention, where R is hydrogen, from which they are derived. Their special utility is concerned with the fact that their duration of action is much increased over the above said compounds, where R is hydrogen, and in such cases where this is essential the 15-lower alkyl compounds are usually preferred. The prostaglandin analogs which have a beta hydroxyl at $C_{15}$ and possess a $C_{15}$ lower alkyl group have action which is similar to their epimers. In some cases, however, the selectivity that these compounds display exceeds that of the epimeric compounds.

The new compounds of this invention can be used in a variety of pharmaceutical formulations which contain the compound, and they may be administered in the same manner as natural prostaglandins by a variety of routes, such as intravenous, intramuscular, subcutaneous, oral, intravaginal, intra- and extra-amniotic, among others.

For induction of abortion, tablets or an aqueous suspension of a 15-substituted-$\omega$-pentanorprostaglandin of this invention such or alcoholic solution of/15-(2-indanyl)-$\omega$-pentanorprostaglandin would appropriately be administered at oral doses of about 0.1–20 mg., with 1–7 doeses per day being employed. For intravaginal administration a suitable formulation would be lactose tablets or an impregnated tampon of the same agent. For such treatments suitable doses would be from about 0.1–20 mg/dose with 1–7 doses being employed. For intra-amniotic administration a suitable formulation would be an aqueous solution containing 0.05–10 mg/dose with 1–7 doses being employed. For extra-amniotic adminstration a suitable formulation would be an aqueous solution containing 0.005–1 mg/dose with 1–5 doses being employed. Alternatively, the 15-substituted-$\omega$-pentanorprostaglandins of this invention can be infused intravenously for induction of abortion at doses of 0.05–50 $\mu$g/minute for a period of from about 1–24 hours. For synchronization of the estrous cycle in pigs, sheep, cows or horses, a solution or suspension containing 0.03–30 mg/day of the 15-substituted-$\omega$-pentanorprostaglandin is adminstered subcutaneously from 1–4 days.

To prepare any of the above dosage forms or any of the numerous other forms possible, various reaction-inert diluents, excipients or carriers may be employed. Such substances include, for example, water, ethanol, gelatins, lactose, starches, magnesium stearate, talc, vegetable oils, benzyl alcohols, gums, polyalkylene glycols, petroleum jelly, cholesterol, and other known carriers for medicaments. If desired, these pharmaceutical compositions may contain auxiliary substances such as preserving agents, wetting agents, stabilizing agents, or other therapeutic agents such as antibiotics.

The following examples are merely illustrative, and in no way limit the scope of the appended claims. In these examples it will be appreciated that all temperatures are expressed in Centigrade, all melting and boiling points are uncorrected.

EXAMPLE 1

Dimethyl 2-Oxo-3-(1-Adamantyl)propylphosphonate (2a)

A solution of 49.6 g (0.400 moles) dimethyl methylphosphonate (Aldrich) in 500 ml dry tetrahydrofuran was cooled to −78° in a dry nitrogen atmosphere. To the stirred phosphonate solution was added 188 ml of 2.34 M n-butyllithium in hexane solution (Alfa Inorganics, Inc. dropwise over a period of 40 minutes at such a rate that the reaction temperature never rose above −65°. After an additional 5 minutes stirring at −78°, 41.7 g (0.200 mole) methyl (1-adamantyl)-acetate was added dropwise at a rate that kept the reaction temperature less than −70° (20 minutes). After 1.0 hour at −78°, the reaction mixture was allowed to warm to ambient temperature, neutralized with 25 ml acetic acid and rotary evaporated to a white gel. The gelatinous material was taken up in 50 ml water, the aqueous phase extracted with 100 ml portions of methylene chloride (4x), the combined orgaic extracts were backwashed with water (4 × 100 ml), dried (MgSO4), and concentrated (water aspirator) to a crude residue and distilled, b.p 209°-212° (<0.02 mm) to give dimethyl 2-oxo-3-(1-adamantyl)propylphosphonate (2a ).

The nmr spectrum (CDCl3) of the distilled product (2a) exhibited a doublet centered at 3.70 δ(6H; J = 11 cps) for the OCH3, a doublet centered at 2.93δ(2H; J = 23 cps) for COCH2PO, a singlet at 2.23δ(2H) for the CH2CO, a broad singlet at 2.00–1.66δ(3H) for the CH, and a singlet at 1.66–1.30δ(12H) for the remaining protons. The ir spectrum (CHCl3) of 2a showed a strong adsorption at 1710 cm−1 (carbonyl group). Using the above procedure the precursors for 17 through 20 substituted prostaglandin analogs of the present invention can be prepared. They are transformed into the corresponding prostaglandin analogs by the procedures of examples 2–25, 59–85 and 89.

EXAMPLE 2

2-[3α-p-Phenylbenzoyloxy-5α-hydroxy-2β-(3-oxo-4-(1-adamantyl)-trans-1-buten-1-yl)cycopent-1α-yl]acetic acid, γ-lactone (3a)

Dimethyl 2-oxo-3-(1-adamantyl)propylphosphonate (2a) (5.0 g, 17.3 mmole) in 100 ml dry 1,2-dimethoxyethane was treated with 6.5 ml. (15.2 mmole) 2.34 M n-butyllithium in n-hexane (Alfa Inorganics, Inc.) in a dry nitrogen atmosphere at room temperature. After 5 min. of stirring, the reaction mixture was cooled in an ice bath and a solution of 4.76 g (13.6 mmoles) of 2-[3α-p-phenylbenzoyloxy-5α-hydroxy-2β-formylcyclopent-1α-yl]acetic acid, γ-lactone in 40 ml. of dry 1,2-dimethoxyethane was added. After 1 hour at room temperature, the reaction mixture was quenched with 1.5 ml glacial acetic acid, and concentrated. The resultant oil was dissolved in methylene chloride and was extracted with water (3 × 100 ml) and saturated brine (1x), was dried (MgSO4)and concentrated to afford the crude solid 2-[3α-p-phenylbenzoyloxy-5α-hydroxy-2β-(3-oxo-4-(1-adamantyl)-trans-1-buten-1yl)cyclopent-1α-yl]acetic acid, γ-lactone (3a) which was recrystallized from ethanol as platelets weighing 5.21 g (74.7% yield) melting at 199°-200°.

The nmr spectrum (CDCl3) of the crystalline 3a exhibited a multiplet at 8.16-7.20 δ(9H) for the aromatic protons, a multiplet at 6.90-5.96 δ(2H) for the olefinic protons, a multiplet at 5.47-4.82 δ(2H) for the CHO, and multiplets at 3.10-1.30 δfor the remaining protons. The ir spectrum (CHCl3) of 3a exhibited strong adsorptions at 1770 cm−1 (lactone carbonyl) and 1710 cm−1 (ester carbonyl) and medium adsorptions at 1680 and 1620 cm−1 (ketone carbonyl) and at 975 cm−1 (trans olefin).

Anal. for $C_{34}H_{36}O_5$ : Calc. C, 77.83; H, 6.92; Found. C, 77.66; H, 6.88.

EXAMPLE 3

2-[3α-p-Phenybenzoyloxy-5α-hydroxy-2β-(3α-hydroxy-4-(1-adamantyl)-trans-1-buten-1-yl)cyclopent-1α-yl]acetic acid, γ-lactone (4a) and 2-[3α-p-phenylbenzoyloxy-5α-hydroxy-2β-(3β-hydroxy-4-(1-adamantyl)-trans-1-buten-1-yl)cyclopent-1α-yl]acetic acid, γ-lactone (5a)

To a solution 3.95 g (7.54 mmole) 2-[3α-p-phenylbenzoyloxy-5α-hydroxy-2β-(3-oxo-4-(1-adamantyl)-trans-1-buten-1-yl)cyclopent-1α-yl]acetic acid, γ-lactone (3a) in 25 ml dry tetrahydrofuran in a dry nitrogen atmosphere at ambient temperature was added dropwise 7.54 ml of a 0.5 M zinc borohydride solution. After stirring at room temperature for 1.5 hours, a saturated sodium bitartrate solution was added dropwise until hydrogen evolution ceased. The reaction mixture was allowed to stir for 5 minutes, at which time 250 ml dry methylene chloride was added. After drying (MgSO4 ) and concentrating (water aspirator), the resultant semisolid was purified by column chromatography on silica gel (Baker "Analyzed" Reagent 60-200 mesh) using a 9:1 mixture of ether: cyclohexane as eluent. After elution of less polar impurities, a fraction containing 588 mg 2-[3α-p-penylbenzoyloxy-5-6O-hydroxy-2β-(3α-hydroxy-4-(1-adamantyl)-trans-1-buten-1-yl) cyclopent-1α-yl]acetic acid, γ-lactone (4a) m.p. 185°-187° from methylene chloride-hexane and a fraction (522 mg) of 2-[3α-p-phenylbenzoyloxy-5α-hydroxy-2β-(3β-hydroxy-4 -(1-adamantyl)-trans-1-buten-1-yl) cyclopent-1α-yl]acetic acid, γ-lactone (5a) were collected.

The ir spectrum (CHCl3) of 4a had strong adsorption at 1775 cm−1 (lactone carbonyl) and 1715 cm−1 (ester carbonyl) and a medium adsorption at 975 cm−1 (trans olefin). The nmr spectrum (CDCl3) of 4a exhibited a multiplet at 8.12-7.15 δ(9H) for the aromatic protons, a multiplet at 5.76-5.45 δ(2H) for the trans double bond, a multiplet at 5.45-4.81 δ(2H) for the CHOCO, a multiplet at 4.47-4.00 δ(1H) for the CHOH, and multiplets at 2.90-1.10 δfor the remaining protons.

EXAMPLE 4

2-[3α,5α-Dihydroxy-2β-(3α-hydroxy-4-(1-adamantyl)-trans-1-buten-1-yl)cyclopent-1α-yl]acetic acid, γ-lactone (6a):

A heterogeneous mixture of 1.23 g (2.20 mmole) of 2-[3α-p-phenylbenzoyloxy-5α-hydroxy-2β-(3α-hydroxy-4-(1-adamantyl)-trans-1-buten-1-yl)cyclopent-1α-yl]acetic acid, γ-lactone (4a), 20 ml. of absolute methanol, 15 ml. of dry tetrahydrofuran and 316 mg of finely powdered, anhydrous potassium carbonate was stirred at room temperature for 1.5 hour, then cooled to 0°. To the cooled solution was added 4.5 ml (4.5 mmole) of 1.0N aqueous hydrochloric acid. The solution was extracted with ethyl acetate (3x); the combined extracts were washed with saturated sodium bicarbonate (1x), were dried (MgSO4), and concentrated to afford a crude semi-solid which was purified by silica gel column chromatography. After elution of less polar impurities with chloroform, elution with 5% methanol in methylene chloride afforded the desired 2-[3α,5α-dihydroxy-2β-(3α-hydroxy-4-(1-adamantyl)-trans-1-buten-1-yl)cyclopent-1α-yl]acetic acid, γ-lactone (6a), as a viscous, colorless oil weighing 755 mg (95.5% yield).

The ir spectrum (CHCl₃) exhibited a strong adsorption at 1770 cm⁻¹ for the lactone carbonyl and medium adsorption at 975 cm⁻¹ for the trans-double bond.

EXAMPLE 5

2-[5α-Hydroxy-3α-(tetrahydropyran-2-yloxy)-2β-(3α-{tetrahydropyran-2-yloxyγ-4-(1-adamantyl)-trans-1-buten-1-yl)cyclopent-1α-yl]acetic acid, γ-lactone (7a):

To a solution of 755 mg (2.24 mmole) 2-[3α,5α-dihydroxy2β-(3α-hydroxy-4-(1-adamantyl)-trans-1-buten-1yl)cyclopent-1α-yl]acetic acid, γ-lactone (6a) in 8 ml anhydrous methylene chloride and 0.86 ml of 2,3-dihydropyran at 0° in a dry nitrogen atmosphere was added 8 mg p-toluenesulfonic acid, monohydrate. After stirring for 15 minutes, the reaction mixture was combined with 100 ml ether, the ether solution washed with saturated sodium bicarbonate (1 × 15 ml) and then with saturated brine (1 × 15 ml, dried (MgSO₄) and concentrated to yield 1.43 g (>100%) crude 2-[5α-hydroxy-3α-(tetrahydropyran-2-yloxy)-2β-(3α-{tetrahydropyran-2-yloxy}-4-(1-adamantyl)trans-1-buten-1-yl)cyclopent-1α-yl]acetic acid, γ-lactone (7a).

The ir spectrum (CHCl₃) had a strong adsorption at 177 cm⁻¹ (lactone carbonyl) and a medium adsorption at 970 cm⁻¹ (trans olefin).

2-[5α-Hydroxy-3α-(tetrahydropyran-2-yloxy)-2β-(3α-{tetrahydropyran-2-yloxy}-4-(1-adamantyl)-trans-1-buten-1-yl)cyclopent1α-yl]acetaldehyde, γ-hemiacetal (8α):

A solution of 1.43 g (2.88 mmole) 2-[5α-hydroxy-3α-tetrahydropyran-2-yloxy)-2β-(3α-{tetrahydropyran-2-yloxy}4-(1-adamantyl)-trans-1-buten-1-yl)cyclopent-1α-yl]acetic acid, γ-lactone (7α) in 12 ml dry toluene was cooled to −78° in a dry nitrogen atmosphere. To this cooled solution was added 3.66 ml of 20% diisobutylaluminum hydride in n-hexane Alfa Inorganics) dropwise at such a rate so that the internal temperature never rose above −65° (15 minutes). After an additional 30 minutes of stirring at −78°, anhydrous methanol was added until gas evolution ceased and the reaction mixture was allowed to warm to room temperature. The reaction mixture was combined with 100 ml ether, washed with 50% sodium potassium tartrate solution (4 × 20 ml), dried (MgSO₄) and concentrated to afford the crude 2-[5α-hydroxy-3α-(tetrahydropyran-2-yloxy)-2β-(3α-{tetrahydropyran-2-yloxy}-4-(1-adamantyl)-trans-1-buten-1-yl)cyclopent-1-yl]acetaldehyde, γ-hemiacetal (8a) which was purified by silica gel column chromatography using chloroform as eluent. After elution of less polar impurities, the purified product 8a was collected as a viscous, colorless oil weighing 961 mg.

The product of this reaction is converted to 16-(1-adamantyl)-ω-tetranorporstaglandin tetrazoles, carboximides and sulfonimides of the A, E or F series via the procedures of examples 103–110, 140–141, 156–165 and 169–170.

EXAMPLE 7

9α-Hydroxy-11α,15α-bis-(tetrahydropyran-2-yloxy)-16-(1-adamantyl)-cis-5-trans-13-ω-tetranorprostadienoic acid (9a):

To a solution of 2.48 g (5.6 mmole) (4-carbohydroxy-n-butyl)triphenylphosphonium bromide in a dry nitrogen atmosphere in 3.0 ml dry dimethyl sulfoxide was added 6.0 ml (10.7 mmole) of a 1.8 M solution of sodium methylsufinylmethide in dimethyl sulfoxide. To this red ylide solution was added dropwise a solution of 961 mg (1.86 mmole) 2-[5α-hydroxy-3α-(tetrahydropyran-2-yloxy)-2β-(3α-{tetrahydropyran-2-yloxy}4-(1-adamantyl)-trans-1-buten-1-yl)cyclopent-1α-yl]acetaldehyde, γ-hemiacetal (8a) in 3.0 ml dry dimethyl sulfoxide over a period of 20 minutes. After an additional 1.5 hours stirring at room temperature, the reaction mixture was poured into ice water. The basic aqueous solution was acidified to pH∼3 with 10% aqueous hydrochloric acid. The acidic solution was extracted with ethyl acetate (3 × 50 ml) and the combined organic extracts washed once with water (10 ml), dried (MgSO₄) and evaporated to a solid residue which was purified by column chromatography on silica gel (Baker "Analyzed" Reagent 60–200 mesh) using mixtures of chloroform ethyl acetate as eluent. After removal of high R$_f$ impurities, 791 mg of 9α-hydroxy-11α, 15α-bis-(tetrahydropyran-2-yloxy)-16-(1-adamantyl)-cis-5-trans-13-ω-tetranorprostadienoic acid (9a) was collected.

The ir spectrum (CHCl₃) of 9a had a strong adsorption at 1700 cm⁻¹ (acid carbonyl) and a medium adsorption at 970 cm⁻¹ (trans olefin). The nmr spectrum (CDCl₃) exhibited a broad singlet at 6.78–6.20 δ (2H) for the OH, a multiplet at 5.63–5.20 δ (4H) for the olefinic protons, a singlet at 4.75–4.50 δ (2H) for the OCHO, multiplets at 4.29 –3.19 δ (7H) for the CH₂O) and CHO, and multiplets at 2.51–1.10 δ for the remaining protons.

EXAMPLE 8

9-Oxo-11α,15α-bis-(tetrahydropyran-2-yloxy)-16-(1-adamantyl)-cis-5-trans-13-ω-tetranorprostadienoic acid (10a)

To a solution cooled to −10° under nitrogen of 651 mg (1.09 mmole) 9α-hydroxy-11α,15α-bis-(tetrahydropyran-2-yloxy)-16-(1-adamantyl)-cis-5-trans-13-ω-tetranorprostadienoic acid (9a) in 10 ml reagent grade acetone was added dropwise to 0.47 ml of Jones' reagent. After 15 minutes at −10°, 0.47 ml 2-propanol was added and the reaction mixture was allowed to stir and additional 5 minutes, at which time it was combined with 100 ml ethyl acetate, washed with water (3 × 10 ml), dried (MgSO₄) and concentrated to give 561 mg of 9-oxo-11α,15α-bis-(tetrahydropyran-2-yloxy)-16-(1-adamantyl)-cis-5trans-13-ω-tetranorprostadienoic acid (10a) which was used without purification.

EXAMPLE 9

9-Oxo-11α,15α-dihydroxy-16-(1-adamantyl)-cis-5-trans-13-ω-tetranorprostadienoic acid (11a)

A solution of 561 mg (0.94 mmole) 9-oxo-11α,15α-bis-(tetrahydropyran-2-yloxy)-16-(1-adamantyl)-cis-5-trans-13-ω-tetranorprostadienoic acid (10a) in 10 ml of a 65:35 mixture of glacial acetic acid:water was stirred under nitrogen at room temperature for 18 hours and then was concentrated by rotary evaporation. The resultant crude oil was purified by column chromatography on silica gel (Mallinckrodt CC-4 100–200 mesh) using mixtures of benzene:ethyl acetate as eluents. After elution of less polar impurities, the viscous, colorless 9-oxo-11α,15α-dihydroxy-16-(1-adamantyl)-cis-5-trans-13-ω-tetranorprostadienoic acid (11a) weighing 196 mg was collected.

The ir spectrum (CHCl$_3$) of 11a had strong adsorptions at 1710 cm$^{-1}$ (acid carbonyl) and 1735 cm$^{-1}$ (ketone carbonyl) and a medium adsorption at 970 cm$^{-1}$ (trans olefin). The nmr spectrum (CDCl$_3$) of 11a exhibited a singlet at 5.90 δ (3H) for the OH, a multiplet at 5.79–5.52 δ (2H) for the trans olefin, a multiplet at 5.52–5.22 δ (2H) for the cis olefin, a multiplet at 4.52–3.68 δ (2H) for the CHO and CH$_2$O multiplets at 2.72–1.08 δ for the remaining protons.

EXAMPLE 10

9α,11α,15α-Trihydroxy-16-(1-adamantyl)-cis-5-trans-13-ω-tetranorprostadienoic acid (12a)

A solution of 140 mg of 9α-hydroxy-11α,15α-bis-(tetrahydropyran-2-yloxy)-16-(1-adamantyl)-cis-5-trans-13-ω-tetranorprostadienoic acid (9a) in 3 ml of a 65:35 mixture of glacial acetic acid:water was stirred under nitrogen at room temperature for 18 hours, then was concentrated by rotary evaporation. The resultant semi-solid was recrystallized from ethanol:hexane to afford the 9α,11α,15α-trihydroxy-16-(1-adamantyl)cis-5-trans-13-ω-tetranorprostadienoic acid (12a) weighing 33 mg, melting at 167.5–168.0°.

The ir spectrum (KBr) of 12a had a strong adsportion at 5.84 μ (acid carbonyl) and a medium adsorption at 10.25 μ (trans olefin). The mass spectrum of 12a exhibited peaks at M-18 and M-36.

EXAMPLE 11

2-(3α,5α-Dihydroxy-2β-(3β-hydroxy-4-(1-adamantyl)-trans-1-buten-1-yl)cyclopent-1α-yl)acetic acid, γ-lactone (6′a)

A heterogeneous mixture of 1.89 g (2.12 mmole) of 2-[3α-p-phenylbenzoyloxy-5α-hydroxy-2β-(3β-hydroxy-4-(1-adamantyl)-trans-1-buten-1-yl)cyclopent-1α-yl]acetic acid, γ-lactone (5a), 20 ml of absolute methanol, 10 ml of dry tetranhydrofuran and 266 mg of finely powdered, anhydrous potassium carbonate was stirred at room temperature for 1.5 hour, then cooled to 0°. To the cooled solution was added 4.0 ml (4.0 mmole) of 1.0 N aqueous hydrochloric acid. The solution was extracted with ethyl acetate (3x); the combined extracts were washed with saturated sodium bicarbonate (1x), were dried (MgSO$_4$), and concentrated to afford a crude semi-solid which was purified by silica gel column chromatography. After elution of less polar impurities with chloroform, elution with 5% methanol in methylene chloride afforded the desired 2-[3α,5α-dihydroxy-2β-(3β-hydroxy-4-(1-adamantyl)-trans-1-buten-1-yl]cyclopent-1α-yl) acetic acid, γ-lactone (6′a), as a viscous, colorless oil weighing 495 mg (67.3% yield).

The ir spectrum (CHCl$_3$) of 6′a exhibited a strong adsorption at 1770 cm$^{-1}$ for the lactone carbonyl and medium adsorption at 975 cm$^{-1}$ for the trans-double bond.

EXAMPLE 12

2-[5α-Hydroxy-3α-(tetrahydropyran-2-yloxy)-2β-(3β-(tetrahydropyran-2-yloxy)-4-(1-adamantyl)-trans-1-buten-1-yl)cyclopent-1α-yl]acetic acid, γ-lactone (7′a)

To a solution of 495 mg (1.43 mmole) 2-[3α,5α-dihydroxy2β-(3β-hydroxy-4-(1-adamantyl)-trans-1-buten-yl]cyclopent-1α-yl)acetic acid, γ-lactone (6′a) in a 5 ml anhydrous methylene chloride and 0.79 ml of 2,3-dihydropyran at 0° in a dry nitrogen atmosphere was added 5 mg p-toluenesulfonic acid, monohydrate. After stirring for 15 minutes, the reaction mixture was combined with 100 ml ether, the ether solution washed with saturated sodium bicarbonate (1 × 15 ml) then saturated brine (1 × 15 ml), dried (MgSO$_4$) and concentrated to yield 0.908 g (>100%) crude 2-[5α-hydroxy-3α-(tetrahydropyran-2-yloxy)-2β-(3β-(tetrahydropyran-2-yloxy)-4-(1-adamantyl)-trans-1-buten-1-yl)cyclopent-1α-yl]acetic acid, γ-lactone (7′a).

The ir spectrum (CHCl$_3$) had a strong adsorption at 1770 cm$^{-1}$ (lactone carbonyl) and a medium adsorption at 970 cm$^{-1}$ (trans olefin).

EXAMPLE 13

2-[5α-Hydroxy-3α-(tetrahydropyran-2-yloxy)-2β-(3β-(tetrahydropyran-2-yloxy)-4-(1-adamantyl)-trans-1-buten-1-yl)cyclopent-1α-yl]acetaldehyde, γ-hemiacetal (8′a)

A solution of 0.735 g (1.43 mmole) 2-[5α-hydroxy-3α(tetrahydropyran-2-yloxy)-2β-(3β-(tetrahydropyran-2-yloxy)-4-(1-adamantyl)-trans-1-buten-1-yl)cyclopent-1α-yl]acetic acid, γ-lactone (7′a) in 6 ml dry toluene was cooled to −78° in a dry nitrogen atmosphere. To this cooled solution was added 1.57 ml of 20% ml of 20% diisobutylaluminum hydride in n-hexane (Alfa Inorganics) dropwise at such a rate so that the internal temperature never rose above −65° (15 minutes). After an additional 30 minutes of stirring at −78°, anhydrous methanol was added until gas evolution ceased and the reaction mixture was allowed to warm to room temperature. The reaction mixture was combined with 100 ml ether, washed with 50% sodium potassium tartrate solution (4 × 20 ml), dried (MgSO$_4$) and concentrated to afford the crude 2-[5α-hydroxy-3α-(tetrahydropyran-2-yloxy)-2β-(3β-(tetrahydropyran-2-yloxy)-4-(1-adamantyl)-trans-1-buten-1-yl)cyclopent-1α-yl]acetaldehyde, γ-hemiacetal (8′a) which was purified by silica gel column chromatography using chloroform as eluent. After elution of less polar impurities, the purified product 8′a was collected as a viscous, colorless oil weighing 669 mg (90.8% yield).

The product of this reaction is converted to 15-epi-16-(1-adamantyl)-ω-tetranorprostaglandin tetrazoles, carboximides and sulfonimides of the A, E or F series via the procedures of examples 103–110, 140–141, 156–165 and 169–170.

EXAMPLE 14

9α-Hydroxy-11α,15β-bis-(tetrahydropyran-2-yloxy)-16-(1-adamantyl)-cis-5-trans-13-ω-tetranorprostadienoic acid (9′a):

To a solution of 1.60 g (3.62 mmole) (4-carbohydroxy-n-butyl)triphenylphosphonium bromide in a dry nitrogen atmosphere in 3.0 ml dry dimethyl sulfoxide was added 3.8 ml (6.74 mmole) of a 1.77 M solution of sodium methylsufinylmethide in dimethyl sulfoxide. To this red ylide solution was added dropwise a solution of 669 mg (1.29 mmole) 2-(5α-hydroxy-3α-(tetrahydropyran-2-yloxy)-2β-(β-(tetrahydropyran--2-yloxy)-4-(1-adamantyl)-trans-1-buten-1-yl)cyclopent-1α-yl)acetaldehyde, γ-hemiacetal (8'a) in 2.0 ml dry dimethyl sulfoxide over a period of 20 minutes. After an additional 1.5 hours stirring at room temperature, the reaction mixture was poured onto ice water. The basic aqueous solution was acidified to pH23 with 10% aqueous hydrochloric acid. The acidic solution was extracted with ethyl acetate (3 × 50 ml) and the combined organic extracts washed once with water (10 ml), dried (MgSO$_4$) and evaporated to a solid residue which was purified by column chromatography on silica gel (Baker "Analyzed" Reagent 60–200 mesh) using mixtures of chloroform:ethyl acetate as eluent. After removal of high R$_f$ impurities, 467 mg (60.4% yield) of 9α-hydroxy-11α,15β-bis-(tetrahydropryan-2-yloxy)-16-(1-adamantyl)-cis-5-trans-13-ω-tetranorprostadienoic acid (9'a) was collected.

The ir spectrum (CHCl$_3$) of 9'a had a strong adsorption at 1700 cm$^{-1}$ (acid carbonyl) and a medium adsorption at 970 cm$^{-1}$ (trans olefin). The nmr spectrum (CDCl$_3$) exhibited a broad singlet at 6.78 –6.20 δ (2H) for the OH, a multiplet at 5.63–5.20 δ (4H) for the olefinic protons, a singlet at 4.75–4.50 δ (2H) for the OCHO, multiplets at 4.29–3.19 δ (7H) for the CH$_2$O and CHO, and multiplets at 2.51–1.10 δ for the remaining protons.

EXAMPLE 15

9α,11α,15β-Trihydroxy-16-(1-adamantyl)-cis-5-trans-13-w-tetranorprostadienoic acid (12'a)

A solution of 124 mg of 9α-hydroxy-11α-15β-bis-(tetrahydropyran-2-yloxy)-16-(1-adamantyl)-cis-5-trans-13-w-tetranorprostadienoic acid (9'a) in 3 ml of a 65:35 mixture of glacial acetic acid: water was stirred under nitrogen at room temperature for 18 hours, then was concentrated by rotary evaporation. The resultant crude product was purified by column chromatography (Mallinckrodt CC-4) using removal of less polar impurities the desired 9α,11α,15β-trihydroxy-16-(1-adamantyl)-cis-5-trans-13-w-tetranorporstadienoic acid (12'a) weighing 38 mg was collected as a viscous oil.

The ir spectrum (CHCl$_3$) of 12'a had a strong adsorption at 5.84μ (acid carbonyl) and a medium adsorption at 10.25μ (trans olefin). The nmr spectrum (CDCl$_3$) exhibited a multiplet at 5.66–5.19 (4H) for the olefinic protons, a broad singlet at 5.00–4.55 (3H) for the CHO, and multiplets at 2.50–0.90 for the remaining protons.

EXAMPLE 16

9-Oxo-11α,15-bis-(tetrahydropyran-2-yloxy)-16-(1-adamantyl)-cis-5-trans-13-w-tetranorprostadienoic acid (10'a)

To a solution cooled to −10° under nitrogen of 467 mg 0.778 mmole) 9α-hydroxy-11α,15β-bis-(tetrahydropyran-2-yloxy)-16-(1-adamantyl)-cis-5-trans-13-w-tetranorprostadienoic acid (9'a) in 10 ml reagent grade acetone was added dropwise to 0.28 ml of Jones' reagent. After 15 minutes at −10°, 0.28 ml 2-propanol was added and the reaction mixture was allowed to stir an additional 5 minutes at which time it was combined with 100 ml ethyl acetate, washed with water (3 × 10 ml), dried (MgSO$_4$) and concentrated to give 441 mg of 9-oxo-11α,15β-bis-(tetrahydropyran-2-yloxy)-16-(1-adamantyl)-cis-5-trans-13-w-tetranorprostadienoic acid (10'a) which was used without purification.

EXAMPLE 17

9-Oxo-11α,15β-dihydroxy-16-(1-adamantyl)-cis-5-trans-13-w-tetranorprostadienoic acid (11'a)

A solution of 441 mg (0.94 mmole) 9-oxo-11α,15β-bis-tetrahydropyran-2-yloxy)-16-(1-adamantyl)-cis-5-trans-13-w-tetranorprostadienoic acid (10'a) in 10 ml of a 65:35 mixture of glacial acetic acid:water was stirred under nitrogen at room temperature for 18 hours then was concentrated by rotary evaporation. The resultant crude oil was purified by column chromatography on silica gel (Mallinckrodt CC-4 100–200 mesh) using mixtures of chloroform ethyl acetate as eluent. After elution of less polar impurities the viscous, colorless 9-oxo-11α,15β-dihydroxy-16-(1-adamantyl)-cis-5-trans-13-w-tetranorprostadienoic acid (11'a) weighing 150 mg was collected.

The ir spectrum (CHCl$_3$) of 11'a had strong adsorptions at 1710 cm$^{-1}$ (acid carbonyl) and 1735 cm$^{-1}$ (ketone carbonyl) and a medium adsorption at 970 cm$^{-1}$ (trans olefin). The nmr spectrum (CDCl$_3$) of 11'a exhibited a singlet at 5.90 δ (2H) for the OH, a multiplet at 5.79–5.52 δ (2H) for the trans olefin, a multiplet at 5.52–5.22 δ (2H) for the cis olefin, a multiplet at 4.52–3.68 δ (2H) for the CHO, and multiplets at 2.72–1.08 δ for the remaining protons.

EXAMPLE 18

16-(1-Adamantyl)-ω-tetranorprostaglandin F$_{2β}$

To a solution under nitrogen cooled in ice of 100 mg (0.233 mmole) of 16-(1-adamantyl)-ω-tetranorprostaglandin E$_2$ in 10 ml of absolute methanol was added an ice-cooled solution of 300 mg of sodium borohydride in methanol. The solution was stirred at 0° for 20 minutes then at room temperature for 1.0 hour. The solution was then quenched by the addition of 2.0 ml of water and the methanol was removed by rotary evaporation. The resultant aqueous solution was overlaid with ethyl acetate (10 ml), was acidified by the addition of 10% hydrochloric acid, and was extracted with ethyl acetate (4 × 5 ml). The combined organic extracts were washed with water (5 ml) and saturated brine (5 ml), was dried (anhydrous magnesium sulfate), and was concentrated. Purification of the crude residue by silica gel chromatography using mixtures of methylene chloride-methanol as eluent provided 16-(1-adamantyl)-ω-tetranorprostaglandin F$_{2α}$ (49 mg) and 16-(1-adamantyl)-ω-tetranorprostaglandin F$_{2β}$ (39 mg).

EXAMPLE 19

15-epi-16-(1-adamantyl)-ω-tetranorprostaglandin E$_2$ ethyl ester

To a solution of 15-epi-16-(1-adamantyl)-ω-tetranorprostaglandin E$_2$ (25 mg) in 5 ml of ether was added a solution of diazoethane in ether until the reaction mixture remained yellow for 5 minutes. Concentration of the reaction mixture followed by silica gel column chromatography of the residue using chloroform as eluent afforded the desired 15-epi-16-(1-adamantyl)-ω-tetranorprostaglandin E$_2$ ethyl ester weighing 22 mg.

EXAMPLE 20

9-oxo-11α,15β-dihydroxy-16-(1-adamantyl)-ω-tetranorprostanoic acid (28a)

A heterogeneous mixture of 150 mg 9-oxo-11α,15β-dihydroxy-16-(1-adamantyl)-5-cis-13-trans-13-ω-tetranorprostadienoic acid (11a) and 15 mg of 5% palladium on carbon in 15 ml of absolute methanol is stirred under 1 atmosphere of hydrogen at 0° for 3 hours. The reaction mixture is filtered (Celite) and concentrated. The crude product is purified by silica gel chromatography to provide 9-oxo-11α,15β-dihydroxy-16-(1-adamantyl)-ω-tetranorprostanoic acid (28a).

EXAMPLE 21

9-oxo-11α,15α-bisformyloxy-16-(1-adamantyl)-5-cis-13-trans-ω-tetranorprostadienoic acid To a solution of 43 mg (0.1 mmole) of 9-oxo-11α,15α-dihydroxy-16-(1-adamantyl)-5-cis-13-trans-ω-tetranorprostadienoic acid (11a) in 0.5 ml of dry tetrahydrofuran is added 29 mg (0.33 mmole) of formic acetic anhydride and 35 mg (0.33 mmole) of 2,6-lutidine. The solution is stirred for 1 hour under nitrogen at room temperature then 36 mg (2.0 mmoles) of water is added. The mixture is stirred at room temperature for an additional 1.0 hour then is diluted with ethyl acetate. The diluted solution is washed with 0.1 N hydrochloric acid (1x), with water (1x), and with saturated brine (1x), is dried (anhydrous magnesium sulfate), and is concentrated. Purification of the crude residue by silica gel chromatography affords the 9-oxo-11α,15α-bisformyloxy-16-(1-adamantyl)-5-cis-13-trans-ω-tetranorprostadienoic acid.

EXAMPLE 22

9β,11α,15α-Trispivaloyloxy-16-(1-adamantyl)-5-cis-13-trans-ω-tetranorprostadienoic acid To a solution of 86 mg (0.2 mmole) of 9β,11α,15α-trihydroxy-16-(1-adamantyl)-5-cis-13-trans-ω-tetranorprostadienoic acid (12a) in 1ml of pyridine is added 120 mg (1.0 mmole) of pivaloyl chloride. The solution is stirred for 4 hours at 45° under nitrogen then is cooled to room temperature. To the solution is then added 36 mg (2.0 moles) of water. The solution is then stirred at room temperature for 2.0 hours, then is diluted with ethyl acetate. The diluted solution is washed with 0.1 n hydrochloric acid (2x), with water (1x), and with saturated brine (1x), is dried (anhydrous magnesium sulfate), and is concentrated. Purification of the crude residue by silica gel chromatography provides the 9β,11α,15α-trispivaloyloxy-16-(1-adamantyl)-5-cis-13-trans-ω-tetranorprostadienoic acid.

EXAMPLE 23 p-Biphenyl 9-oxo-11α,15α-dihydroxy-16-(1-adamantyl)5-cis-13-trans-ω-tetranorprostadienoate To a solution of 79 mg (0.18 mmole) 9-oxo-11α,15α-dihydroxy-16-(1-adamantyl)-5-cis-13-trans-ω-tetranorprostadienoic acid (11a) and 320 mg (1.8 mmole) of p-phenylphenol in 8 ml of dry methylene chloride is added 2.4 ml of a 0.1 M solution of dicyclohexylcarbodiimide in methylene chloride. The solution is stirred under nitrogen at room temperature overnight then is concentrated to a white solid. The crude product is purified by silica gel chromatography using first chloroform as element to remove the excess p-phenylphenol. Elution with ethyl acetate provides the p-biphenyl 9-oxo-11α,15α-dihydroxy-16-(1-adamantyl)-5-cis-13-trans-ω-tetranorprostadienoate.

EXAMPLE 24

Cyclopropyl 9α,11α,15α-trihydroxy-16-(1-adamantyl)-5-cis-13-trans-ω-tetranorprostadienoate To a solution of 87 mg (0.20 mmole) of 9α,11α,15α-trihydroxy-16-(1-adamantyl)-5-cis-13-trans-ω-tetranorprostadienoic acid (12a) in 5 ml of dry methylene chloride is added 22 mg (0.22 mmole) of triethylamine. The mixture is stirred for 5 minutes then 24 mg (0.22 mmole) of pivaloyl chloride is added. The solution is stirred for 45 minutes at room temperature under nitrogen then 58 mg (0.1 mmole) of cyclopropyl alcohol and 150 μl of pyridine are added. The mixture is stirred at room temperature for an additional 2.0 hours then is diluted with ethyl acetate. The diluted solution is washed with water (2x) and saturated brine (1x), is dried (anhydrous magnesium sulfate), and is concentrated. Purification of the crude residue by silica gel chromatography provides the cyclopropyl 9α,11α,15α-trihydroxy-16-(1-adamantyl)-5-cis-13-trans-ω-tetranorprostadienoate.

EXAMPLE 25 p-Biphenyl 9-oxo-11α,15α-dihydroxy-16-(1-adamantyl)-5-cis-13-trans-ω-tetranorprostadienoate To a solution of 79 mg (0.18 mmole) of 9-oxo-11α,1-5α-dihydroxy-16-(1-adamantyl)-5-cis-13-trans-ω-tetranorprostadienoic acid (11a) and 320 mg (1.8 mmole) of p-phenylphenol in 8 ml of dry methylene chloride is added 2.4 ml of a 0.1M solution of dicyclohexylcarbodiimide in methylene chloride. The solution is stirred under nitrogen at room temperature overnight then is concentrated to a white solid. The crude product is purified by silica gel chromatography using first chloroform as element to remove the excess p-phenylphenol. Elution with ethyl acetate provides the p-biphenyl 9-oxo-11α, 15α-dihydroxy-16-(1-adamantyl)-5-cis-13-trans-ω-tetranorprostadienoate.

EXAMPLE 26

Dimethyl 2-Oxo-4-(1-Adamantyl)butylphosphonate (2b)

A solution of 24.8 g (0.200 moles) dimethyl methylphosphonate (Aldrich) in 250 ml dry tetrahydrofuran was cooled to −78° in a dry nitrogen atomsphere. To the stirred phosphonate solution was added 92 ml of 2.38 M n-butyllithium in hexane solution (Alfa Inorganics, Inc.) dropwise over a period of 30 minutes at such a rate that the reaction temperature never rose above −65°. After an additional 5 minutes stirring at −78°, 22.2 g (0.100 mole) methyl 3-(1-adamantyl)propionate was added dropwise at a rate that kept the reaction temperature less than −70° (20 minutes). After 1.0 hour at −78° the reaction mixture was allowed to warm to ambient temperature, neutralized with 55 ml acetic acid and rotary evaporated to a white gel. The gelatenous material was taken up to 50 ml water, the aqueous phase extracted with 100 ml portions of methylene chloride (4X), the combined organic extracts were backwashed with water (4 × 100 ml), dried (MgSO₄), and concentrated (water aspirator) to a crude residue and distilled, b.p. 195-200° (<0.02 mm) to give dimethyl 2-oxo-4-(1- adamantyl)butylphosphonate (2b) weighing 36.6 g (100% yield).

The nmr spectrum (CDCl₃) of the distilled product (2b) exhibited a doublet centered at 3.75 δ (6H; J=11 cps) for the OCH₃, a doublet centered at 3.08 δ (2H; J=23 cps) for COCH₂PO, a multiplet at 2.72–2.33 δ (2H) for the CH₂CO, a broad singlet at 2.05–1.75 δ (3H) for the CH, and multiplets at 1.75–1.17 δ (14H) for the remaining protons. The ir spectrum (CHCl₃) of 2b showed a strong adsorption at 1710 cm⁻¹ (carbonyl group).

EXAMPLE 27

2-(3α-p-Phenylbenzoyloxy-5α-hydroxy-2β-(3-oxo-5-(1-adamantyl)-trans-1-penten-1-yl)cyclopent-1α-yl)acetic acid, γ-lactone (3b)

Dimethyl 2-oxo-4-(1-adamantyl)butylphosphonate (2b) (6.88 g, 21.9 mmole) in 350 ml dry ether was treated with 8.6 ml. (20.3 mmole) 2.34 M n-butyllithium in n-hexane (Alfa Inorganics, Inc.) in a dry nitrogen atomosphere at room temperature. After 15 min. of stirring, the reaction mixture was cooled in an ice bath and a solution of 6.47 g (18.5 mmoles) of 2-(3α-p-phenylbenzoyloxy-5α-hydroxy-2β-formylcyclopent-1α-yl)acetic acid, γ-lactone in 70 ml. of dryl,-2-dimethoxyethane was added. After 1 hour at room temperature the reaction mixture was quenched with 2.0 ml glacial acetic acid, and concentrated. The resultant oil was dissolved in methylene chloride and was extracted with water (3 × 100 ml) and saturated brine (1x), was dried (MgSO₄) and concentrated to afford the crude solid 2-(3α-p-phenylbenzoyloxy-5α-hydroxy-2β-(3-oxo-5-(1adamantyl)-trans-1-penten-1-yl)cyclopent-1α-yl)acetic acid, γ-lactone (3b) which was recrystallized from ethanol as platelets weighing 6.06 g (61.0% yield) melting at 130°–132°.

The nmr spectrum (CDCl₃) of the crystalline 3b exhibited a multiplet at 8.16–7.20 δ (9H) for the aromatic protons, a multiplet at 6.90–5.96 δ (2H) for the olefinic protons, a multiplet at 5.47–4.82 δ (2H) for the CHO, and multiplets at 3.10–1.30 δ for the remaining protons. The ir spectrum (CHCl₃) of 3b exhibited strong adsorptions at 1770 cm⁻¹ (lactone carbonyl) and 1710 cm⁻¹ (ester carbonyl) and medium adsorptions at 1680 and 1620 cm⁻¹ (ketone carbonyl) and at 975 cm⁻¹ (trans olefin). Anal. for C₃₅H₃₈O₅ Calc. C, 78.04; H, 7.11; Found. C, 77.72; H, 7.21.

EXAMPLE 28

2-(3α-p-Phenylbenzoyloxy-5α-hydroxy-2β-(3α-hydroxy-5-(1-adamantyl)-trans-1-penten-1-yl)cyclopent-1α-yl)acetic acid, γ-lactone (5b) and 2-(3d-p-phenylbenzoyloxy-5α-hydroxy-2β-(3β-hydroxy-5-(1adamantyl)-trans-1-penten-1-yl)cyclopent-1γ-yl)acetic acid, γ-lactone (4b)

To a solution of 6.06 g (11.3 mmole) 2-(3α-p-phenylbenzoyloxy-5α-hydroxy-2β-(3-oxo-5-(1-adamantyl)-trans-1-penten-1-yl)cyclopent-1α-yl)acetic acid, γ-lactone (3b) in 50 ml dry tetrahydrofuran in a dry nitrogen atomsphere at ambient temperature was added dropwise 11.3 ml of a 0.5 M zinc borohydride solution. After stirring at room temperature for 1.0 hours, a saturated sodium bitartrate solution was added dropwise until hydrogen evolution ceased. The reaction mixture was allowed to stir for 5 minutes at which time 250 ml dry methylene chloride was added. After drying (MgSO₄) and concentrating (water apsirator) the resultant semi-solid was purified by column chromatography on silica gel (Baker "Analyzed" Reagent 60–200 mesh) using ether as eluent. After elution of less polar impurities a fraction containing 2.17 g (35.8% yield) 2-(3α-p-phenylbenzoyloxy-5α-hydroxy-2β-(3β-hydroxy-5-(1-adamantyl)-trans-1-penten-1-yl)cylopent-1α-yl)acetic acid, γ-lactone (5b) and a fraction containing 2.53 g (41.8% yield) of 2-(3α-p-phenyl-benzoyloxy-5α-hydroxy-2β-(3β-hydroxy-5-(1-adamantyl)-trans-1-penten-1-yl)cyclopent-1α-yl)acetic acid, lactone (4b) were collected.

The ir spectrum (CHCl₃) of 5 had strong adsorption at 1775 cm⁻¹ (lactone carbonyl) and 1715 cm⁻¹ (ester carbonyl) and a medium adsorption at 970 cm⁻¹ (trans olefin). The nmr spectrum (CDCl₃) of 5b exhibited a multiplet at 8.12–7.15 δ (9H) for the aromatic protons, a multiplet at 5.76–5.45 δ (2H) for the trans double bond, a multiplet at 5.45–4.81 δ (2H) for the CHOCO, a multiplet at 4.10–3.75 δ (1H) for the CHOH, and multiplets at 2.90–1.10 δ for the remaining protons. The ir and nmr spectra of 4 were superimposable on those of 5b.

EXAMPLE 29

2-(3α,5α-Dihydroxy-2β-(3α-hydroxy-5-(1-adamantyl)-trans-1-penten-1-yl)cyclopent-1α-yl)acetic acid, γ-lactone (6b)

A heterogeneous mixture of 2.17 g (4.02 mmole) of 2-(3α-p-phenylbenzoyloxy-5α-hydroxy-2β-(3α-hydroxy-5-(1-adamantyl)-trans-1-penten-1-yl)cyclopent-1α-yl)acetic acid, γ-lactone (5b), 25 ml. of absolute methanol, 10 ml. of dry tetrahydrofuran and 556 mg of finely powdered, anhydrous potassium carbonate was stirred at room temperature for 1.5 hour, then cooled to 0°. To the cooled solution was added 8.0 ml. (8.0 mmole) of 1.0 N aqueous hydrochloric acid. The solution was extracted with ethyl acetate (3x); the combined extracts were washed with saturated sodium bicarbonate (1x), were dried (MgSO₄), and concentrated to afford a crude semi-solid which was purified by silica gel column chromatography. After elution of less polar impurities with chloroform, elution with 5% methanol in methylene chloride afforded the desired 2-(3α,5α-dihydroxy-2β-(3α-hydroxy-5-(1-adamantyl)-trans-1-penten-1-yl)cyclopent-1α-yl)acetic acid, γ-lactone (6b), as a viscous, colorless oil weighing 1.34 g (92.6% yield).

The ir spectrum (CHCl₃) of 6b exhibited a strong adsorption at 1775 cm⁻¹ for the lactone carbonyl and medium adsorption at 975 cm⁻¹ for the trans-double bond. The nmr spectrum (CDCl₃) of 6b exhibited a multiplet at 5.61–5.37 δ (2H) for the olefinic protons, a multiplet at 5.07–4.74 δ (1H) for the CHOCO, a multiplet at 4.15–3.60 δ (2H) for the CHOH, and multiplets at 3.10–0.80 δ (27H) for the remaining protons.

EXAMPLE 30

2-(5α-Hydroxy-3α-(tetrahydrofuran-2-yloxy)-2β-(3α-(tetrahydropyran-2-yloxy)-5-(1-adamantyl)-trans-1-penten-1-yl)cyclopent-1α-yl)acetic acid, γ-lactone (7b)

To a solution of 1.34 g (3.69 mmole) 2-(3α,5α-dihydroxy-2β-(3α-hydroxy-5-(1-adamantyl)-trans-1-penten-yl)cyclopent-1α-yl)acetic acid, γ-lactone (6b) in 13 ml anhydrous methylene chloride and 1.34 ml of 2,3-dihyropyran at 0° in a dry nitrogen atomsphere was added 10 mg p-toluene-sulfonic acid, monohydrate. After stirring for 15 minutes, the reaction mixture was combined with 100 ml ether, the ether solution washed with saturated sodium bicarbonate (1 × 15 ml) then saturated brine (1 × 15 ml), dried (MgSO₄) and concentrated to yield 2.14 g (<100%) crude 2(5α-hydroxy-3α-(tetrahydropyran-2-yloxy)-2β-(3α-(tetrahydropyran-2-yloxy)-5-(1-adamantyl)-trans-1-penten-1-yl)cyclopent-1α-yl)acetic acid, γ-lactone (7b).

The ir spectrum (CHCl₃) had a strong adsorption at 1775 cm⁻¹ (lactone carbonyl) and a medium adsorption at 975 cm⁻¹ (trans olefin).

EXAMPLE 31

2-(5α-Hydroxy-3α-(tetrahydropyran-2-yloxy)-2β-(3α-(tetrahydropyran-2-yloxy)-5-(1-adamantyl)-trans-1-penten-1-yl) cyclopent-1α-yl)acetaldehyde, γhemiacetal (8b)

A solution of 1.95 g (3.69 mmole) 2-(5α-hydroxy-3α-(tetrahydropyran-2-yloxy)-2β-(3α-(tetrahydropyran-2-yloxy)-5-(1-adamantyl)-trans-1-penten-1-yl)cyclopent-1α-yl)acetic acid, γ-lactone (7b) in 20 ml dry toluene was cooled to −78° in a dry nitrogen atmosphere. To this cooled solution was added 5.0 ml of 20% diisobutylaluminum hydride in n-hexane (Alfa Inorganics) dropwise at such a rate so that the internal temperature never rose above −65° (15 minutes). After an additional 30 minutes of stirring at −78°, anhydrous methanol was added until gas evolution ceased and the reaction mixture was allowed to warm to room temperature. The reaction mixture was combined with 150 ml ether, washed with 50% sodium potassium tartrate solution (3 × 50 ml), dried (MgSO₄) and concentrated to afford the crude 2-(5α-hydroxy-3α-(tetrahydropyran-2-yloxy)-2β-(3α-(tetrahydropyran-2-yloxy)-5-(1-adamantyl)-trans-1-penten-1-yl)cyclopent-1α-yl)acetaldehyde, γ-hemiacetal (8b) which was purified by silica gel column chromatography using mixtures of benzene: ethyl acetate as eluents. After elution of less polar impurities, the purified product 8b was collected as a viscous, colorless oil weighing 1.65 g (84.6% yield).

The ir spectrum (CHCl₃) of 8b had no adsorption for a carbonyl group and a medium adsorption at 975 cm⁻¹ for the trans double bond.

The product of this reaction is converted to 17-(1-adamantyl)-ω-trisnorprostaglandin tetrazoles, carboximides and sulfonimides of the A, E, or F series via the procedures of examples 103–110, 140–141, 156–165 and 169–170.

EXAMPLE 32

9α-Hydroxy-11α,15α-bis-(tetrahydropyran-2-yloxy)-17-(1-adamantyl)-cis-5-trans-13-ω-trisnorprostadienoic acid (9b)

To a solution of 4.14 g (9.34 mmole) (4-carbohydroxy-n-butyl)triphenylphosphonium bromide in a dry nitrogen atmosphere in 8.0 ml dry dimethyl sulfoxide was added 9.17 ml (18.2 mmole) of a 1.98 M solution of sodium methylsulfinylmethide in dimethyl sulfoxide. To this red ylide solution was added dropwise a solution of 1.65 g (3.12 mmole) 2-(5α-hydroxy-3α-(tetrahydropyran-2-yloxy)-2β-(3α-(tetrahydropyran-2-yloxy)-5-(1-adamantyl)-trans-1-penten-1-yl)cyclopent-1α-yl)acetaldehyde, γ-hemiacetal (8b) in 6.0 ml dry dimethyl sulfoxide over a period of 20 minutes. After an additional 18.0 hours stirring at room temperature, the reaction mixture was poured onto ice water. The basic aqueous solution was acidified to pH~3 with 10% aqueous hydrochloric acid. The acid solution was extracted with ethyl acetate (3 × 50 ml) and the combined organic extracts washed once with water (10 ml), dried (MgSO₄) and evaporated to a solid residue which was purified by column chromatography on silica gel (Baker "Analyzed" Reagent 60–200 mesh) using mixtures of chloroform ethyl acetate as eluent. After removal of high R_f impurities, 188 g (98.3% yield) of 9α-hydroxy-11α,15α-bis-tetrahydropyran-2-yloxy)-17-(1α-adamantyl)-cis-5-trans-13-ω-trisnorprostadienoic acid (9b) was collected.

The ir spectrum (CHCl₃) of 9b had a strong adsorption at 1710 cm⁻¹ (acid carbonyl) and a medium adsorption at 970 cm⁻¹ (trans olefin). The nmr spectrum (CDCl₃) exhibited a broad singlet at 6.78-6.20 δ (2H) for the OH, a multiplet at 5.71-5.16 δ (4H) for the olefinic protons, a singlet at 4.75-4.50 δ (2H) for the OCHO, multiplets at 4.19-3.19 δ (7H) for the CH₂O and CHO, and multiplets at 2.51-0.76 δ for the remaining protons.

EXAMPLE 33

9-oxo-11α,15α-bis-(tetrahydropyran-2-yloxy)-17-(1-adamantyl)-cis-5-trans-13-ω-trisnorprostadienoic acid (10b):

To a solution cooled to −10° under nitrogen of 1.11 g (1.82 mmole) 9α-hydroxy-11A,15α-bis-(tetrahydropyran-2-yloxy)-17-(1-adamantyl)-cis-5-trans-13-ω-trisnorprostadienoic acid (9b) in 32 ml reagent grade acetone was added dropwise to 1.63 ml of Jones' reagent. After 15 minutes at −10°, 1.63 ml 2-propanol was added and the reaction mixture was allowed to stir an additional 5 minutes at which time it was combined with 100 ml ethyl acetate, washed with water (3 × 10 ml), dried (MgSO₄) and concentrated to give 1.11 g of 9-oxo-11α,15α-bis-(tetrahydropyran-2-yloxy)-17-(1-adamantyl)-cis-5-trans-13-ω-trisnorprostadienoic acid (10b) which was used without purification.

EXAMPLE 34

9-Oxo-11α,15α-dihydroxy-17-(1-adamantyl)-cis-5-trans-13-ω-trisnorprostadienoic acid (11b)

A solution of 1.11 g (1.82 mmole) 9-oxo-11α,15α-bis-tetrahydropyran-2-yloxy)-17-(1-adamantyl)-cis-5-trans-13-ω-trisnorprostadienoic acid (10b) in 11 ml of a 65:35 mixture of glacial acetic acid:water and 1.0 ml of tetrahydrofuren was stirred under nitrogen at room temperature for 18 hours then was concentrated by rotary evaporation. The resulant crude oil was purified by column chromatography on silica gel (Mallinckrodt CC-7 100–200 mesh) using mixtures of chloroform: ethyl acetate as eluents. After elution of less polar impurities the viscous, colorless 9-oxo-11α,15α-dihydroxy-17-(1-adamantyl)-cis-5-trans-13-ω-trisnorprostadienoic acid (11) weighing 408 mg was collected.

The ir spectrum (CHCl₃) of 11b had strong adsorptions at 1700 cm⁻¹ (acid carbonyl) and 1735 cm⁻¹ (ketone carbonyl) and a medium adsorption at 970 cm⁻¹ (trans olefin). The nmr spectrum (CDCl₃) of 11b exhibited a singlet at 5.95 δ (3H) for the OH, a multiplet at 5.73-5.92 δ (2H) for the trans olefin, a multiplet at 5.52-5.24 δ (2H) for the cis olefin, a multiplet at 4.31-3.80 δ (2H) for the CHO, and multiplets at 2.72-0.76 δ for the remaining protons.

EXAMPLE 35

9α,11α,15α-Trihydroxy-17-(1-adamantyl)-cis-5-trans-13-ω-trisnorprostadienoic acid (12b)

A solution of 627 mg of 9α-hydroxy-11α,15α-bis-(tetrahydropyran-2-yloxy)-17-(1-adamantyl)-cis-5-trans-13-ω-trisnorprostadienoic acid (9b) in 7 ml of a 65:35 mixture of glacial acetic acid:water and 0.5 ml of tetrahydrofuran was stirred under nitrogen at room temperature for 18 hours, then was concentrated by rotary evaporation. The resultant crude oil was purified by silica gel column chromatography (Mallinckrodt CC-7) using mixtures of chloroform: ethyl acetate as eluents. After removal of less polar impurities the white, crystalline 9α,11α,15α-trihydroxy-17-(1-adamantyl)-cis-5-trans-13-ω-trisnorprostadienoic acid (12b) was collected weighing 347 mg and melting at 133.5°–135° (from ethanol:hexane).

The ir spectrum (KBr) of 12b had a strong adsorption at 5.84 μ (acid carbonyl) and a medium adsorption at 10.25 μ (trans olefin). The nmr spectrum (CD$_3$OD) of 12b exhibited a multiplet at 5.60–5.30 δ (4H) for the olefinic protons, a multiplet at 4.20–3.66 δ (3H) for the CHO, and multiplets at 2.49–0.80δ for the remaining protons.

EXAMPLE 36

2-(3α,5α-Dihydroxy-2β-(3β-hydroxy-5-(1-adamantyl)-trans-1-penten-1-yl)cyclopent-1α-yl)acetic acid, γ-lactone (6'b)

A heterogeneous mixture of 2.53 g (4.68 mmole) of 2-(3α-p-phenylbenzoyloxy-5α-hydroxy-2β-(3β-hydroxy-5-(1-adamantyl)-trans-1-penten-1-yl)cyclopent-1α-yl)acetic acid, γ-lactone (4b), 25 ml of absolute methanol, 10 ml of dry tetrahydrofuran and 646 mg of finely powdered, anhydrous potassium carbonate was stirred at room temperature for 1.5 hour, then cooled to 0°. To the cooled solution was added 9.3 ml (9.3 mmole) of 1.10 N aqueous hydrochloric acid. The solution was extracted with ethyl acetate (3x); the combined extracts were washed with saturated sodium bicarbonate (1x), were dried (MgSO$_4$), and concentrated to afford a crude semi-solid which was purified by silica gel column chromatography. After elution of less polar impurities with chloroform, elution with 5% methanol in methylene chloride afforded the desired 2-(3α,5α-dihydroxy-2β-hydroxy-5-(1-adamantyl)-trans-1-penten-1-yl)cyclopent-1α-yl)acetic acid, γ-lactone (6'b), as a viscous, colorless oil weighing 1.34 g (79.6% yield).

The ir spectrum (CHCl$_3$) exhibited a strong adsorption at 1775 cm$^{-1}$ for the lactone carbonyl and medium adsorption at 975 cm$^{-1}$ for the trans-double bond. The nmr spectrum (CDCl$_3$) of 6'b exhibited a multiplet at 5.61–5.37 δ (2H) for the olefinic protons, a multiplet at 5.07–4.74 δ (1H) for the CHOCO, a multiplet at 4.15–3.60 δ (2H) for the CHOC, and multiplets at 3.10–0.80 δ (27H) for the remaining protons.

EXAMPLE 37

2-(5α-Hydroxy-3α-(tetrahydropyran-2-yloxy)-2β-(3β-tetrahydropyran-2-yloxy(-5-(1-adamantyl)-trans-1-pentene-1-yl)cyclopent-1α-yl)acetic acid, γ-lactone (7'b)

To a solution of 1.34 g (3.69 mmole) of 2-(3α,5α-dihydroxy-2β-(3α-hydroxy-5-(1-adamantyl)-trans-1-penten-1-yl)cyclcopent-1α-yl)acetic acid, γ-lactone (6'b) in 13 ml anhydrous methylene chloride and 1.34 ml of 2,3-dihydropyran at 0° in a dry nitrogen atmosphere was added 8 mg p-toluenesulfonic acid, monohydrate. After stirring for 15 minutes, the reaction mixture was combined with 100 ml ether, the ether solution washed with saturated sodium bicarbonate (1 × 15 ml) then saturated brine (1 × 15 m), dried (MgSO$_4$) and concentrated to yield 2.20 g (>100%) crude 2-(5α-hydroxy-33α-(tetrahydropyran-2-yloxy)-2β-(3β-(tetrahydropyran-2-yloxy)-5-(1-adamantyl)trans-1-penten-1-yl)cyclopent-1α-yl)acetic acid, γ-lactone (7'b).

The ir spectrum (CHCl$_3$) had a strong adsorption at 1775 cm$^{-1}$ (lactone carbonyl) and a medium adsorption at 975 cm$^{-1}$ (trans olefin).

EXAMPLE 38

2-(5α-Hydroxy-3α-(tetrahydropyran-2-yloxy)-2β-(3β-(tetrahydropyran-2-yloxy)-5-(1-adamantyl)-trans-1-penten-1-yl)cyclopent-1α-yl)acetaldehyde, γ-hemiacetal (8'b)

A solution of 1.95 g (3.69 mmole) 2-(5α-hydroxy-3α-(tetrahydropyran-2-yloxy)-2β-(3β-(tetrahydropyran-2-yloxy)-5-(1-adamantyl)-trans-1-penten-1-yl)cyclopent-1α-yl)acetic acid, γ-lactone (7'b) in 20 ml dry toluene was cooled to −78° in a dry nitrogen atmosphere. To this cooled solution was added 5.0 ml of 20% diisobutylaluminum hydride in n-hexane (Alfa Inorganics) dropwise at such a rate so that the internal temperature never rose above −65° (15 minutes). After an additional 30 minutes of stirring at −78°, anhydrous methanol was added until gas evolution ceased and the reaction mixture was allowed to warm to room temperature. The reaction mixture was combined with 100 ml ether, washed with 50% sodium potassium tartrate solution (4 × 20 ml), dried (MgSO$_4$) and concentrated to afford the crude 2-(5α-hydroxy-3α-(tetrahydropyran-2-yloxy)-2β-(3β-(tetrahydropyran-2-yloxy)-5-(1-adamantyl)-trans-1-penten-1-yl) cyclopent-1α-yl)acetaldehyde, γ-hemiacetal (8'b) which was purified by silica gel column chromatography using mixtures of benzene:ethyl acetate as eluents. After elution of less polar impurities, the purified product (8'b) was collected as a viscous, colorless oil weighing 1.66 g (85.0% yield).

The ir spectrum (CHCl$_3$) of 8'b had no adsorption for a carbonyl group and a medium adsorption at 975 cm$^{-1}$ for the trans-double bond.

The product of this reaction is converted to 15-epi-17-1-adamantyl)-ω-trisnorprostaglandin tetrazoles, carboximides and sulfonimides of the A, E or F series via the procedures of examples 103–110, 140–141, 156–165 and 169–170.

EXAMPLE 39

9α-Hydroxy-11α,15β-bis-(tetrahydropyran-2-yloxy)-17-(1-adamantyl)-cis-5-trans-13-ω-trisnorprostadienoic acid (9'b)

To a solution of 4.14 g (9.34 mmole) (4-carbohydroxy-n-butyl)triphenylphosphonium bromide in a dry nitrogen atmosphere in 8.0 ml dry dimethyl sulfoxide was added 9.17 ml (18.2 mmole) of a 1.98 M solution of sodium methylsufinylmethide in dimethyl sulfoxide. To this red ylide solution was added dropwise a solution of 1.66 g (3.12 mmole) 2-(5α-hydroxy-3α-(tetrahydropyran-2-yloxy)-2β-(3β-(tetrahydropyran-2-yloxy)-5-(1-adamantyl)-trans-1-penten-1-yl) cyclopent-1α-yl)acetaldehyde, γ-hemiacetal (8'b) in 6.0 ml dry dimethyl sulfoxide over a period of 20 minutes. After an additional 18.0 hours stirring at room temperature, the reaction mixture was poured onto ice water. The basic aqueous solution was acidified to pH~3 with 10% aqueous hydrochloric acid. The acidic solution was extracted with ethyl acetate (3 × 100 ml) and the combined organic extracts washed once with water (10 ml), dried (MgSO$_4$) and evaporated to a solid residue which was purified by column chromatography on silica gel (Baker "Analyzed" reagent 60–200 mesh) using mixtures of chloroform ethyl acetate as eluents. After removal of high R$_f$ impurities, 1.99 g (>100% yield) of 9α-hydroxy-11α,15β-bis-(tetrahydropyran-2-yloxy)-17-(1-adamantyl)-cis-5-trans-13-ω-trisnorprostadienoic acid (9'b) was collected.

The ir spectrum (CHCl$_3$) of (9'b) had a strong adsorption at 1710 cm$^{-1}$ (acid carbonyl) and a medium adsorption at 970 cm$^{-1}$ (trans olefin). The nmr spectrum (CDCl$_3$) exhibited a broad singlet at 6.78–6.20 δ (2H) for the OH, a multiplet at 5.71–5.16 δ (4H) for the olefinic protons, a singlet at 4.75–4.50 δ (2H) for the OCHO, multiplets at 4.19–3.19 δ (7H) for the CH$_2$O and CHO, and multiplets at 2.51–0.76 δ for the remaining protons.

EXAMPLE 40

9-Oxo-11α,15β-bis-(tetrahydropyran-2-yloxy)-17-(1-adamantyl)cis-5-trans-13-ω-trisnorprostadienoic acid (10'b):

To a solution cooled to −10° under nitrogen of 1.24 g (2.02 mmole) 9α-hydroxy-11α,15β-bis-(tetrahydropyran-2-yloxy)-17-(1-adamantyl)-cis-5-trans-13-ω-trisnorprostadienoic acid (9'b) in 36 ml. reagent grade acetone was added dropwise to 1.80 ml. of Jones' reagent. After 15 minutes at −10°, 1.80 ml 2-propanol was added and the reaction mixture was allowed to stir an additional 5 minutes at which time it was combined with 100 ml ethyl acetate, washed with water (3 × 10 ml), dried (MgSO$_4$) and concentrated to give 1.18 g of 9-oxo-11α,15β-bis-(tetrahydropyran-2-yloxy)-17-(1-adamantyl)-cis-5-trans-13-ω-trisnorprostadienoic acid (10'b) which was used without purification.

EXAMPLE 41

9-Oxo-11α,15β-dihydroxy-17-(1-adamantyl)-cis-5-trans-13-ω-trisnorprostadienoic acid (11'b)

A solution of 1.18 g (1.93 mmole) 9-oxo-11α,15β-bis-(tetrahydropyran-2-yloxy)-17-(1-adamantyl)-cis-5-trans-13-ω-trinorprostadienoic acid (10'b) in 11 ml of a 65:35 mixture of glacial acetic acid: water and 1.0 ml of tetrahydrofuran was stirred under nitrogen at room temperature for 18 hours then was concentrated by rotary evaporation. The resultant crude oil was purified by column chromatography on silica gel (Mallinckrodt CC-7 100–200 mesh) using mixtures of chloroform:ethyl acetate as eluent. After elution of less polar impurities the viscous, colorless 9-oxo-11α,15β-dihydroxy-17-(1-adamantyl)-cis-5-trans-13-ω-trinorprostadienoic acid (11'b) weighing 429 mg (50% yield) was collected.

The ir spectrum (CHCl$_3$) of 11'b had strong adsorptions at 1770 cm$^{-1}$ (acid carbonyl) and 1735 cm$^{-1}$ (ketone carbonyl) and a medium adsorption at 970 cm$^{-1}$ (trans olefin). The nmr spectrum (CDCl$_3$) of 11'b exhibited a singlet at 5.95 δ (2H) for the OH, a multiplet at 5.73–5.52 δ (2H) for the trans olefin, a multiplet at 5.52–5.24 δ (2H) for the cis olefin, a multiplet at 4.31–3.80 δ (2H) for the CHO, and multiplets at 2.72–0.76 δ for the remaining protons.

EXAMPLE 42

9α-11α,15β-Trihydroxy-17-(1-adamantyl)-cis-5-trans-13-ω-trisnorprostadienoic acid (12'b)

A solution of 664 mg of 9α-hydroxy-11α,15β-bis-(tetrahydropyran-2-yloxy)-17-(1-adamantyl)-cis-5-trans-13-ω-trisnorprostadienoic acid (9'b) in 7 ml of a 65:35 mixture of glacial acetic acid: water and 0.5 ml of tetrahydrofuran was stirred under nitrogen at room temperature for 18 hours, then was concentrated by rotary evaporation. The resultant crude oil was purified by silica gel (Mallinckrodt CC-7) chromatography using mixtures of chloroform: ethyl acetate as eluents. After removal of less polar impurities the 9α,11α,15β-trihydroxy-17-(1-adamantyl)-cis-5-trans-13-ω-trisnorprostadienoic acid (12'b) weighing 295 mg was collected as a viscous oil.

The ir spectrum (CHCl$_3$) of (12'b) had a strong adsorption at 1710 cm$^{-1}$ (acid carbonyl) and a medium adsorption at 970 cm$^{-1}$ (trans olefin). The nmr spectrum (CDCl$_3$) of (12'b) exhibited a multiplet at 5.69–5.30 δ (4H) for the olefinic protons, a singlet at 5.10 δ (4H) for the OH, a multiplet at 4.36–3.80 δ (3H) for the CHOH, and multiplets at 2.56–0.70 δ for the remaining protons.

EXAMPLE 43

2-[3α-p-Phenylbenzoyloxy-5α-hydroxy-2β-(3α-hydroxy-3β-methyl-5-(1-adamantyl)-trans-1-penten-1-yl)cyclopent-1α-yl]acetic acid, γ-lactone (13b) and 2-[3α-p-phenylbenzoyloxy-5α-hydroxy-2β-(3β-hydroxy-3α-methyl-5-(1-adamantyl)-trans-1-penten-1-yl)cyclopent-1α-yl]acetic acid, γ-lactone (14b)

To a solution of 2.15 g (4.0 mmoles) of 2-[3α-p-phenylbenzoyloxy-5α-hydroxy-2β-(3-oxo-5-(1-adamantyl)-trans-1-penten-1-yl)cyclopent-1α-yl]acetic acid, γ-lactone (3b) in 21 ml of anhydrous ether and 20 ml of tetrahydrofuran in a dry nitrogen atmosphere at −78° is added dropwise 4.0 ml of a (1.0M) solution of methylithium in ether (Alfa). After stirring at −78° for 15 minutes the reaction is quenched by the addition of glacial acetic acid until the pH of the mixture is approximately 7. The mixture is then diluted with methylene chloride and the diluted organic solution is washed with water and saturated brine, is dried (anhydrous magnesium sulfate), and is concentrated to afford the epimeric alcohols.

The crude product is purified by column chromatography on silica gel to provide the 2-[3α-p-phenylbenzoloxy-5α-hydroxy-2β-(3α-hydroxy-3β-methyl-5-(1-adamantyl)-trans-1-penten-1-yl)cyclopent-1α-yl]acetic acid, γ-lactone (13b) and the 2-[3α-p-phenylbenoyloxy-5α-hydroxy-2β-(3β-hydroxy-3α-methyl-5-(1-adamantyl)-trans-1-penten-1-yl)cyclopent-1α-yl]acetic acid, γ-lactone (14b).

The products of this example (13b) and (14b) are converted to 15 methyl-13,14-dihydro-17-(1-adamantyl)-ω-trisnorprostaglandins via the procedures of examples 29–42. Other 15-lower alkyl analogs precursers are prepared as above from the appropriate lactone starting materials and the desired lower alkyl group is introduced by substituting the necessary lower alkyl lithium reagent for methyl lithium in the above example.

EXAMPLE 44

9-oxo-11α,15α-dihydroxy-15β-methyl-18-(1-adamentyl)-5-cis-13-trans-ω-bisnorprostadienoic acid (13c).

To a solution of 300 mg 9α,11α,15α-trihydroxy-18-(1-adamantyl-5-cis-13-trans-ω-bisnorprostadienoic acid (12c) in 15 ml of dioxane under nitrogen and warmed to 50° is added 220 mg of 2,3-dichloro-5,6-dicyano-1,4-benzoquinine. The mixture is stirred at 45°–50° overnight under nitrogen, is let cool, and is filtered through Celite. The filtrate is diluted with methylene chloride, is washed with saturated brine, is dried (anhydrous magnesium sulfate), and is concentrated by rotary evaporation. Purification of the crude product by silica gel chromatography affords 9α,11α-dihydroxy-15-oxo-18-(1-adamantyl)-5-cis-13-trans-ω-bisnorprostadienoic acid (II).

The above 15-keto-PGF$_{2\alpha}$ compound (550 mg) is dissolved in dry tetrahydrofuran (50ml) and is treated with 1,1,1,3,3,3-hexamethyldisilazane (6 ml) and trimethylchlorosilane (1 ml) at room temperature for 18 hours under nitrogen, then is diluted with xylene. The mixture is filtered, and is concentrated to afford the desired trimethylsilyl derivative of 9α,11α-dihydroxy-15-oxo-18-(1-adamantyl)-5-cis-13-trans-ω-bisnoreprostadienoic acid.

A solution cooled to −45° of 160 mg (0.35 mmole) of the 9α,11α,15α-trihydroxy-15β-methyl-18-(1-adamantyl)-5-cis-13-trans-ω-bisnorprostadienoic acid prepared above in 2 ml of acetone and 128 mg (0.9 mmole) of trimethylsilyldiethylamine is stirred under nitrogen for 24 hours, then is concentrated. The crude residue is dissolved in 2.0 ml of dry methylene chloride and 3.5 ml (0.35 mmole) of a 0.1M solution of Collin's reagent in methylene chloride is added. The resultant black solution is stirred for 15 minutes at room temperature, then is filtered through a column of silica gel. Concentration of the eluent affords a crude residue which, without purification, is dissolved in 2 ml of a 65:35 mixture of acetic acid: water. After being stirred for 3 hours at room temperature the solution is concentrated. Purification of the crude residue by column chromatography provides the 9-oxo-11α,15α-dihydroxy-15β-methyl-18-(1-adamantyl)-5-cis-13-trans-ω-bisnorprostadienoic acid (13c).

The other 15 lower alkyl prostaglandin analogs of this invention are prepared according to this procedure by the substitution of the desired grignard reagent corresponding to the lower alkyl desired and by the substitution of the appropriate prostaglandin of the F series in the place of 12c.

To a solution of the trimethylsilyl drivative from above (350 mg) in anhydrous ether (35 ml) is added dropwise 1.5 ml of a 3M solution of methyl magnesium bromide in ether. The mixture is stirred for 1.0 hour then is quenched by pouring into 100 ml of saturated aqueous ammonium chloride. The aqueous layer is extracted with ether (2x), and the combined organic extracts is washed with saturated brine, is dried (anhydrous magnesium sulfate), and is concentrated by rotary evaporation. The residue is dissolved in a 65:35 mixture of acetic acid: water. After being stirred for 5 hours at room temperature, the solution is concentrated. Purification of the crude product by column chromatography affords 9α,11α,15β-trihydroxy-15α-methyl-18-(1-adamantyl)-5-cis-13-trans-ω-bisnorprostadienoic acid epi III and 9α,11α,15α-trihydroxy-15β-methyl-18-(1-adamantyl)-5-cis-13-trans-ω-bisnorprostadienoic acid (III).

EXAMPLE 45

Following the procedure of examples 7 and 8 precursors to the 13,14-dihydro series of prostaglandin analogs of this invention may be prepared from the appropriate γ-lactones of type 3. These γ-lactones are prepared via the procedures of examples 1 and 2. The conversion of these precursors to the final prostaglandins is via the procedures of examples 61–66 and 77.

EXAMPLE 46

9-oxo-15α-hydroxy-18-(1-adamantyl)-$\Delta^{10,11}$-5-cis-13-trans-ω-bisnorprostatrienoic acid (15c)

A solution of 75 mg of 9-oxo-11α,15α-dihydroxy-18-(1-adamantyl)-5-cis-13-trans-ω-bisnorprostadienoic acid (11c), 15 ml of dry methylene chloride and 15 ml of formic acid is stirred at room temperature for 7 hours. The reaction mixture is then diluted with xylene and concentrated to afford (after chromatographic purification) 9-oxo-15α-hydroxy-18-(1-adamantyl)-$\Delta^{10,11}$-5-cis-13-trans-ω-bisnorprostatrienoic acid (15c).

EXAMPLE 47

9-oxo-11α,15β-dihydroxy-17-(1-adamantyl)-13-trans-ω-trisnorprostenoic acid (29b):

A solution of 58 mg 9-oxo-11α,15β-dihydroxy-17-(1-adamntyl)-5-cis-13-trans-ω-tetranorprostadienoic acid (11b) in 6 ml of anhydrous ether is treated with 448 mg (3.6 mmole) dimethyl isopropyl chlorosilane and 36.0 mg (3.6 moles) triethylamine at 25° for 48 hours. The reaction mixture is cooled to 0°, methanol is added and the resulting solution is washed with water, is dried (anhydrous magnesium sulfate), and is concentrated. The residue is dissolved in methanol (6 ml), 5% palladium in carbon (30 mg) is added, and the resultant slurry is hydrogenated for 4 hours at −22°. After filtration (Celite) and concentration of the filtrate, the product is hydrolyzed in 2 ml of a 65:35 mixture of acetic acid: water for 10 minutes, is diluted with water, and is extracted with ethyl acetate. The combined organic extracts are washed with brine, dried (anhydrous magnesium sulfate), and concentrated to afford 9-oxo-11α,15β-dihydroxy-17-(1-adamantyl)-13-trans-ω-trisnorprostenoic acid (29b) after purification by silica gel chromatography.

EXAMPLE 48

2-[3α-p-Phenylbenzoyloxy-5α-hydroxy-2β-(3α-hydroxy-3-(1-adamantyl)-prop-1-yl)cyclopent-1α-yl]acetic acid, γ-lactone (19f) and
2-[3α-p-phenylbenzoyloxy-5α-hydroxy-2β-(3β-hydroxy-3-(1-adamantyl)-prop-1-yl)cyclopent-1α-yl]acetic acid, γ-lactone (19′f)

A solution of 5.10 g (10 mmoles) of 2 -[3α-p-phenylbenzoyloxy-5α-hydroxy-2β-(3-oxo-3-(1-adamantyl)-trans-1-propen-1-yl)cyclopent-1α-yl]acetic acid, γ-lactone (3f) and 0.510 g of 5% palladium on carbon in 50 ml of methanol is stirred under 1 atmosphere of hydrogen for 8 hours. The mixture is then filtered (Celite) and concentrated to afford 2-[3α-p-phenylbenzoloxy-5α-hydroxy-2β-(3-oxo-3-(1-adamantyl)-prop-1-yl)cyclopent-1α-yl]acetic acid, γ-lactone.

To a solution of 4.07 g (8.0 mmoles) of crude hydrogenation product prepared above in 40 ml of methanol is added 152 mg (4.0 mmoles) of sodium borohydride. The solution is stirred at room temperature for 2 hours then is concentrated. The residue is diluted with 0.1N hydrochloric acid and the aqueous layer is extracted with ethyl acetate (4x). The combined organic extracts are washed with saturated brine (1x), are dried (anhydrous magnesium sulfate), and are concentrated. Purification of the crude residue by silica gel chromatography affords 2-[3α-p-phenylbenzoyloxy-5α-hydroxy-2β-(3α-hydroxy-3-(1-adamantyl)-prop-1-yl) cyclopent-1α-yl]acetic acid, γ-lactone (19f) and 2-[3α-p-phenylbenzoloxy- 5α-hydroxy-2β-(3β-hydroxy-3-(1-adamantyl)-prop-1-yl) cyclopent-1α-yl] acetic acid, γ-lactone (19'f).

The products of this example may be converted to the corresponding 15-(1-adamantyl)-13,14-dihydro-ω-pentanorprostaglandins via the procedure of examples 29 –43.

EXAMPLE 49

2-[5α-Hydroxy-3α-(tetrahydropyran-2-yloxy)-2β-(3α-tetrahydropyran-2-yloxy)-8-(1-adamantyl)-oct-1-yl)cyclopent-1α]acetic acid, γ-lactone (24e)

A heterogeneous mixture of 2.39 g. (4.2 mmoles) 2-[5α-hydroxy-3α-(tetrahydropyran-2-yloxy)-2β-(3α-(tetrahydropyran-2-yloxy)-8-(1-adamantyl)-trans-1-octen-1-yl)cyclopent-1α-yl]acetic acid, γ-lactone (7e) and 239 mg. of 5% palladium in carbon in 25 ml. of absolute methanol is stirred under 1 atmosphere of hydrogen for 2 hours. The reaction mixture is filtered (Celite) and cencentrated to provide 2-[5α-hydroxy-3α-(tetrahydropyran-2-yloxy)-2β-(3α-(tetrahydropyran-2-yloxy)-8-(1-adamantyl)oct-1-yl) cyclopent-1α-yl]acetic acid, γ-lactone (24e).

This product is transformed into 13,14 dihydro-20-(1-adamantyl)-prostaglandins of the A, E or F series via the procedures of examples 29–43.

EXAMPLE 50

9β,11α,15α-Trihydroxy-17-(1-adamantyl)-5-cis-13-trans-ω-trisnorprostadienoic acid tris-hydroxymethylamino methane salt To a solution of 319 mg (0.70 mmole) of 9β,11α,15α-trihydroxy-17-(1-adamantyl)-5-cis-13-trans-107-trisnorprostadienoic acid (12b) in 35 ml of dry acetonitrile, heated at 80°, is added with vigorous stirring a solution of 86 mg (0.68 mmole) of tris-hydroxymethylamino methane in 0.15 ml of water. The mixture is allowed to cool at room temperature and the 9β,11α,15α-trihydroxy-17-(1-adamantyl)-5-cis-13-trans-ω-trisnorprostadienoic acid tris-hydroxymethylamino methane salt is collected.

EXAMPLE 51

Phenethyl 9α,11α,15α-trihydroxy-19-(1-adamantyl)-5-cis-13-trans-ω-norprostadienoate To a solution of 31 mg of 9α,11α,15α-trihydroxy-19-(1-adamantyl)-5-cis-13-trans-ω-norprostadienoic acid (12d) in 5 ml of ether is added a yellow solution of 1-diazo-2-phenylethane (prepared by oxidation of phenethyl hydrazine) dropwise until the yellow color persists for 5 minutes. Concentration of the solution and silica gel chromatographic purification of the crude residue affords phenethyl 9α,11α,15α-trihydroxy-19-(1-adamantyl)-5-cis-13-trans-ω-norprostadienoate.

EXAMPLE 52

Dodecyl 9α,11α,15α-trihydroxy-19-(1-adamantyl)-5-cis-13-trans-ω-norprostadienoate To a solution of 31 mg of 9α,11α,15α-trihydroxy-19-(1-adamantyl)-5-cis-13-trans-ω-norprostadienoic acid (12d) in 5 ml of ether is added a yellow solution of diazododecane (prepared by oxidation of dodecyl hydrazine) dropwise until the yellow color persists for 5 minutes. Concentration of the solution and silica gel chromatographic purification of the crude residue affords dodecyl 9α,11α,15α-trihydroxy-19-(1-adamantyl)-5-cis-13-trans-ω-norprostadienoate.

EXAMPLE 53

Methyl 9α,11α,15α-trihydroxy-18-(1-adamantyl)-5-cis-13-trans-ω-bisnorprostadienoate To a solution of 75 mg of 9α,11α,15α-trihydroxy-18-(1-adamantyl)-5-cis-13-trans-ω-bisnorprostadienoic acid (12c) in 10 ml of ether is added a yellow solution of diazomethane in ether (prepared from N-methyl-N'nitro-N-nitrosoguanidine) dropwise until the yellow color persists for 5 minutes. Concentration of the solution and silica gel chromatographic purification of the crude residue affords methyl 9α,11α,15α-trihydroxy-18-(1-adamantyl)-5-cis-13-trans-ω-bisnorprostadienoate.

EXAMPLE 54

Cyclooctyl 9α,11α,15α-trihydroxy-17-(1-adamantyl)-5-cis-13-trans-ω-trisnorprostadienoate To a solution of 130 mg (0.30 mmole) of 9α,11α,15α-trihydroxy-17-(1-adamantyl)-5-cis-13-trans-ω-trisnorprostadienoic acid (12b) in 7 ml of dry methylene chloride is added 33 mg (0.33 mmole) of triethyl amine. The mixture is stirred for 5 minutes then 36 mg (0.33 mmole) pivaloyl chloride is added. The solution is stirred for 45 minutes at room temperature under nitrogen then 192 mg (1.5 mmole) of cyclooctyl alcohol and 225 μl of pyridine are added. The mixture is stirred at room temperature for an additional 2.0 hours then is diluted with ethyl acetate. The diluted solution is washed with water (2x) and saturated brine (1x), is dried (anhydrous magnesium sulfate), and is concentrated. Purification of the crude residue by silica gel chromatography provides the cyclooctyl 9α,11α,15α-trihydroxy-17-(1-admantyl)-5-cis-13-trans-ω-trisnorprostadienoate.

EXAMPLE 55

2-phenylethyl 9α,11α,15α-Trihydroxy-18-(1-adamantyl)-5-cis-13-trans-ω-bisnorprostadienoate To a solution of 99 mg (0.21 mmole) of 9α,11α,15α-trihydroxy-18-(1-adamantyl)-5-cis-13-trans-ω-bisnorprostadienoic acid (12c) and 257 mg (2.1 mmoles) of 2-phenylethanol in 10 ml of dry methylene chloride is added 2.5 ml (0.25 mmole) of a 0.1M solution of dicyclohexylcarbodiimide in methylene chloride. The solution is stirred under nitrogen at room temperature overnight then is concentrated. The crude product is purified by silica gel column chromatography. After removal of the excess 2-phenylethanol with chloroform, elution with ethyl acetate affords the 2-phenylethyl 9α,11α,15α-trihydroxy-18-(1-adamantyl)-5-cis-13-trans-ω-bisnorprostadienoate.

EXAMPLE 56

17-(1-adamantyl)-ω-trisnorprostaglandin $F_{2\beta}$

To a solution under nitrogen cooled in ice of 100 mg (0.225 mmole) of 17-(1-adamantyl)-ω-trisnorprostaglandin $E_2$ in 10 ml of absolute methanol was added an ice-cooled solution of 300 mg of sodium borohydride in methanol. The solution was stirred at 0° for 20 minutes then room temperature for 1.0 hour. The solution was then quenched by the addition of 2.0 ml of water and the methanol was removed by rotary evaporation. The resultant aqueous solution was overlaid with ethyl acetate (10 ml), was acidified by the addition of 10% hydrochloric acid, and was extracted with ethyl acetate (4 × 5 ml). The combined organic extracts were washed with water (5 ml) and saturated brine (5 ml), was dried (anhydrous magnesium sulfate), and was concentrated. Purification of the crude residue by silica gel chromatography using mixtures of methylene chloride:methanol as eluent provided 17-(1-adamantyl)-ω-trisnorprostaglandin $F_{2\alpha}$ (28 mg) and 17-(1-adamantyl)-ω-trisnorprostaglandin $F_{2\beta}$ (28 mg).

EXAMPLE 57

17-(1-Adamantyl)-ω-trisnorprostaglandin $F_{2\alpha}$

A heterogeneous mixture of 447 mg (1.0 mmole) of 15-epi-17-(1-adamantyl)-ω-trisnorprostaglandin $F_{2\alpha}$ and 4.5 g of activated manganese dioxide in 45 ml of dry methylenechloride is stirred overnight at room temperature, filtered, and concentrated to afford 15-keto-17-(1-adamantyl)-ω-trisnorprostaglandin $F_{2\alpha}$ which is used without purification.

To a solution, cooled in ice, of 223 mg (0.50 mmole) of 15-keto-17-(1-adamantyl)-ω-trisnorprostaglandin $F_{2\alpha}$ in 22 ml of absolute methanol is added an ice-cooled solution of 669 mg of sodium borohydride in 85 ml of absolute methanol. After being stirred for 20 minutes at 0° and 1.0 hour at room temperature, the reaction is quenched by the addition of 6.6 ml of water. The methanol is removed by rotary evaporation and the resultant aqueous solution is overlaid with ethyl acetate, is acidified with 10% hydrochloric acid, and is further extracted with ethyl acetate. The combined organic extracts are washed with water and with saturated brine, are dried, (anhyrous magnesium sulfate), and are concentrated. Purification of the crude residue by silica gel chromatography affords 17-(1-adamantyl)-ω-trisnorprostaglandin $F_{2\alpha}$ and 15-epi-17-(1-adamantyl)-ω-trisnorprostaglandin $F_{2\alpha}$.

The other 15 epi prostaglandins of this invention having no lower alkyl group at $C_{15}$ may be similarly converted to their $C_{15}$ epimers by the process above.

EXAMPLE 58

Dimethyl 2-oxo-3-cyclohexylpropylphosphonate (2h)

A solution of 49.6 g (0.40 mole) dimethyl methylphosphonate (Aldrich) in 500 ml dry tetrahydrofuran was cooled to −78° in a dry nitrogen atmosphere. To the stirred phosphonate solution was added 188 ml of 2.34 M n-butyllithium in hexane solution (Alfa Inorganics, Inc.) dropwise over a period of 40 minutes at such a rate that the reaction temperature never rose above −65°. After an additional 5 minutes stirring at −78°, 31.2 g (0.20 mole) methylcyclohexylacetate was added dropwise at a rate that kept the reaction temperature less than −70° (20 minutes). After 1.0 hour at −78° the reaction mixture was allowed to warm to ambient temperature, neutralized with 25 ml acetic acid and rotary evaporated to a white gel. The gelatenous material was taken up in 75 ml water, the aqueous phase extracted with 100 ml portions of chloroform (3x), the combined organic extracts were backwashed (50 cc H₂O), dried (MgSO₄), and concentrated (water aspirator) to a crude residue and distilled, b.p. 160°-162° (0.2 mm) to give dimethyl 2-oxo-3-cyclohexylpropylphosphonate (2h).

The nmr spectrum (CDCl₃) showed a doublet centered at 3.77δ (J=11.5 cps, 6H) for

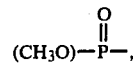

a doublet centered at 3.06δ (J=23 cps, 2H)

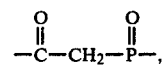

a doublet centered at 2.50δ (J=6 cps, 2H) for

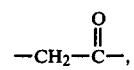

and multiplets at 0.71-2.04δS (11H) for the remaining protons. Their spectrum (CHCl₃) exhibited a strong absorbence at 1710 cm⁻¹ for the carbonyl group.

The necessary phosphonate precursors for the synthesis of the other cycloalkyl substituted prostaglandins of this invention are prepared in a similar manner from the appropriate methyl esters. These are transformed into their corresponding prostaglandin analogs of the present invention via the procedures of examples 59–82.

EXAMPLE 59

2-[3α-p-Phenylbenzoyloxy-5α-hydroxy-2β-(3-oxo-4-cyclohexyl-trans-1-buten-1-yl)-cyclopent-1α-yl/acetic acid, γ-lactone (3h)

Dimethyl 2-oxo-3-cyclohexylpropylphosphonate (2h) (4.95 g, 23.0 mmole) in 100 ml dry 1,2-dimethoxyethane was treated with 9.82 ml. (21.6 mmole) 2.2 M n-butyllithium in n-hexane (Alfa Inorganics, Inc.) in a dry nitrogen atmosphere at room temperature. A solution of 7.0 g (20.0 mmoles) of 2-[3α-p-phenylbenzoyloxy-5α-hydroxy-2β-formylcyclopent-1α-yl]acetic acid, γ-lactone in 50 ml of dry 1, 2-dimethoxyethane was added. After 1.5 hours the reaction mixture was quenched with 0.5 ml glacial acetic acid and concentrated. The residue was dissolved in methylene chloride; the organic solution was washed with saturated sodium bicarbonate and with water, was dried (MgSO₄), and was concentrated to provide 2-[3α-p-phenylbenzoyloxy-5α-hydroxy-2β-(3-oxo-4-cyclohexyl-1-buten-1-yl)cyclopent-1α-yl]acetic acid, γ-lactone (3h) melting at 147°-148° after recrystallization from methylene chloride: hexane.

The ir spectrum (CHCl₃) of the product exhibited adsorbtion bands at 1775 cm⁻¹ (strong), 1715 cm⁻¹ (strong), 1675 cm⁻¹ (medium) and 1630 cm⁻¹ (medium) attributable to the carbonyl groups and at 973 cm⁻¹ for the trans double bond. The nmr spectrum (CDCl₃) exhibited a multiplet at 8.2-7.2δ (9H) for the p-biphenyl group, a doublet of doublets centered at 6.70δ (1H, J=7, 16 cps) and a doublet centered at 6.2δ (1H, J=16 cps) for the olefinic proton, a multiplet at 5.5-4.9δ (2H) for the CO₂CH, and multiplets at 3.1-0.5δ (19H) for the remaining protons.

EXAMPLE 60

2-[3α-p-Phenylbenzoyloxy-5α-hydroxy-4-cyclohexyl-trans-1-buten-1-yl)cyclopent-1α-yl]acetic acid, γ-lactone (4h) and 2-[3α-p-phenylbenzoyloxy-5α-hydroxy-2β-(3β-hydroxy-4-cyclohexyl-trans-1-buten-1-yl)cyclopent-1α-yl]acetic acid, γ-lactone (5h)

To a solution of 4.72 g (10.0 mole) 2-[3α-p-phenylbenzoyloxy-5α-hydroxy-2β-(3-oxo-4-cyclohexyl-trans-1-buten-1-yl)cyclopent-1α-yl]acetic acid, γ-lactone (3h) in 47 ml dry tetrahydrofuran in a dry nitrogen atmosphere at ambient temperature was added dropwise 10.0 ml of a 0.5 M solution of zinc borohydride in 1,2-dimethoxyethane. After stirring at room temperature for 2 hours, a saturated sodium bitartrate solution was added dropwise until hydrogen evolution ceased. The reaction mixture was allowed to stir for 5 minutes at which time 100 ml dry methylene chloride was added. After drying (MgSO$_4$) and concentrating (water aspirator) the resultant semisolid was purified by column chromatography on silica gel (Baker "Analyzed" Reagent 60–200 mesh) using a 9:1 mixture of ether: cyclohexane as eluent. After elution of less polar impurities a fraction containing 1.64 g 2-[3α-p-phenylbenzoyloxy-5α-hydroxy-2β-(3α-hydroxy-4-cyclohexyl-trans-1-buten-1-yl)cyclopent-1α-yl]acetic acid, γ-lactone (4h) a fraction of 1.55 g of 2-[3α-p-phenylbenzoyloxy-5α-hydroxy-2β-(3β-hydroxy-4-cyclohexyl-trans-1-buten-yl)cyclopent-1α-yl]acetic acid, γ-lactone (5h).

The ir spectrum (CHCl$_3$) of 4 hand 5h had strong carbonyl absorptions at 1770 and 1715 cm$^{-1}$ and an absorption at 970 cm$^{-1}$ for the trans double bond.

The nmr spectrum of 4h and 5h exhibited multiplets at 8.2–7.3δ (9H) for the aromatic protons, a multiplet at 5.7–5.5δ (2H) for the trans double bond, a multiplet 5.4–4.9δ (2H) for the CO$_2$CH, a multiplet at 4.4–4.0δ (1H) for the CHOH, and multiplets at 2.9–0.5δ (19H) for the remaining protons.

EXAMPLE 61

2-[3α,5α-Dihydroxy-2β-(3α-hydroxy-4-cyclohexyl-trans-1-buten-1-yl)cyclopent-1α-yl]acetic acid, γ-lactone (6h)

A heterogeneous mixture of 1.64 g (3.46 mmole) of 2-[3α-p-phenylbenzoyloxy-5α-hydroxy-2β-(3α-hydroxy-4-cyclohexyl-trans-1-buten-1-yl)cyclopent-1α-yl]acetic acid, γ-lactone (4h), 16 ml. of absolute methanol and 478 mg of finely powdered, anhydrous potassium carbonate was stirred at room temperature for one hour, than cooled to 0°. To the cooled solution was added 6.9 ml (6.9 mmole) of 1.0N aqueous hydrochloric acid. After stirring at 0° for an additional 10 minutes, 16 ml. of water was added with concomitant formation of methyl p-phenylbenzoate which was collected by filtration. The filtrate was saturated with solid sodium chloride, extracted with ethyl acetate (2×30 ml.), the combined organic extracts were washed with saturated sodium bicarbonate (10 ml.) dried (MgSO$_4$) and concentrated to give 852 mg (84%) of viscous, oily 2-[3α,5α-dihydroxy-2β-(3α-hydroxy-4-cyclohexyl-trans-1-buten-1-yl)cyclopent-1α-yl]acetic acid, γ-lactone (6h).

The ir spectrum (CHCl$_3$) exhibited a strong adsorption at 1775 cm$^{-1}$ for the lactone carbonyl and medium adsorption at 970 cm$^{-1}$ for the trans-double bond.

EXAMPLE 62

2-[5α-Hydroxy-3α-(tetrahydropyran-2-yloxy)-2β-(3α-[tetrahydropyran-2-yloxy]-4-cyclohexyl-trans-1-buten-1-yl)cyclopent-1α-yl]acetic acid, γ-lactone (7h)

To a solution of 852 mg. (2.90 mmoles) 2-[3α,5α-dihydroxy-2β-(3α-hydroxy-4-cyclohexyl-trans-1-buten-1-yl)cyclopent-1α-yl]acetic acid γ-lactone (6h) in 15 ml anhydrous methylene chloride and 0.85 ml of 2,3-dihydropyran at room temperature in a dry nitrogen atmosphere was added 8 mg p-toluenesulphonic acid, monohydrate. After stirring for 15 minutes, the reaction mixture was combined with 100 ml ether, the ether solution washed with saturated sodium bicarbonate (1 × 15 ml) then saturated brine (1 × 15 ml), dried (MgSO$_4$) and concentrated to yield 1.25 g (>100%) crude 2-[5α-hydroxy-3α-(tetrahydropyran-2-yloxy)-2β-(3α-[tetrahydropyran-2-yloxy]-4-cyclohexyl-trans-1-buten-1-yl)cyclopent-1α-yl]acetic acid, γ-lactone (7h).

The ir (CHCl$_3$) spectrum had a medium adsorption at 970 cm$^{-1}$ for the trans-double bond and a strong adsorption at 1770 cm$^{-1}$ for the lactone carbonyl.

EXAMPLE 63

2-[5α-Hydroxy-3α-(tetrahydropyran-2-yloxy)-2β-(3α-tetrahydropyran-2-yloxy]-4-cyclohexyl-trans-1-buten-1-yl)cyclopent-1α-yl]acetaldehyde, γ-hexiacetal (8h)

A solution of 1.25 g (2.72 mmole) 2-[5α-hydroxy-3α-(tetrahydropyran-2-yloxy)-2β-(3α-[tetrahydropyran-2-yloxy]-4-cyclohexyltrans-1-buten-1-yl)cyclopent-1α-yl]acetic acid, γ-lactone (7h) in 20 ml toluene was cooled to −78° in a dry nitrogen atmosphere. To this cooled solution was added 3.70 ml of 20% diisobutylaluminum hydride in n-hexane (Alfa Inorganics) dropwise at such a rate so that the internal temperature never rose above −65° (15 minutes). After an additional 45 minutes of stirring at −78°, anhydrous methanol was added until gas evolution ceased and the reaction mixture was allowed to warm to room temperature. The reaction mixture was combined with 150 ml ether, washed with 50% sodium potassium tartrate solution (3 × 50 ml), dried (MgSO$_4$) and concentrated to yield 2-[5α-hydroxy-3α-(tetrahydropyran-2-yloxy)-2β-(3α-[tetrahydropyran-2-yloxy]-4-cyclohexyl-trans-1-buten-1-yl)cyclopent-1α-yl]acetaldehyde, γ-hemiacetal (8h) after purification by silica gel chromatography using a 4:1 mixture of benzene: ethyl acetate as eluent.

Their spectrum (CHCl$_3$) of (8h) exhibited a strong absorption at 975 cm$^{-1}$ for the trans double bond and no carbonyl absorption.

The product of this invention is converted to 16-cyclohexyl-ω-tetranorprostaglandin tetrazoles, carboximides or sulfonimides of the A, E or F series via the procedures of examples 103–110, 140–141, 156–165 and 169–170.

EXAMPLE 64

9α-Hydroxy-11α,15α-bis-(tetrahydropyran-2-yloxy)-16-cyclohexyl-cis-5-trans-13-ω-tetranorprostadienoic acid (9h)

To a solution of 1.94 g (4.38 mmole) (4-carbohydroxy-n-butyl) triphenylphosphonium bromide in a dry nitrogen atmosphere in 4.0 ml dry dimethyl sulfoxide was added 4.45 ml. (8.26 mmole) of a 1.86 M solution of sodium methylsulfinylmethide in dimethyl sulfoxide. To this red ylide solution was added dropwise a solution of 661 mg (1.42 mmole) 2-[5α-hydroxy-3α-(tetrahydropyran-2-yloxy)-2β-(3α-[tetrahydropyran-2-yloxy]-4-cyclohexyl-trans-1-buten-1-yl) cyclopent-1α-yl]acetaldehyde, γ-hemiacetal (8h) in 2.0 ml dry dimethyl sulfoxide over a period of 20 minutes. After an additional 1 hour stirring at room temperature, the reaction mixture was poured onto ice water. The basic aqueous solution was acidified to pHN 3 with 10% aqueous hydrochloric acid. The acidic solution was extracted with ethyl acetate (3 × 20 ml) and the combined organic extracts washed once with water (10 ml.), dried (MgSO$_4$) and evaporated to a residue, which was purified by column chromatography on silica gel (Baker "Analyzed" Reagent 60–200 mesh) using mixtures of benzene: chloroform as eluents. After removal of high R$_f$ impurities, 474 mg of 9α-hydroxy-11α,15α-bis-(tetrahydropyran-2-yloxy)-16-cyclohexyl-cis-5-trans-13-ω-tetranorprostadienoic acid (9h) was collected.

The ir spectrum (CHCl$_3$) of (9h) exhibited absorptions at 1710 cm$^{-1}$ for the acid carbonyl and 970 cm$^{-1}$ for the trans double bond. The nmr spectrum (CDCl$_3$) of (9h) exhibited a broad singlet 6.8 – 6.1δ (2H) for the OH, a multiplet at 5.6–5.2δ (4H) for the olefinic protons, a broad singlet at 4.6δ (2H) for the OCHO, multiplets at 4.2 –3.1δ (7H) for the CH$_2$O and CHO, and multiplets at 2.5 – 0.7δ (37H) for the remaining protons.

EXAMPLE 65

9α,11α,15α-trihydroxy-16-cyclohexyl-cis-5-trans-13-ω-tetranorprostadienoic acid (12h)

A solution of 125 mg. (0.23 mmole) 9α-hydroxy-11α,15α-bis-tetrahydropyran-2-yloxy)-16-cyclohexyl-cis-5-trans-13-ω-tetranorprostadienoic acid (10h) in 2.0 ml. of a 65:35 mixture of glacial acetic acid: water was stirred under nitrogen at room temperature overnight then was concentrated by rotary evaporation. The resultant crude oil was purified by column chromatography on silica gel (Mallinckrodt CC-7 100-200 mesh) using mixtures of chloroform: ethyl acetate as eluents. After elution of less polar impurities the colorless, oily 9α,11α,15α-trihydroxy-16-cyclohexyl-cis-5-trans-13-ω-tetranorprostadienoic acid (12H) was collected.

EXAMPLE 66

9-oxo-11α,15α-bis-(tetrahydropyran-2-yloxy)-16-cyclohexyl-cis-5-trans-13-ω-tetranorprostadienoic acid (10H)

To a solution cooled to −10° under nitrogen of 350 mg (0.639 mmole) 9α-hydroxy-11α,15α-bis-(tetrahydropyran-2-yloxy)-16-cyclohexyl-cis-5-trans-13-ω-tetranorprostadienoic acid (9h) in 7.5 ml. reagent grade acetone was added dropwise to 0.54 ml. of Jones' reagent. After 20 minutes at −20°, 0.54 ml. 2-propanol was added and the reaction mixture was allowed to stir an additional 5 minutes at which time it was combined with 75 ml. ethyl acetate, washed with water (3 × 10 ml.), dried (MgSO$_4$) and concentrated to give 332 mg. of 9-oxo-11α,15α-bis-(tetrahydropyran-2-yloxy)-16-cyclohexyl-cis-5-trans-13-ω-tetranorprostadienoic acid (10h).

EXAMPLE 67

9-oxo-11α,15α-dihydroxy-16-cyclohexyl-cis-5-trans-13-ω-tetranorprostadienoic acid (11h)

A solution of 332 mg. (0.61 mmole) 9-oxo-11α,15α-bis-(tetrahydropyran-2-yloxy)-16-cyclohexyl-cis-trans-13-ω-tetranorprostadienoic acid (10h) in 5.0 ml. of a 65:35 mixture of glacial acetic acid: water was stirred under nitrogen at room temperature overnight then was concentrated by rotary evaporation. The resultant crude oil was purified by column chromatography on silica gel (Mallinckrodt CC-7 100-200 mesh) using mixtures of chloroform: ethyl acetate as eluents. After elution of less polar impurities the colorless, oily 9-oxo-11α,15α-dihydroxy-16-cyclohexyl-cis-5-trans-13-ω-tetranorprostadienoic acid (11h) was collected.

EXAMPLE 68

A solution of 50 g. of indan-2-carboxylic acid (prepared according to the procedure reported by E. D. Bergmann and E. Hoffman, *J. Org. Chem.*, 26, 3555 (1961)) and 5 ml. of con d sulfuric acid in 500 ml. of methanol is heated at reflux for 3.0 hours then is cooled in ice. The cooled solution is neutralized (pH∼5) with saturated sodium bicarbonate, is concentrated, and the aqueous layer is extracted with methylene chloride. The combined organic extracts are washed with saturated bicarbonate, with saturated brine, are dried (anhydrous magnesium sulfate), and are concentrated. Distillation of the crude residue in vacuo provides the desired methyl indan-2-carboxylate.

EXAMPLE 69

2-[3α,5α-Dihydroxy-2β-(3β-hydroxy-4-cyclohexyl-trans-1-buten-1-yl)cyclopent-1α-yl]acetic acid, γ-lactone (6′h)

A heterogenous mixture of 1.55 g. (3.28 mmole) of 2-[3α-p-phenylbenzoloxy-5α-hydroxy-2β-(3β-hydroxy-4-cyclohexyl-trans-1-buten-1-yl)cyclopent-1α-yl]acetic acid, γ-lactone (5h), 15 ml. of absolute methanol and 453 mg of finely powdered, anhydrous potassium carbonate was stirred at room temperature for one hour, than cooled to 0°. To the cooled solution was added 6.5 ml (6.5 mmole) of 1.0N aqueous hydrochloric acid. After stirring at 0° for an additional 10 minutes, 15 ml. of water was added with concomitant formation of methyl p-phenylbenzoate which was collected by filtration. The filtrate was saturated with solid sodium chloride, extracted with ethyl acetate (2 × 30 ml.), the combined organic extracts were washed with saturated sodim bicarbonate (10 ml.) dried (MgSO$_4$) and concentrated to give 793 mg (82.5%) of viscous, oily 2-[3α,5-dihydroxy-2β-(3β-hydroxy-4-cyclohexyl-trans-1-buten-1-yl)cyclopent-1α-yl]acetic acid, γ-lactone (6′h).

The ir spectrum (CHCl$_3$) exhibited a strong adsorption at 1775 cm$^{-1}$ for the lactone carbonyl and medium adsorption at 975 cm$^{-1}$ for the trans-double bond.

EXAMPLE 70

2-[5α-Hydroxy-3α-(tetrahydropyran-2-yloxy)-2β-(3β-[tetrahydropyran-2-yloxy]-4-cyclohexyl-trans-1-buten-1-yl)cyclopent-1α-yl]acetic acid, γ-lactone (7′h)

To a solution of 793 mg (2.66 mmoles) 2-[3α,5α-dihydroxy-2β-(3β-hydroxy-4-cyclohexyl-trans-1-buten-1-yl)cyclopent-1α-yl]acetic acid, γ-lactone (6′h) in 15 ml anhydrous methylene and 0.8 ml of 2,3-dihydropyran at room temperature in a dry nitrogen atmosphere was added 8 mg p-toluenesulfonic acid, monohydrate. After stirring for 15 minutes, the reaction mixture was combined with 100 ml ether, the ether solution washed with saturated sodium bicarbonate (1 × 15 ml) then saturated brine (1 × 15 ml), dried (MgSO$_4$) and concentrated to yield 1.24 g (>100%) crude 2-[5α-hydroxy-3α-(tetrahydropyran-2-yloxy)-2β-(3β-

[tetrahydropyran-2-yloxy]-4-cyclohexyl-trans-1-buten-1-yl)cyclopent-1α-yl]acetic acid, γ-lactone (7'h).

The ir (CHCl₃) spectrum had a medium adsorption at 970 cm⁻¹ for the trans-double bond and a strong absorption at 1770 cm⁻¹ for the lactone carbonyl.

EXAMPLE 71

2-[5α-Hydroxy-3α-(tetrahydropyran-2-yloxy)-2β-(3β-[tetrahydropyran-2-yloxy]-4-cyclohexyl-trans-1-buten-1-yl)cyclopent-1α-yl]acetaldehyde, γ-hemiacetal (8'h)

A solution of 1.24 g (2.68 mmoles) 2-[5α-hydroxy-3α-(tetrahydropyran-2-yloxy)-2β-(3β-[tetrahydropyran-2-yloxy]-4-cyclohexyltrans-1-buten-1-yl)cyclopent-1α-yl]acetic acid, γ-lactone (7'h) in 20 ml dry toluene was cooled to −78° in a dry nitrogen atmosphere. To this cooled solution was added 3.70 ml of 20% diisobutylaluminum hydride in n-hexane (Alfa Inorganics) dropwise at such a rate so that the internal temperature never rose above −65° (15 minutes). After an additional 45 minutes of stirring at −78°, anhydrous methanol was added until gas evolution ceased and the reaction mixture was allowed to warm to room temperature. The reaction mixture was combined with 150 ml ether, washed with 50% sodium potassium tartrate solution (3 × 50 ml), dried (MgSO₄) and concentrated to yield 509 mg 2-[5α-hydroxy-3α-(tetrahydropyran-2-yloxy)-2β-(3β-[tetrahydropyran-2-yloxy]-4-cyclohexyl-trans-1-buten-1-yl)cyclopent-1-yl]acetaldehyde, γ-hemiacetal (8'h) after purification by silica gel chromatography using a 4:1 mixture of benzene:ethyl acetate as eluent.

The ir spectrum (CHCl₃) of (8'h) exhibited a strong absorption at 975 cm⁻¹ for the trans-double bond and no carbonyl absorption.

The product of this reaction is converted to 15-epi-16-cyclohexyl-ω-tetranorprostaglandin tetrazoles, carboximides or sulfonimides of the A, E or F series via the procedures of examples 103–110, 140–141, 156–165 and 169–170.

EXAMPLE 72

9α-Hydroxy-11α,15β-bis-(tetrahydropyran-2-yloxy)-16-cyclohexyl-cis-5-trans-13-ω-tetranorprostadienoic acid (9'h)

To a solution of 1.58 g (3.56 mmole) (4-carbohydroxy-n-butyl) triphenylphosphonium bromide in a dry nitrogen atmosphere in 4.0 ml dry dimethyl sulfoxide was added 3.56 ml (6.62 mmole) of a 1.86 M solution of sodium methylsufinylmethide in dimethyl sulfoxide. To this red ylide solution was added dropwise a solution of 509 mg (1.10 mmole) 2-[5α-hydroxy-3α-(tetrahydropyran-2-yloxy)-2β-(3β-[tetrahydropyran-2-yloxy]-4-cyclohexyl-trans-1-buten-1-yl)cyclopent-1α-yl]acetaldehyde, γ-hemiacetal (8'h) in 2.0 ml dry dimethyl sulfoxide over a period of 20 minutes. After and additional 1 hour stirring at room temperature, the reaction mixture was poured onto ice water. The basic aqueous solution was acidified to pH ∼3 with 10% aqueous hydrochloric acid. The acidic solution was extracted with ethyl acetate (3 × 20 ml) and the combined organic extracts washed once with water (10 ml), dried (MgSO₄) and evaporated to an oily residue which was purified by column chromatography on silica gel (Baker "Analyzed" Reagent 60–200 mesh) using mixtures of benzene:chloroform as eluents. After removal of high R_f impurities, 617 mg of 9α-hydroxy-11α,15β-bis-(tetrahydropyran-2-yloxy)-16-cyclohexyl-cis-5-trans-13-ω-tetranorprostadienoic acid (9'h) was collected.

The ir spectrum (CHCl₁) of (9'h) exhibited absorptions at 1710 cm⁻¹ for the acid carbonyl and 970 cm⁻¹ for the trans double bond. The nmr spectrum (CDCl₃) of (9'h) exhibited a broad singlet at 6.8–6.1 δ (2H) for the OH, a multiplet at 5.6–5.2 δ (4H) for the olefinic protons, a broad singlet at 4.6 δ (2H) for the OCHO, multiplets at 4.2–3.1 δ (7H) for the CH₂O and CHO, and multiplets at 2.5–0.7 δ (37H) for the remaining protons.

EXAMPLE 73

9α,11α,15β-trihydroxy-16-cyclohexyl-cis-5-trans-13-ω-tetranorprostadienoic acid (12'h)

A solution of 200 mg. (0.364 mmole) 9α-hydroxy-11α,15β-bis-tetrahydropyran-2-yloxy)-16-cyclohexyl-cis-5-trans-13-ω-tetranorprostadienoic acid (9'h) in 2.0 ml. of a 65:35 mixture of glacial acetic acid:water was stirred under nitrogen at room temperature overnight then was concentrated by rotary evaporation. The resultant crude oil was purified by column chromatography on silica gel (Mallinckrodt CC-7 100–200 mesh) using mixtures of chloroform: ethyl acetate as eluents. After elution of less polar impurities the colorless, oily 9α,11α,15β-trihydroxy-16-cyclohexyl-cis-5-trans-13-ω-tetranorprostadienoic acid (12'h) was collected.

EXAMPLE 74

9-oxo-11α,15β-bis-(tetrahydropyran-2-yloxy)-16-cyclohexyl-cis-5-trans-13-ω-tetranorprostadienoic acid (10'h)

To a solution cooled to −10° under nitrogen of 400 mg (0.73 mmole) 9α-hydroxy-11α,15β-bis-(tetrahydropyran-2-yloxy)-16-cyclohexyl-cis-5-trans-13-ω-tetranorprostadienoic acid (9'h) in 10.0 ml reagent grade acetone was added dropwise to 0.68 ml of Jones' reagent. After 20 minutes at −20°, 0.68 ml 2-propanol was added and the reaction mixture was allowed to stir an additional 5 minutes at which time it was combined with 75 ml ethyl acetate, washed with water (3 × 10 ml), dried (MgSO₄) and concentrated to give 375 mg. of 9-oxo-11α,15β-bis-(tetrahydropyran-2-yloxy)-16-cyclohexyl-cis-5-trans-13-ω-tetranorprostadienoic acid (10'h).

EXAMPLE 75

9-oxo-11α,15β-dihydroxy-16-cyclohexyl-cis-5-trans-13-ω-tetranorprostadienoic acid (11'h)

A solution of 375 mg. (0.687 mmole) 9-oxo-11α,15β-bis-tetrahydropyran-2-yloxy)-16-cyclohexyl-cis-5-trans-13-ω-tetranorprostadienoic acid (10'h) in 5.0 ml of a 65:35 mixture of glacial acetic acid:water was stirred under nitrogen at room temperature overnight then was concentrated by rotary evaporation. The resultant crude oil was purified by column chromatography on silica gel (Mallinckrodt CC-7 100–200 mesh) using mixtures of chloroform:ethyl acetate as eluents. After elution of less polar impurities the colorless, oily 9-oxo-11α,15β-dihydroxy-16-cyclohexyl-cis-5-trans-13-ω-tetranorprostadienoic acid (11'h) was collected.

EXAMPLE 76

9-oxo-15α-hydroxy-16-cyclohexyl-Δ10,11-5-cis-13-trans-ω-tetranorprostatrienoic acid (15h)

A solution of 100 mg of 9-oxo-11α,15α-dihydroxy-16-cyclohexyl-5-cis-13-trans-ω-tetranorprostatrienoic acid 2.0 ml of dry methylene chloride and 2.0 ml of 97% formic acid is stirred at room temperature under nitrogen for 6 hours. The reaction mixture is then diluted with xylene and concentrated to afford after purification by silica gel chromatography 9-oxo-15α-hydroxy-16-cyclohexyl-Δ10,11-5-cis-13-trans-ω-tetranorprostatrienoic acid.

By the above procedure the other prostaglandin analogs of $E_2$, $E_1$ or $E_o$ type, can be converted to the corresponding analogs of the A series.

EXAMPLE 77

9α,11α,15α-Trihydroxy-16-cyclohexyl-5-cis-13-trans-ω-tetranorprostadienoic acid (12h) and 9β,11α,15α-trihydroxy-16-cyclohexyl-5-cis-13-trans-ω-tetranorprostadienoic acid (9-epi 12h)

To a solution of 100 mg of 9-oxo-11α,15α-dihydroxy-16-cyclohexyl-5-cis-13-trans-ω-tetranorprostadienoic acid (11h) in 5 ml of absolute ethanol cooled to 0° is added dropwise a solution of 50 mg of sodium borohydride in 2 ml of absolute ethanol. The reaction mixture is stirred under nitrogen at 0° for 2.0 hours, then is concentrated by rotary evaporation. The residue is dissolved in methylene chloride, is washed with brine, is dried (anhydrous magnesium sulfate) and is concentrated. Purification of the crude product by silica gel chromatography provides 9α,11α,15α-trihydroxy-16-cyclohexyl-5-cis-13-trans-ω-tetranorprostadienoic acid (12h) and 9β,11α,15α-trihydroxy-16-cyclohexyl-5-cis-13-trans-tetranorprostadienoic acid (9-epi 12h).

The other prostaglandin analogs of the $F_\beta$ series of this invention are prepared as described above by substituting the appropriate analog of the E series for 11h above.

EXAMPLE 78

2-[3α-p-Phenylbenzoyloxy-5α-hydroxy-2β-(3α-hydroxy-4-cyclohexyl but-1-yl)cyclopent-1α-yl/acetic acid, α-lactone (19h) and 2-[3α-p-phenylbenzoyloxy-5α-hydroxy-2β-(3β-hydroxy-4-cyclohexyl but-1-yl)cyclopent-1α-yl/acetic acid, α-lactone (19'h)

A heterogenous solution of 5.10 g of 2-[3α-p-phenylbenzoyloxy-5α-hydroxy-2β-(3-oxo-4-cyclohexyl-trans-1-buten-1-yl)cyclopent-1α-yl/acetic acid, γ-lactone (3h) and 0.510 g of 5% palladium on carbon in 50 ml of absolute methanol is stirred under 1 atmosphere of hydrogen for 4 hours. The mixture is then filtered (Celite) and concentrated to afford 2-[3α-p-phenylbenzoyloxy-5α-hydroxy-2β-(3-oxo-4-cyclohexyl but-1-yl)cyclopent-1α-yl/acetic acid, α-lactone (5h).

To a solution of 3.84 g (10.0 mmoles) of the crude hydrogenation product (5h) above in 40 ml of absolute ethanol is added 167 mg (5.0 mmole) of sodium borohydride. The solution is stirred at room temperature under nitrogen for 2 hours then is concentrated. The residue is diluted with 0.1N hydrochloric acid and the aqueous is extracted with ethyl acetate. The combined organic extracts are washed with saturated brine, are dried (anhydrous magnesium sulfate), and are concentrated. Purification of the crude residue by silica gel chromatography affords 2-[3α-p-phenylbenzoyloxy-5α-hydroxy-2β-(3-α-p-phenylbenzoyloxy-5α-hydroxy-2β-(3β-hydroxy-4-cyclohexyl but-1-yl)cyclopent-1α-yl/acetic acid, γ-lactone (19'h). This is a suitable starting material for the production of the 13,14 dihydro-ω-pentaprostaglandin by the procedures of examples 61–66 and 77.

EXAMPLE 79

9α-Hydroxy-11α,15α-bis-(tetrahydropyran-2-yloxy)-16-cyclohexyl-ω-tetranorprostanoic acid (23h)

A heterogeneous mixture of 1.52 g. of the 9α-hydroxy-11α,15α-bis-(tetrahydropyran-2-yloxy)-5-cis-13-trans-16-cyclohexyl-ω-tetranorprostadienoic acid (9h) prepared above and 152 mg. of 5% palladium on carbon in 15 ml. of absolute methanol is stirred under 1 atmosphere of hydrogen at 0° for 4 hours. The reaction mixture is filtered (Celite) and concentrated to provide 9α-hydroxy-11α,15α-bis-(tetrahydropyran-2-yloxy)-16-cyclohexyl-ω-tetranorprostanoic acid (23h).

The product is transformed into 16-cyclohexyl-ω-tetranorprostaglandins of the A, E and F series via the procedures of examples 65–67 and 77.

EXAMPLE 80

9-oxo-11α,15α-dihydroxy-16-cyclohexyl-ω-tetranorprostanoic acid

A heterogeneous mixture of 120 mg 9-oxo-11α,15α-dihydroxy-16-cyclohexyl-5-cis-13-trans-ω-tetranorprostadienoic acid (11h) and 12 mg of 5% palladium on carbon in 12 ml of absolute methanol is stirred under 1 atmosphere of hydrogen at 0° for 3 hours. The reaction mixture is filtered (Celite) and concentrated. The crude residue is purified by silica gel chromatography to provide 9-oxo-11α,15α-dihydroxy-16-cyclohexyl-ω-tetranorprostanoic acid.

By the above procedure the other prostaglandin analogs of this invention of the $E_2$, $F_{2\alpha}$ or $F_{2\beta}$ type may be converted to the corresponding analog of the "zero" series.

EXAMPLE 81

9α-Hydroxy-11α,15α-bis-(tetrahydropyran-2-yloxy)-16-cyclohexyl-13-trans-ω-tetranorprostenoic acid (21h)

A heterogeneous mixture of 965 mg of the 9α-hydroxy-11α,15α-bis-(tetrahydropyran-2-yloxy)-16-cyclohexyl-5-cis-13-trans-ω-tetranorprostenoic acid (9h) and 96 mg 5% palladium on carbon in 10 ml of absolute methanol is stirred under 1 atmosphere of hydrogen at −22° for 5 hours. The mixture is then filtered (Celite) and the filtrate is concentrated to afford 9α-hydroxy-11α,15α-bis-(tetrahydropyran-2-yloxy)-16-cyclohexyl-13-trans-ω-tetranorprostenoic acid.

By the above procedure the other prostaglandin analogs of this invention of the $E_2$, $F_{2\alpha}$ or $F_{2\beta}$ may be converted to the corresponding analog of the "one" series.

EXAMPLE 82

9-oxo-11α,15α-dihydroxy-16-cyclohexyl-13-trans-ω-tetranorprostenoic acid

A solution of 68 mg (0.18 mmole) 9-oxo-11α,15α-dihydroxy-16-cyclohexyl-cis-5-trans-13-ω-tetranorprostadienoic acid (11h) in 6 ml of anhydrous ether is treated with 448 mg (3.6 mmole) dimethylisopropyl chlorosilane and 36.0 mg (3.6 mmoles)triethylamine at room temperature under nitrogen for 48 hours. The reaction mixture is cooled to 0°, methanol is added, and the resulting solution is washed with water, is dried (anhydrous magnesium sulfate), and is concentrated. The residue is dissolved in methanol (6 ml), 5% palladium on carbon (30 mg) is added, and the resultant heterogeneous mixture is stirred at −22° under 1 atmosphere of hydrogen for 4 hours. After filtration (Celite)

and concentration of the filtrate, the residue is dissolved in a 65:35 mixture of acetic acid:water. The solution is stirred for 10 minutes at room temperature, is then diluted with water, and is extracted with ethyl acetate (4x). The combined organic extracts are washed with brine, are dried (anhydrous magnesium sulfate), and are concentrated to afford, after purification by silica gel chromatography, 9-oxo-11α,15α-dihydroxy-16-cyclohexyl-13-trans-ω-tetranorprostenoic acid.

The other prostaglandin $E_1$ analogs of the present invention are similarly prepared from the corresponding $E_2$ precursors.

EXAMPLE 83

2-[3α-p-Phenylbenzoyloxy-5α-hydroxy-2β-(3α-hydroxy-3β-methyl-4-cyclohexyl-trans-1-buten-1-yl)cyclopent-1α-yl]acetic acid, γ-lactone (13h) and 2-[3α-p-phenylbenzoyloxy -5α-hydroxy-2β-(3β-hydroxy-3α-methyl-4-cyclohexyl-trans-1-buten-1-yl)cyclopent-1α-yl]acetic acid, γ-lactone (14h)

To a solution of 1.89 g (4.0 mmoles) of the 2-[3α-p-phenylbenzoyloxy-5α-hydroxy-2β-(3-oxo-4-cyclohexyl-trans-1-buten-1-yl) cyclopent-1α-yl]acetic acid, γ-lactone (3h) in 20 ml of anhydrous ether and 20 ml of dry tetrahydrofuran under a dry nitrogen atmosphere at −78° is added dropwise 4.0 ml of a 1.0M solution of methyllithium in ether (Alfa). After being stirred at −78° for 15 minutes, the reaction is quenched by the dropwise addition of glacial acetic acid until the pH of the solution is 7. The quenched mixture is warmed to room temperature, is diluted with methylene chloride, is washed with water (2x) and saturated brine (1x), is dried (anhydrous magnesium sulfate), and is concentrated. Purification of the residue by silica gel chromatography affords 2-[3α-p-phenylbenzoyloxy-5α-hydroxy-2β-(3α-hydroxy-3β-methyl-4-cyclohexyl-trans-1-buten-1-yl)cyclopent-1α-yl]acetic acid, γ-lactone (13h) and 2-[3α-p-phenylbenzoyloxy-5α-hydroxy-2β-(3β-hydroxy-3α-methyl-4-cyclohexyl-trans-1-buten-1-yl)cyclopent-1α-yl]acetic acid, γ-lactone (14h).

The products of this reaction are converted into 15-methyl-16-cyclohexyl-ω-tetranorprostaglandins of the A, E or F series via the procedures of examples 61–77. Other lower alkyl derivatives are prepared using the above procedure substituting the appropriate lower alkyl lithium reagent for the methyl lithium.

EXAMPLE 84

2-[5α-Hydroxy-3α-(tetrahydropyran-2-yloxy)-2β-(3α-tetrahydropyran-2-yloxy)-4-cyclohexyl but-1-yl)cyclopent-1α-yl]acetic acid, γ-lactone A heterogeneous mixture of 1.56 g. of the 2-[5α-hydroxy-3α-(tetrahydropyran-2-yloxy)-2β-(3α-(3α-(tetrahydropyran-2-yloxy)-4-cyclohexyl-trans-1-buten-1-yl)cyclopent-1α-yl]acetic acid, γ-lactone (7h) prepared above and 156 mg. of 5% palladium on carbon in 15 ml. of absolute methanol is stirred under 1 atmosphere of hydrogen for 2 hours. The reaction mixture is filtered (Celite) and concentrated to provide the 2-[5α-hydroxy-3α-(tetrahydropyran-2-yloxy)-2β-(3α-(tetrahydropyran-2-yloxy)-4-cyclohexy but-1-yl) cyclopent-1α-yl]acetic acid, γ-lactone (dihydro 7h).

The product of this reaction may be converted to the 13,14-dihydro,16-cyclohexyl-ω-tetranorprostaglandins of the A, E and F series of this invention by the procedures of examples 61–77.

From the appropriately substituted lactones of type 7 (prepared via the methods described in examples 1–5 and 58–62) the other 13,14-dihydro-15-dihydro-15-substituted-ω-pentanorprostaglandins of this invention may be prepared as above. The products of dihydro 7 type are also suitable substrates for the reaction of example 83 to product precursors for 15-lower alkyl-13,14-dihydro-15-substituted-ω-pentanorprostaglandin analogs of this invention.

EXAMPLE 85

9α,11α,15α-Trihydroxy-b 15β-methyl-16-cyclohexyl-5-cis-13-trans-ω-tetranorprostadienoic acid and 9-oxo-11α,11α,15α-dihydroxy-15β-methyl-16-cyclohexyl-5-cis-13-trans-ω-tetranorprostadienoic acid To a solution of 300 mg 9α,11α,15α-trihydroxy-16-cyclohexyl-5-cis-13-trans-ω-tetranorprostadienoic acid (I) in 15 ml of dioxane under nitrogen at 50° is added 220 mg of 2,3-dichloro-5,6-dicyano-1,4-benzoquinone. The mixture is stirred at 45°–50° overnight under nitrogen, is cooled, and is filtered through Celite. The filtrate is diluted with methylene chloride, is washed with saturated brine, is dried (anhydrous magnesium sulfate) and is concentrated by rotary evaporation. Purification of the residue by silica gel chromatography provides 9α,1-1α-dihydroxy-15-oxo-16-cyclohexyl-5-cis-13-trans- ω-tetranorprostadienoic acid.

The keto acid prepared above (550 mg) is dissolved in dry tetrahydrofuran (55 ml) and is treated with 1,1,1,3,3,3-hexamethyl-disilazane (6 ml) and triethylchlorisilane (1 ml) at room temperature under nitrogen for 18 hours, then is diluted with xylene. This mixture is filtered and is concentrated to afford the trimethylsilyl derivative of 9α,11α-dihydroxy-15-oxo-16-cyclohexyl-5-cis-13-trans-ω-tetranorprostadienoic acid.

To a solution of trimethylsilyl derivative prepared above (350 mg) in anhydrous ether (35 ml) is added dropwise 1.5 ml of a 3M solution of methyl magnesium bromide in ether. The solution is stirred for 1 hour under nitrogen then is quenched by pouring into 35 ml of saturated aqueous ammonium chloride. The aqueous layer is extracted with ether (2x), and the combined organic extracts are washed with saturated brine, are dried (anhydrous magnesium sulfate), and is concentrated by rotary evaporation. The residue is dissolved in a 65:35 mixture of acetic acid:water (10 ml). After being stirred for 5 hours at room temperature, the solution is concentrated. Purification of the residue by column chromatography (Mallinckrodt CC-7 Special) affords 9α,11α,15β-trihydroxy-15α-methyl-16-cyclohexyl-5-cis-13-trans-ω-tetranorprostadienoic acid and 9α,11α,1-5α-trihydroxy-15β-methyl-16-cyclohexyl-5-cis-13-trans-ω-tetranorprostadienoic acid (II).

To a solution cooled to −45° of 133 mg (0.35 mmole) of the 9α,11α,15α-trihydroxy-15β-methyl-16-cyclohexyl-5-cis-13-trans-ω-tetranorprostadienoic acid prepared above in 2 ml of acetone and 128 mg (0.9 mmole) of trimethylsilyl diethylamine is stirred under nitrogen for 24 hours, then is concentrated. The crude residue is dissolved in 2.0 ml of dry methylene chloride and 3.5 ml (0.35 mmole) of a 0.1M solution of Collins' reagent in methylene chloride is added. The resultant black solution is stirred for 15 minutes at room temperature, then is filtered through a column of silica gel using methylene chloride as eluent. Concentration of the eluent affords a crude residue which, without purification, is dissolved in 2 ml of a 65:35 mixture of acetic acid:water. After being stirred for 3 hours at room temperature the solution is concentrated. Purification of the crude residue by column chromatography (Mallinckrodt CC-7 Special) provides the 9-oxo:11α,15α-dihydroxy-15β-methyl-16-cyclohexyl-5-cis-13-trans-ω-tetranorprostadienoic acid (III).

The scheme outlined above is an alternate route to the 15 alky-15-substituted-ω-pentanorprostaglandins of this invention starting from the corresponding 15-substituted-ω-pentanorprostaglandin. The product of the reaction may be converted to 15-substituted-ω-pentanorprostaglandin of the E and F "one" and E and F "zero" series via the procedures of examples 80 and 81.

EXAMPLE 86

Dimethyl 2-Oxo-3-(2-norbornyl)propylphosphonate

A solution of 63.9 g (0.516 mole) dimethyl methylphosphonate (Aldrich) in 645 ml dry tetrahydrofuran was cooled to −78° in a dry nitrogen atmosphere. To the stirred phosphonate solution was added 251 ml of 2.2 M n-butyllithium in hexane solution (Alfa Inorganics, Inc.) dropwise over a period of 40 minutes at such a rate that the reaction temperature never rose about −65°. After an additional 5 minutes stirring at −78°, 43.5 g (0.258 mole) methyl (2-norbornyl)acetate was added dropwise at a rate that kept the reaction temperature less than −70° (20 minutes). After 1.0 hour at −78° the reaction mixture was allowed to warm to ambient temperature, neutralized with 35 ml acetic acid and rotary evaporated to a white gel. The gelatinous material was taken up in 50 ml water, the aqueous phase extracted with 100 ml portions of chloroform (4x), the combined organic extracts were backwashed (50 cc $H_2O$), dried ($MgSO_4$), and concentrated (water aspirator) to a crude residue and distilled, dimethyl 2-oxo-3-(2-norbornyl) propylphosphonate (b.p. 138°–141°/0.3 mm).

The product of this reaction is converted to 16-(2-norbornyl)-ω-tetranorprostaglandins of the A, E or F series via the procedures of Examples 59–84, 103–110, 140–141, 156–165 and 169–170.

EXAMPLE 87

Dimethyl 2-Oxo-6-cycopropylhexylphosphonate

A solution of 49.6 g (0.40 mole) dimethyl methylphosphonate (Aldrich) in 500 ml dry tetrahydrofuran is cooled to −78° in a dry nitrogen atmosphere. To the stirred phosphonate solution is added 188 ml of 2.34 M n-butyllithium in hexane solution (Alfa Inorganics, Inc.) dropwise over a period of 18 minutes at such a rate that the reaction temperature never rises above −65°. After an additional 5 minutes stirring at −78°, 25.6 g (0.20 mole) methyl 5-cyclopropylvalerate is added dropwise at a rate that keeps the reaction temperature less than −70° (20 minutes). After 1.0 hour at −78° the reaction mixture is allowed to warm to ambient temperature, neutralized with 25 ml acetic acid and rotary evaporated to a white gel. The gelatinous material is taken up in 75 ml water, the aqueous phase extracted with 100 ml portions of chloroform (3x), the cmbined organic extracts are backwashed (50 cc $H_2O$), dried ($MgSO_4$), and concentrated (water aspirator) to a crude residue and distilled to give dimethyl 2-oxo-6-cyclopropylhexylphosphonate.

The product of this reaction is converted into 19-cyclopropyl-ω-norprostaglandin analogs of the A, E or F series via the procedure of examples 57–84, 103–110 140–141, 156–165 and 169–170.

EXAMPLE 88

Dimethyl 2-Oxo-7-cycloentylheptylphosphonate

A solution of 49.6 g (0.40 mole) dimethyl methylphosphonate (Aldrich) in 500 ml dry tetrahydrofuran is cooled to −78° in a dry nitrogen atmosphere. To the stirred phosphonate solution is added 188 ml of 2.34 M n-butyllithium in hexane solution (Alfa Inorganics, Inc.) dropwise over a period of 18 minutes at such a rate that the reaction temperature never rises about −65°. After an additional 5 minutes stirring at −78°, 25.6 g (0.20 mole) methyl 6-cyclopentylhexanoate is added dropwise at a rate that keeps the reaction temperature less than −70° (20 minutes). After 1.0 hour at −78° the reaction mixture is allowed to warm to ambient temperature, neutralized with 25 ml acetic acid and rotary evaporated to a white gel. The gelatinous material is taken up in 75 ml water, the aqueous phase extracted with 100 ml portions of chloroform (3x), the combined organic extracts are backwashed (50 cc $H_2O$), dried ($MgSO_4$), and concentrated (water aspirator) to a crude residue and distilled to give dimethyl 2-oxo-7-cyclopentyheptylphosphonate.

The product of this reaction is converted into 20-cyclopentyl prostaglandin analogs of the A, E or F series via the procedure of Examples 57–84, 103–110, 140–141, 156–165 and 169–170.

EXAMPLE 89

Dimethyl 2-Oxo-3-(2-indanyl)propylphosphonate

A solution of 49.6 g (0.40 mole) dimethyl methylphosphonate (Aldrich) in 500 ml dry tetrahydrofuran is cooled to −78° in a dry nitrogen atmosphere. To the stirred phosphonate solution is added 188 ml of 2.34 M n-butyllithium in hexane solution (Alfa Inorganics, Inc.) dropwise over a period of 40 minutes at such a rate that the reaction temperature never rises above −65°. After an additional 5 minutes stirring at −78°, 36.0 g (0.20 mole) methyl (2-indanyl)acetate added dropwise at a rate that keeps the reaction temperature less than −70° (20 minutes). After 1.0 hour at −78° the reaction mixture is allowed to warm to ambient temperature, neutralized with 25 ml acetic acid and rotary evaporated to a white gel. The gelatinous material is taken up in 75 ml water, the aqueous phase extracted with 100 ml portions of choroform (3x), the combined organic extracts are backwashed (50 cc $H_2O$), dried ($MgSO_4$), and concentrated (water aspirator) to a crude residue and distilled, dimethyl 2-oxo-3-(2-indanyl) propylphosphonate.

The product of this reaction is converted to 16-(2-indanyl)-ω-tetranorprostaglandins ofthe A, E and F series via the procedures of Examples 59–84, 103–110, 140–141, 156–165 and 169–170.

EXAMPLE 90

Dimethyl 2-Oxo-2-cyclodecylethylphosphonate

A solution of 49.6 g (0.40 mole) dimethyl methylphosphonate (Aldrich) in 500 ml dry tetrahydrofuran is cooled to −78° in a dry nitrogen atmosphere. To the stirred phosphonate solution is added 188 ml of 2.34 M n-butyllithium in hexane solution (Alfa Inorganics, Inc.) dropwise over a period of 18 minutes at such a rate that the reaction temperature never rises above −65°. After an additional 5 minutes stirring at −78°, 25.6 g (0.20 mole) methyl cyclodecanecarboxylate is added dropwise at a rate that keeps the reaction temperature less than −70° (20 minutes). After 1.0 hour at −78° the reaction mixture is allowed to warm to ambient temperature, neutralized with 25 ml acetic acid and rotary evaporated to a white gel. The gelatinous material is taken up in 75 ml water, the aqueous phase extracted with 100 ml portions of chloroform (3x), the combined organic extracts are backwashed (50 cc H$_2$O), dried (MgSO$_4$), and concentrated (water aspirator) to a crude residue and distilled to give dimethyl 2-oxo-2-cyclodecylethylphosphonate.

The product of this reaction in converted into 15-cyclodecyl-ω-pentanorprostaglandin analogs of the A, E or F series via the procedure of Examples 57–84, 103–110, 140–141, 156–165 and 169–170.

EXAMPLE 91

Dimethyl 2-oxo-2-(2-indanyl)ethylphosphonate (2i)

A solution of 20.4 g (164 mmoles) dimethyl methylphosphonate (Aldrich) in 200 ml dry tetrahydrofuran was cooled to −78° in a dry nitrogen atmosphere. To the stirred phosphonate solution was added 82.6 ml of 2.25M n-butyllithium in hexane solution (Alfa Inorganics, Inc.) dropwise over a period of 20 minutes at such a rate that the reaction temperature never rose above −65°. After an additional 5 minutes stirring at −78°, 14.0 g (73.5 mmole) methyl indane-2-carboxylate was added dropwise at a rate that kept the reaction temperature less than −70° (20 minutes). After 1.0 hour at −78° the reaction mixture was allowed to warm to ambient temperature, neutralized with 20 ml acetic acid and rotary evaporated to a white gel. The gelatinous material was taken up in 50 ml water, the aqueous phase extracted with 75 ml portions of methylene chloride (4x), the combined organic extracts were backwashed (75 ml H$_2$O), dried (MgSO$_4$), and concentrated (water aspirator) to a crude residue and distilled, b.p. 150°–160° (0.1 mm) to give 17.0 g (86.4%) dimethyl 2-oxo-2-(2-indany)ethylphsphonate (2i).

The nmr spectrum (CDCl$_3$) of the distilled product exhibited a singlet at 7.15δ for the aromatic protons, a doublet at 3.76δ (J = 11 cps) for the OC$\underline{H}_3$, a singlet at 3.25δ for the benzylic protons, a doublet at 3.18δ (J = 23 cps) for the PC$\underline{H}_2$, and a deformed triplet at 3.13δ (J = 2 cps) for C$\underline{H}$CO.

EXAMPLE 92

2-[3α-p-Phenylbenzoyloxy-5α-hydroxy-2β-(3-oxo-3-(2-indanyl)-trans-1-propen-1-yl)-cyclopent-1α-yl]acetic acid, γ-lactone (3i)

To a solution, cooled in ice under nitrogen, of 17.2 ml (32.6 mmoles) of a 1.90M solution of n-butyllithium in hexane in 150 ml of dry 1,2-dimethoxyethane was added dropwise 9.2 g (34.5 mmoles) od dimethyl 2-oxo-2-(2-indanyl)ethylphosphonate (2i). The solution was stirred in the cold for 10 minutes then 11.9 g (33.5 mmoles) of the known 2-[3α-p-phenylbenzyloxy-5α-hydroxy-2β-formylcyclopent-1α-yl]acetic acid, γ-lactone was added. The ice bath was removed; the mixture was stirred for 1.0 hour then was quenched by the addition of glacial acetic acid (pH ~5). The mixture was concentrated and the resultant mixture was dissolved in methylene chloride (300 ml). The organic layer was washed with water (100 ml), saturated sodium bicarbonate (50 ml), and saturated brine (50 ml), was dried (anhydrous magnesium sulfate), and was concentrated to a semisolid. Recrystallization of the crude product from isopropyl alcohol:methylene chloride afforded the desired 2-[3α-p-phenylbenzoyloxy-5α-hydroxy-2β-(3-oxo-3-(2-indanyl)-trans-1-propen-1-yl) cyclopent-1α-yl]acetic acid, γ-lactone (3i) as white feathers melting at 170°–172° and weighing 6.85 g (42.8%).

The ir spectrum (CHCl$_3$) of the product exhibited adsorptions at 1775 cm$^{-1}$ for the lactone carbonyl, at 1710 cm$^{-1}$ for the ester carbonyl, 1670 and 1625 cm$^{-1}$ for the ketone carbonyl, and at 975 cm$^{-1}$ for the trans double bond.

EXAMPLE 93

2-(3α-p-Phenylbenzoyloxy-5α-hydroxy-2β-(3α-hydroxy-3-(2-indanyl)-trans-1-propen-1-yl)cyclopent-1α-yl)acetic acid, γ-lactone (4i) and 2-(3α-p-phenylbenzoyloxy-5α-hydroxy-3-(2-indanyl)-)-trans-1-propen-1-yl)cyclopent-1α-yl)acetic acid, γ-lactone (5i)

To a solution of 6.73 g (14.0 mmole) 2-(3α-p-phenylbenzoyloxy-5α-hydroxy-2β-(3-oxo-3-(2-indanyl)-trans-1-propen-1-yl)cyclopent-1αyl)acetic acid, γ-lactone (3i) in 67 ml dry tetrahydrofuran in a dry nitrogen atmosphere at ambient temperature was added dropwise 14.0 ml of a 0.5 M zinc borohydride solution. After stirring at room temperature for 1.5 hours, a saturated sodium bitartrate solution was added dropwise 14.0 ml of a 0.5 M zinc borohydride solution. After stirring at room temperature for 1.5 hours, a saturated sodium bitartrate solution was added dropwise, until hydrogen evolution ceased. The reaction mixture was allowed to stir for 5 minutes at which time 150 ml dry methylene chloride was added. After drying (MgSO$_4$) and concentrating (water aspirator) the resultant semisolid was purified by column chromatography on silica gel (Baker "Analyzed" Reagent 60-200 mesh) using mixtures of ethyl acetate:ether as eluents. After elution of less polar impurities a fraction containing 2.21 g (32.8% yield) 2-(3α-phenylbenzoyloxy-5α-hydroxy-2β-(3α-hydroxy-3-(2-indanyl)-trans-1-propen-1-yl)cyclopent-1α-yl)acetic acid, γ-lactone (4i) and a fraction containing 1.79 g (26.6% yield) of 2-(3α-p-phenylbenzoyloxy-5α-hydroxy-2β-(3β-hydroxy-3-(2-indanyl)-trans-1-propen-yl) cyclopent-1A-yl)acetic acid, lactone (5i) were collected.

EXAMPLE 94

2-[3α,5α-Dihydroxy-2β-(3α-hydroxy-3-(2-indanyl)-trans-1-propen-1-yl)cyclopen-1α-yl]acetic acid, γ-lactone (6i):

A heterogeneous mixture of 2.21 g (4.46 mmole) of 2-[3α-p-phenylbenzoyloxy-5α-hydroxy-2β-(3α-hydroxy-3-(2-indanyl)-trans-1-propen-1-yl)cyclopent-1α-yl]acetic acid, γ-lactone (4i), 40 ml of dry tetrahydrofuran, 40 ml of absolute methanol and 0.61 g of finely powdered, anhydrous potassium carbonate was stirred at room temperature for one hour, than cooled to 0°. To the cooled solution was added 4.46 ml of 1.0N aqueous hydrochloric acid. After stirring at 0° for an additional 10 minutes, 75 ml of water was added with concomitant formation of methyl p-phenylbenzoate which was collected by filtration. The filtrate was concentrated by rotary evaporation then was extracted with ethyl acetate (3x), the combined organic extracts were dried (MgSO), and were concentrated to give 924 mg (66%) of viscous, oily 2-[3α,5α-dihydroxy-2β-(3α- hydroxy-3-(2-indanyl)-trans-1-propen-1-yl)cyclopent-1α-yl]-acetic acid, γ-lactone (6i).

The ir spectrum (CHCl₃) exhibited a strong adsorption at 1770 cm⁻¹ for the lactone carbonyl and a medium adsorption at 970 cm⁻¹ for the trans double bond.

EXAMPLE 95

2-[5α-hydroxy-3α-(tetrahydropyran-2-yloxy)-2β-(3α-tetrahydropyran2-yloxy]-3-(2-indanyl)-trans-1-propen-1-yl)cyclopent-1α-yl]acetic acid, γ-lactone (7i)

To a solution of 0.924 g (2.94 mmole) 2-[3α,5α-dihydroxy-2β-(3α-hydroxy-3-(2-indanyl)-trans-1-propen-1-yl)cyclopent-1α-yl]acetic acid, γ-lactone (6i) in 49 ml anhydrous methylene chloride and 0.86 ml of 2,3-dihydropyran at 0° in dry nitrogen atmosphere was added a few crystals of p-toluenesulfonic acid, monohydrate. After stirring for 15 minutes, the reaction mixture was combined with 100 ml ether, the ether solution washed with saturated sodium bicarbonate (1 × 15 ml) then saturated brine (1 × 15 ml), dried (MgSO₄) and concentrated to yield 1.38 g (97.8%) crude 2-[5α-hydroxy-3α-(tetrahydropyran-2-yloxy)-2β-(3α-[tetrahydropyran-2-yloxy]-3-(2-indanyl)-trans-1-propen-1-yl)cyclopent-1α-yl]acetic acid, γ-lactone (7i) which was used without purification.

The ir spectrum (CHCl₃) of the product exhibited a strong adsorption at 1755 cm⁻¹ for the lactone carbonyl and a medium adsorption at 965 cm⁻¹ for the trans double bond.

EXAMPLE 96

2-[5α-Hydroxy-3α-(tetrahydropyran-2-yloxy)-2β-(3α-[tetrahydropyran-2-yloxy]-3-(2-indanyl)-trans-1-propen-1-yl)cyclopent-1α-yl]-acetaldehyde, γ-hemiacetal (8i)

A solution of 1.39 g (2.9 mmole) 2[5α-hydroxy-3α-(tetrahydropyran-2-yloxy)-2β- (3α-[tetrahydropyran-2-yloxy]-3-(2-indanyl)-trans-1-propen-1-yl)cyclopent-1α-yl]acetic acid, γ-lactone (7i) in 20 ml dry toluene was cooled to −78° in a dry nitrogen atmosphere. To this cooled solution was added 4.2 ml of 20% diisobutylaluminum hydride in n-hexane (Alfa Inorganics) dropwise at such a rate so that the internal temperature never rose above −65° (15 minutes). After an additional 30 minutes of stirring at −78°, anhydrous methanol was added until gas evolution ceased and the reaction mixture was allowed to warm to room temperature and was concentrated by rotary evaporation. The resultant oil was slurried in methanol then was filtered to remove aluminum salts. Concentration of the filtrate afforded the crude product which was purified by silica gel (Baker "Analyzed" 60-200 mesh) column chromatography using mixtures of benzene:ethyl acetate as elements. After removal of less polar impurities the desired 2-[5α-hydroxy-3α-(tetrahydropyran-2-yloxy)-2β-(3α-[tetrahydropyran-2-yloxy]-3-(2-indanyl)-trans-1-propen-1-yl)cyclopent-1α-yl]acetaldehyde, γ-hemiacetal (8i) as a viscous oil weighing 1.17 g (84.3%).

The ir spectrum (CHCl₃) of the purified product exhibited a medium absorption at 975 cm⁻¹ for the trans double bond and no carbonyl absorption.

EXAMPLE 97

9α-Hydroxy-11α,15α-bis-(tetrahydropyran-2-yloxy)-15-(2-indanyl)-cis-5-trans-13-ω-pentanorprostandienoic acid (9i)

To a solution of 3.21 g (7.24 mmole) (4-carbohydroxy-n-butyl)triphenylphosphonium bromide in a dry nitrogen atmosphere in 6.0 ml dry dimethyl sulfoxide was added 6.96 ml (14.0 mmole) of a 2.01M solution of sodium methylsulfinylmethide in dimetyl sulfoxide. To this red ylide solution was added dropwise a solution of 1.16 g (2.41 mmole) 2-[5α-hydroxy-3α-(tetrahydropyran-2-yloxy)-2β-(3α-[tetrahydropyran-2-yloxy]-3-(2-indanyl)-trans-1-propen-1-yl)cyclopent-1α-yl]acetaldehyde, γ-hemiacetal (8i) in 2.0 ml dry dimethyl sulfoxide over a period of 20 minutes. After an additional 2.0 hours stirring at room temperature, the reaction mixture was poured onto ice water. The basic aqueous solution was acidified to pH∼3 with 10% aqueous hydrochloric acid. The acidic solution was extracted with ethyl acetate (3x) and the combined organic extracts washed with water (2x), dried (MgSO₄) and evaporated to a solid residue. This solid residue was triturated with ether and filtered. The filtrate was concentrated to provide, 1.99 g (>100%) of 9α-hydroxy-11α,15α-bis-(tetrahydropyran-2-yloxy)-15-(2-indanyl)-cis-5-trans-13-ω-pentanorprostadienoic acid (9i) which was used without further purification.

The ir spectrum (CHCl₃) of the purified product exhibited a strong absorption at 1710 cm⁻¹ for the acid carbonyl and a medium absorption at 970 cm⁻¹ for the trans double bond.

EXAMPLE 98

9α,11α,15α-trihydroxy-15-(2-indanyl)-cis-5-trans-13-ω-pentanorprostadienoic acid (12i)

A solution of 602 mg 9α-hydroxy-11α,15α-bis-(tetrahydropyran-2-yloxy)-15-(2-indanyl)-cis-5-trans-13-ω-pentanorprostadienoic acid (9i) in 10 ml of a 65:35 mixture of glacial acetic acid:water was stirred under nitrogen at room temperature for 18 hours then was concentrated by rotary evaporation. The resultant crude oil was purified by column chromatography on silica gel (Mallinckrodt CC-7 100-200 mesh) using mixtures of chloroform:ethyl acetate as eluents. After elution of less polar impurities the 9α,11α,15α-trihydroxy-15-(2-indanyl)-cis-5-trans-13-ω-trinorprostadienoic acid (12i) was collected as a white solid weighing 156 mg (39%) and melting at 114°-115° (from ethyl acetate).

The ir spectrum (KBr) of the product exhibited a strong absorption at 5.77 μ for the acid carbonyl and a medium absorption at 10.25 μ for the trans double bond.

EXAMPLE 99

9-Oxo-11α,15α-bis-(tetrahydropyran-2-yloxy)-15-(2-indanyl)-cis-5-trans-13-ω-pentanorprostadienoic acid (10i)

To a solution cooled to −10° under nitrogen of 1.32 g (2.34 mmole) 9α-hydroxy-11α,15α-bis-(tetrahydropyran-2-yloxy)-15-(2-indanyl)-cis-5-trans-13-ω-pentanorprostadienoic acid (9i) in 15 ml reagent grade acetone was added dropwise to 1.17 ml of Jones' reagent. After 15 minutes at −10°, 1.17 ml 2-propanol was added and the reaction mixture was allowed to stir an additional 5 minutes at which time it was combined with ethyl acetate, washed with water (2x), dried (MgSO₄) and concentrated to give 1.11 g (84.2%) of 9-oxo-11α,15α-bis-(tetrahydropyran-2-yloxy)-15-(2-indanyl)-cis-5-trans-13-ω-pentanorprostadienoic acid (10i) which was used without purification.

EXAMPLE 100

9-Oxo-11α,15α-dihydroxy-15-(2-indanyl)-cis-5-trans-13-ω-pentanorprostadienoic acid (11i)

A solution of 1.11 g 9-oxo-11α,15α-bis-(tetrahydropyran-2-yloxy)-15-(2-indanyl)-cis-5-trans-13-ω-pentanorprostadienoic acid (10i) in 15 ml of a 65:35 mixture of glacial acetic acid:water was stirred under nitrogen at room temperature for 18 hours then was concentrated by rotary evaporation. The resultant crude oil was purified by column chromatography on silica gel (Mallinckrodt CC-4 100–200 mesh) using mixtures of chloroform:ethyl acetate as eluents. After elution of less polar impurities the 9-oxo-11α,15α-dihydroxy-15-(2-indanyl)-cis-5-trans-β-ω-pentanorprostadienic acid (11i) was collected as a white solid weighing 288 mg (37%) and melting at 110°–112° (from ethyl acetate:hexane).

The ir spectrum (KBr) of the product exhibited strong absorptions at 5.68 μ for the ketone carbonyl and at 5.84 μ for the acid carbonyl and a medium absorption at 10.25 μ for the trans double bond.

EXAMPLE 101 p-Biphenyl-9-oxo-11α,15α-dihydroxy-15-(2-indanyl)-cis-5-trans-13-Ω-pentanorprostadienoate To a mixture of 60 mg (0.15 mmole) of 9-oxo-11α,15α-dihydroxy-15-(2-indanyl)-cis-5-trans-13-ω-pentanorprostadienoic acid (11i) and 255 mg (1.5 mmoles) of p-phenylphenol in 6 ml of dry methylene chloride was added 1.65 ml of a 0.1M solution of dicyclohexylcarbodiimide in methylene chloride. The mixture was stirred at room temperature for 16 hours under nitrogen then was concentrated. The solid residue was purified by silica gel (Baker "Analyzed" 60-200 mesh) chromatography using mixtures of chloroform:ethyl acetate as eluents. After removal of less polar impurities the solid p-biphenyl 9-oxo-11α,15α-dihydroxy-15-(2-indanyl)-cis-5-trans-13-ω-pentanorprostadienoate was collected weighing 43 mg and melting at 130°–104.5° (from methylene chloride: hexane).

The ir spectrum (KBr) of the product exhibited strong adsorptions at 5.65 μ for the ketone carbonyl and 5.70 μ for the ester carbonyl and a medium absorption at 10.35 μ for the trans double bond.

EXAMPLE 102 p-Biphenyl 9α,11α,15α-trihydroxy-15-(2-indanyl)-cis-5-trans-13-ω-pentanorprostadienoate To a mixture of 60 mg (0.15 mmole) of 9α,11α,15α-trihydroxy-15-(2-indanyl)-cis-5-trans-13-ω-pentanorprostadienoate (12i) and 255 mg (1.5 mmoles) of p-phenylphenol in 6 ml of dry methylene chloride was added 1.65 ml of a 0.1M solution of dicyclohexylcarbodiimide in methylene chloride. The mixture was stirred for 16 hours at room temperature under nitrogen then was concentrated. Purification of the solid residue by silica gel (Baker "Analzed" 60-200 mesh) chromatography using mixtures of chloroform-ethyl acetate as elements after removal of less polar impurities the solid p-biphenyl 9α,11α,15α-trihydroxy-15-(2-indanyl)-cis-5-trans-13-ω-pentanorprostadienoate weighing 41 mg and melting at 134°–135° (from methylene chloride:hexane).

The ir spectrum (KBr) of the product exhibited a strong absorption at 5.68 μ for the ester carbonyl and a medium absorption at 10.35 μ for the trans double bond.

EXAMPLE 103

N-Methanesulfonyl 9α-hydroxy-11α,15α-bis-(tetrahydropyran-2-yloxy)-15-(2-indanyl)-cis-5-trans-13-ω-pentanorprostadienamide (9i)

To a solution of 2.37 g (4.56 mmole) (methanesulfonylaminocarbonyl-n-butyl)triphenylphosphonium bromide in a dry nitrogen atmosphere in 5.0 ml dry dimethyl sulfoxide was added 4.50 ml (8.62 mmole) of a 1.90M solution of sodium methylsulfinylmethide in dimethyl sulfoxide. To this red ylide solution was added dropwise a solution of 735 mg (1.52 mmole) 2-[5α-hydroxy-3α-(tetrahydropyran-2-yloxy)-2β-(3α-[tetrahydropyran-2-yloxy]-3-(2-indanyl)-trans-1-propen-1-yl)cyclopent-1α-yl]acetaldehyde, γ-hemiacetal (8i) in 6.0 ml dry dimethyl sulfoxide. After an additional 1 hour stirring at room temperature, the reaction mixture was poured onto ice water. The basic aqueous solution was acidified to pH~3 with 10% aqueous hydrochloric acid. The acidic solution was extracted with ethyl acetate (3x) and the combined organic extracts washed once with water (10 ml), dried (MgSO4) and evaporated to a solid residue. The crude product was purified by column chromatography on silica gel (Baker "Analyzed" Reagent 60-200 mesh) using mixtures of chloroform: ethyl acetate as eluents. After removal of high Rf impurities, 899 mg (81.5%) of N-methanesulfonyl 9α-hydroxy-11α,15α-bis-(tetrahydropyran-2-yloxy)-15-(2-indanyl)-cis-5-trans-13-ω-pentanorprostadienamide (9i) was collected.

The ir spectrum (CHCl3of the product exhibited medium absorptions at 1710 cm$^{-1}$ for the carbonyl group and at 970 cm$^{-1}$ for the trans double bond.

EXAMPLE 104

N-Methanesulfonyl 9α,11α,15α-trihydroxy-15-(2-indanyl)-cis-5-trans-13-ω-pentanorprostadienamide (12i)

A solution of 500 mg N-methanesulfonyl 9α-hydroxy-11α,15α-bis-(tetrahydropyran-2-yloxy)-15-(2-indanyl)-cis-5-trans-13-ω-pentanorprostadienamide (9i) in 10 ml of 65:35 mixture of glacial acetic acid-water was stirred under nitrogen at room temperature for 18 hours then was concentrated by rotary evaporation. The resultant crude oil was purified by column chromatography on silica gel (Mallinckrodt CC7 100–200 mesh) using mixtures of chloroform-ethyl acetate as eluents. After elution of less polar impurities the N-methanesulfonyl 9α,11α,15α-trihydroxy-15-(2-indanyl)-cis-5-trans-13-ω-pentanorprostadienamide (12i) was collected as a viscous oil weighing 257 mg (69.6%).

The ir spectrum (CHCl3) of the product exhibited a strong absorption at 1705 cm$^{-1}$ for the carbonyl group and a medium absorption at 965 cm$^{-1}$ for the trans double bond.

EXAMPLE 105

N-Methanesulfonyl 9-oxo-11α,15α-bis-(tetrahydropyran-2-yloxy)-15-(2-indanyl)-cis-5-trans-13-ω-pentanorprostadienamide (10i)

To a solution cooled to −10° under nitrogen of 399 mg (0.62 mmole) of N-methanesulfonyl 9α-hydroxy-11α,15α-bis-(tetrahydropyran-2-yloxy)-15-(2-indanyl)-cis-5-trans-13-ω-pentanorprostadienamide (9i) in 15 ml reagent grade acetone was added dropwise to 0.31 ml of Jones' reagent. After 15 minutes at −10°, 0.31 ml 2-propanol was added and the reaction mixture was allowed to stir an additional 5 minutes at which time it was combined with ethyl acetate, washed with water (2x), dried (MgSO$_4$) and concentrated to give 371 mg (93%). N-methanesulfonyl 9-oxo-11α,15α-bis-(tetrahydropyran-2-yloxy)-15-(2-indanyl)-cis-5-trans-13-ω-pentanorprostadienamide (10i) which was used withot purification.

EXAMPLE 106

N-Methanesulfonyl 9-oxo-11α,15α-dihydroxy-15-(2-indanyl)-cis-5-trans-13-ω-pentanorprostadienamide (11i).

A solution of 371 mg N-methanesulfonyl 9-oxo-11α,15α-bis-(tetrahydropyran-2-yloxy)-15-(2-indanyl)-cis-5-trans-13-ω-pentanorprostadienamide (10i) in 10 ml of a 65:35 mixture of glacial acetic acid:water was stirred under nitrogen at room temperature for 16 hours then was concentrated by rotary evaporation. The resultant crude oil was purified by column chromatography on silica gel (Mallinckrodt CC-7 100–200 mesh) using mixtures of chloroform:ethyl acetate eluents. After elution of less polar impurities the N-methanesulfonyl 9-oxo-11α,15α-dihydroxy-15-(2-indanyl)-cis-5-trans-13-ω-pentanorprostadienamide (11i) was collected as viscous oil weighing 65 mg (23.8%).

The ir spectrum (CHCl$_3$) of the product exhibited strong absorptions at 1740 cm$^{-1}$ for the ketone carbonyl, 1720 cm$^{-1}$ for the sulfonimide carbonyl, and at 970 cm$^{-1}$ for the trans double bond.

EXAMPLE 107

2-Descarboxy-2-(tetrazol-5-yl)-9α-hydroxy-11α,15α-bis-(tetrahydropyran-2-yloxy)-15-(2-indanyl)-cis-5-trans-13-ω-pentanorprostadienoic acid (9i)

To a solution of 2.12 g (4.56 mmole) (4-tetrazol-5-yl)-n-butyl)triphenylphosphonium bromide in a dry nitrogen atmosphere in 5.0 ml dry dimethyl sulfoxide was added 4.54 ml (8.62 mmole) of a 1.90M solution of sodium methylsulfinylmethide in dimethyl sulfoxide. To this red ylide solution was added dropwise a solution of 735 mg (1.52 mmole) 2-[5α-hydroxy-3α-(tetrahydropyran-2-yloxy)-2β-(3α-[tetrahydropyran-2-yloxy]-3-(2-indanyl)-trans-1-propen-1-yl)cyclopent-1α-yl]acetaldehyde, γ-hemiacetal (8i) in 6.0 ml dry dimethyl sulfoxide over a period of 20 minutes. After an additional 16 hours stirring at room temperature, the reaction mixture was poured onto ice water. The basic aqueous solution was extracted with ethyl acetate (3x) and the combined organic extracts washed once with water (10 ml), dried (MsSO$_4$) and evaporated to a solid residue. The crude product was purified by column chromatography on silica gel (Baker "Analyzed" Reagent 60–200 mesh) using mixtures of chloroform:ethyl acetate as eluents. After removal of high R$_f$ impurities, 878 mg (100%) of 2-descarboxy-2-(tetrazol-5-yl)-9α-hydroxy-11α,15α-bis-(tetrahydropyran-2-yloxy)-15-(2-indanyl)-cis-5-trans-13-ω-pentanorprostadienoic acid (9i) was collected.

The ir spectrum (CHCl$_3$) of the product exhibited a medium absorption at 970 cm$^{-1}$ for the trans double bond.

EXAMPLE 108

2-Descarboxy-2-(tetrazol-5-yl)-9α,11α,15α-trihydroxy-15-(2-indanyl)-cis-5-trans-13-ω-pentanorprostadienoic acid (12i)

a solution of 500 mg 2-descarboxy-2-(tetrazol-5-yl)-9α-hydroxy-11α,15α-bis-(tetrahydropyran-2-yloxy)-15-(2-indanyl)-cis-5-trans-13-ω-pentanorprostadienoic acid (9i) in 10 ml of a 65:35 mixture of glacial acetic acid:water was stirred under nitrogen at room temperature for 15 hours then was concentrated by rotary evaporation. The resultant crude oil was purified by column chromatography on silica gel (Mallinckrodt CC-7 100–200 mesh) using mixtures of chloroform-ethyl acetate as eluents. After elution of less polar impurities the 2-descarboxy-2-(tetrazol-5-yl)-9α,11α,15α-dihydroxy-15-(2-indanyl)-cis-5-trans-13-ω-pentanorprostadienoic acid (12i) was collected as a solid weighing 146 mg (39.7%) which melted at 125°–126° (from ethyl acetate:hexane).

The ir spectrum (KBr) of the product exhibited a strong absorption at 10.25 μ for the trans double bond.

EXAMPLE 109

2-Descarboxy-2-(tetrazol-5-yl)-9-oxo-11α,15α-dihydroxy-15-(2-indanyl)-cis-5-trans-13-ω-pentanorprostadienoic acid (10i)

A solution of 352 mg 2-descarboxy-2-(tetrazol-5-yl)-9-oxo-11α,15α-bis-(tetrahydropyran-2-yloxy)-15-(2-indanyl)-cis-5-trans-13-ω-pentanorprostadienoic acid (9i) in 10 ml of a 65:35 mixture of glacial acetic acid:water was stirred under nitrogen at room temperature for 16 hours then was concentrated by rotary evaporation. The resultant crude oil was purified by column chromatography on silica gel (Mallinckrodt CC-7 100–200 mesh) using mixtures of chloroform-ethyl acetate as eluents. After elution of less polar impurities the 2-descarboxy-2-(tetrazol-5-yl)-9-oxo-11α,15α-dihydroxy-15-(2-indanyl)-cis-5-trans-13-ω-pentanorprostadienoic acid (10i) was collected as a viscous oil weighing 83 mg (31.0%).

The ir spectrum (CHCl$_3$) of the product exhibited a strong absorption at 1740 cm$^{-1}$ for the ketone carbonyl and a medium absorption at 970 cm$^{-1}$ for the trans double bond.

EXAMPLE 110

2-Descarboxy-2-(tetrazol-5-yl)-9-oxo-11α,15α-bis-(tetrahydropyran-2-yloxy)-15-(2-indanyl)-cis-5-trans-13-ω-pentanorprostadienoic acid (11i)

To a solution cooled to −10° under nitrogen of 378 mg (0.65 mmole) 2-descarboxy-2-(tetrazol-5-yl9-9α-hydroxy-11α,15α-bis-(tetrahydropyran-2-yloxy)-15(2-indanyl)-cis-5-trans-13-ω-pentanorprostadienoic acid (10i) in 15 ml reagent grade acetone was added dropwise to 0.33 ml of Jones' reagent. After 15 minutes at −10°, 0.33 ml 2-propanol was added and the reaction mixture was allowed to stir an additional 5 minutes at which time it was combined with ethyl acetate, washed with water (2x), dried (MGSO$_4$), and concentrated to give 352 mg (93%) of 2-descarboxy-2-(tetrazol)-5-yl)-9- oxo-11α,15α-bis-(tetrahydropyran-2-yloxy)-15-(2-indanyl)-cis-5-trans-13-ω-pentanorprostadienoic acid (11i) which was used without purification.

EXAMPLE 111

2-[3α,5α-dihydroxy-2β-(3β-hydroxy-3-(2-indanyl)-trans-1-propen-1-yl)-cyclopent-1α-yl]acetic acid, γ-lactone (6i)

A heterogeneous mixture of 1.79 g (3.62 mmole) of 2-[3α-p-phenylbenzoxyloxy-5α-hydroxy-2β-(3β-hydroxy-3-(2-indanyl)-trans-1-propen-1-yl)-cyclopent-1α-yl]acetic acid, γ-lactone (5i), 10 ml of dry tetrahydrofuran, 25 ml of absolute methanol, and 0.50 g of finely powdered, anhydrous potassium carbonate was stirred at room temperature for 2.75 hours, then cooled to 0°. To the cooled solution was added 3.62 ml of 1.0N aqueous hydrochloride acid. After stirring at 0° for an additional 10 minutes, 50 ml of water was added with concomitant formation of methyl p-phenylbenzoate which was collected by filtration. The filtrate was concentrated by rotary evaporation, was extracted with ethyl acetate (3x), the combined organic extracts were dried (MsSO$_4$), and were concentrated to give 0.90 g (79% of viscous, oily-2-[3α,5α-dihydroxy-2β-(3β-hydroxy-3-(2-indanyl)-trans-1-propen-1-yl)cyclopent-1α-yl]acetic acid, γ-lactone (6i).

The ir spectrum (CHCl$_3$) exhibited a strong adsorption at 1770 cm$^{-1}$ for the lactone carbonyl and a medium absorption at 970 cm$^{-1}$ for the trans double bond.

EXAMPLE 112

2-[5α-hydroxy-3α-(tetrahydropyran-2-yloxy)-2β-(3β-[tetrahydropyran-2-yloxy]-3-(2-indanyl)-trans-1-propen-1-yl)cyclopent-1α-yl]acetic acid, γ-lactone (7i)

To a solution of 0.892 g (2.84 mmole) 2-[3α,5α-dihydroxy-2β-(3β-hydroxy-3-(2-indanyl)-trans-1-propen-1-yl)cyclopent-1α-yl]-acetic acid, γ-lactone (6i) in 10 ml anhydrous methylene chloride and 0.84 ml of 2,3 dihydropyran at 0° in a dry nitrogen atmosphere was added a few crystals of p-toluenesulfonoc acid, monohydrate. After stirring for 10 minutes, the reaction mixture was combined with 100 ml ether, the ether solution washed with saturated sodium bicarbonate (1 × 15 ml) then saturated brine (1 × 15 ml), dried (MgSO$_4$) and concentrated to yield 1.34 g (>99%) crude 2-[5α-hydroxy-3α-(tetrahydropyran-2-yloxy)-2β-(3β-tetrahydropyran-2-yloxy]-3-(2-indanyl)-trans-1-propen-yl)cyclopent-1α-yl]acetic acid, γ-lactone (7i) which was used without purification.

The ir spectrum (CHCl$_3$) of the product exhibited a strong absorption at 1765 cm$^{-1}$ for the lactone carbonyl and a medium absorption at 970 cm$^{-1}$ for the trans double bond.

EXAMPLE 113

2-[5α-Hydroxy-3α-(tetrahydropyran-2-yloxy)-2β-(3β-[tetrahydropyran-2-yloxy]-3-(2-indanyl)-trans-1-propen-1-yl)cyclopent-1α-yl]acetaldehyde, γ-hemiacetal (8'i)

A solution of 1.35 g (2.82 mmole) 2-[5α-hydroxy-3α-(tetrahydropyran-2-yloxy)-2β-(3β-[tetrahydropyran-2-yloxy]-3-(2-indanyl)-trans-1-propen-1-yl)cyclopent-1α-yl]acetic acid, γ-lactone (7'i) in 20 ml dry toluene was cooled to −78° in a dry nitrogen atmosphere. To this cooled solution was added 4.2 ml of 20% diisobutylaluminum hydride in n-hexane (Alfa Inorganics) dropwise at such a rate so that the internal temperature never rose above −65° (15 minutes). After an additional 30 minutes of stirring at −78°, anhydrous methanol was added until gas evolution ceased and the reaction mixture was allowed to warm to room temperature and was concentrated by rotary evaporation. The resultant oil was slurried in methanol then was filtered to remove aluminum salts. Concentration of the filtrate afforded the crude product which was purified by silica gel (Baker "Analyzed" 60-200 mesh) column chromatography using mixtures of benzene:ethyl acetate as elements. After removal of less polar impurities the desired 2-[5α-hydroxy-3α-(tetrahydropyran-2-yloxy)-2β-(3β-[tetrahydropyran-2-yloxy]-3-(2-indanyl)-trans-1-propen-1-yl)cyclopent-1α-yl]acetaldehyde, γ-hemiacetal (8'i) as a viscous oil weighing 1.27 g (94.0%).

The ir spectrum (CHCl$_3$) of the purified product exhibited a medium absorption at 975 cm$^{-1}$ for the trans double bond and no carbonyl absorption.

EXAMPLE 114

9α-Hydroxy-11α,15β-bis-(tetrahydropyran-2-yloxy)-15-(2-indanyl)-cis-5-trans-13-ω-pentanorprostadienoic acid (9'i)

To a solution of 3.48 g (7185 mmole) (4-carbohydroxy-n-butyl)triphenylphosphonium bromide in a dry nitrogen atmosphere in 7.0 ml dry dimethyl sulfoxide was added 7.56 ml (15.2 mmole) of a 2.01M solution of sodium methylsufinylmethide in dimethyl sulfoxide. To this red ylide solution was added dropwise a solution of 1.27 g (2.62 mmole) 2-[5α-hydroxy-3α-(tetrahydropyran-2-yloxy)-2β-(3β-[tetrahydropyran-2-yloxy]-3-(2-indanyl)-trans-1-propen-1-yl)cyclopent-1α-yl]acetaldehyde, γ-hemiacetal (8'i) in 3.0 ml dry dimethyl sulfoxide over a period of 20 minutes. After an addition 2.0 hours stirring at room temperature, the reaction mixture was poured onto ice water. The basic aqueous solution was acidified to pH~3 with 10% aqueous hydrochloric acid. The acidic solution was extracted with ethyl acetate (3x) and the combined organic extracts washed with water (2x), dried (MgSO$_4$) and evaporated to a solid residue. This solid residue was triturated with ether and filtered. The filtrate was concentrated to afford, 2.03 g (>100%) of 9α-hydroxy-11α,15β-bis-(tetrahydropyran-2-yloxy)-15-(2-indanyl)-cis-5-trans-13-ω-pentanorprostadienoic acid (9'i) which was used without further purification.

The ir spectrum (CHCl$_3$) of the purified product exhibited a strong absorption at 1705 cm$^{-1}$ for the acid carbonyl and a medium absorption at 970 cm$^{-1}$ for the trans double bond.

EXAMPLE 115

9α,11α,15β-trihydroxy-15-(2-indanyl)-cis-5-trans-13-ω-pentanorprostadienoic acid (12'i)

A solution of 677 mg 9α-hydroxy-11α,15β-bis-(tetrahydropyran-2-yloxy)-15-(2-indanyl)-cis-5-trans-13-ω-pentanorprostadienoic acid (9'i) in 11 ml of a 65:35 mixture of glacial acetic acid:water was stirred under nitrogen at room temperature for 18 hours then was concentrated by rotary evaporation. The resultant crude oil was purified by column chromatography on silica gel (Mallinckrodt CC-7 100-200 mesh) using mixtures of chloroform-ethyl acetate as eluents. After elution of less polar impurities the 9α,11α,15β-trihydroxy-15-(2-indanyl)-cis-5-trans-13-ω-pentanorprostadienoic acid (12'i) was collected as a viscous oil weighing 148 mg (31%).

The ir spectrum (CHCl₃) of the product exhibited a strong absorption at 1712 cm⁻¹ for the acid carbonyl and a medium absorption at 975 cm⁻¹ for the trans double bond.

EXAMPLE 116

9-Oxo-11α,15β-bis-(tetrahydropyran-2-yloxy)-15-(2-indanyl)-cis-5-trans-13-ω-pentanorprostadienoic acid (10′i)

To a solution cooled to −10° under nitrogen of 1.35 g (2.39 mmole) 9α-hydroxy-11α,15β-bis-(tetrahydropyran-2-yloxy)-15-(2-indanyl)-cis-5-trans-13-ω-pentanorprostadienoic acid (9′i) in 15 ml reagent grade acetone was added dropwise to 1.36 ml of Jones' reagent. After 20 minutes at −10°, 1.36 ml 2-propanol was added and the reaction mixture was allowed to stir an additional 5 minutes at which time it was combined with ethyl acetate, washed with water (2x), dried (MgSO₄) and concentrated to give 1.14 g (84.5%) of 9-oxo-11α,15β-bis-(tetrahydropyran-2-yloxy)-15-(2-indanyl)-cis-5-trans-13-ω-pentanorprostadienoic acid (10′i) which was used without purification.

EXAMPLE 117

9-Oxo-11α,15β-dihydroxy-15-(2-indanyl)-cis-5-trans-13-ω-pentanorprostadienoic acid (11′i)

A solution of 1.14 g 9-oxo-11α,15β-bis-(tetrahydropyran-2-yloxy)-15-(2-indanyl)-cis-5-trans-13-ω-pentanorprostadienoic acid (10′i) in 15 ml of a 65:35 mixture of glacial acetic acid:water was stirred under nitrogen at room temperature for 18 hours then was concentrated by rotary evaporation. The resultant crude oil was purified by column chromatography on silica gel (Mallinckrodt CC-4 100-200 mesh) using mixtures of chloroform:ethyl acetate as eluents. After elution of less polar impurities the 9-oxo-11α,15β-dihydroxy-15-(2-indanyl)-cis-5-trans-13-ω-pentanorprostadienoic acid (11′i) was collected as a viscous oil weighing 296 mg (36.9%).

The ir spectrum (CHCl₃) of the product exhibited strong absorptions at 1740 cm⁻¹ for the ketone carbonyl and at 1710 cm⁻¹ for the acid carbonyl and a medium absorption at 970 cm⁻¹ for the trans double bond.

EXAMPLE 118 p-Biphenyl 9-oxo-11α,15β-dihydroxy-15-(2-indanyl)-cis-5-trans-1,3-ω-pentanorprostadienoate To a mixture of 60 mg (0.15 mmole) of 9-oxo-11α,15β-dihydroxy-15-(2-indanyl)-cis-5-trans-13-ω-pentanorprostadienoate (11′i) and 255 mg (1.5 mmoles) of p-phenylphenol in 6 ml of dry methylene chloride was added 1.65 ml of a 0.1M solution of dicyclohexylcarbodiimide in methylene chloride. The mixture was stirred for 16 hours at room temperature under nitrogen then was concentrated. Purification of the solid residue by silica gel (Baker "Analyzed" 60-200 mesh) chromatography using mixtures of chloroform-ethyl acetate as elements after removal of less polar impurities the solid p-biphenyl 9-oxo-11α,15β-dihydroxy-15-(2-indanyl)-cis-5-trans-3-ω-pentanorprostadienoate weighing 34 mg and melting at 98°-100° (from methylene chloride:hexane).

The ir spectrum (KBr) of the product exhibited strong absorptions at 5.66 μ for the ketone carbonyl at 5.77 μ for the ester carbonyl and a medium absorption at 10.35 μ for the trans double bond.

EXAMPLE 119 p-Biphenyl 9α,11α,15β-trihydroxy-15-(2-indanyl)-cis-5-trans-13-ω-pentanorprostadienoate To a mixture of 60 mg (0.15 mmole) of 9α,11α,15α-trihydroxy-15-(2-indanyl)-cis-5-trans-13-ω-pentanorprostadienoate (12′i) and 255 mg (1.55 mmoles) of p-phenylphenol in 6 ml of dry methylene chloride was added 1.65 ml of 0.1M solution of dicyclohexylcarbodiimide in methylene chloride. The mixture was stirred for 16 hours at room temperature under nitrogen then was concentrated. Purification of the solid residue by silica gel (Baker "Analyzed" 60-200 mesh), chromatography using mixtures of chloroform:ethyl acetate as elements after removal of less polar impurities the solid p-biphenyl 9α,11α,15β-trihydroxy-15-(2-indanyl)-cis-5-trans-13-ω-pentanorprostadienoate weighing 40 mg and melting at 98°-100° (from methylenechloride:hexane).

The ir spectrum (KBr) of the product exhibited a strong absorption at 5.65 μ for the ester carbonyl and a medium absorption at 10.20 μ for the trans double bond.

EXAMPLE 120

2-Carboethoxy-2-carbo-t-butoxy-5,6-dimethyoxyindane

To a suspension, stirred under nitrogen, of 12.9 g (306 mmoles) of a 57% sodium hydride suspension in 280 ml of dry tetrahydrofuran was added dropwise 28.8 g (153 mmoles) of ethyl t-butyl malonate. After the addition was completed the solution was stirred for an additional 20 minutes, then 2.49 g (15 mmoles) of potassium iodide followed by a solution of 36.0 g (153 mmoles) of 1,2-dimethoxy-4,5-bis-chloromethylbenzene in 180 ml of dry tetrahydrofuran was added. The mixture was heated at reflux for 2.5 hours, was let cool, and was concentrated by rotary evaporation. The resultant slurry was dissolved in methylene chloride (300 ml), was washed with water (2 × 100 ml), was dried (anhydrous magnesium sulfate) and was concentrated to provide the desired, crystalline 2-carboethoxy-2-carbo-t-butoxy-5,6-dimethoxyindane weighing 46.2 g (86.2%) and melting at 70°-73° (from ether).

The ir spectrum (KBr) of the recrystallized product exhibited a strong absorption at 5.77 μ for the carbonyl groups.

EXAMPLE 121

2-Carboxy-5,6-dimethoxyindan-2-carboxylic acid

A solution of 46.2 g (132 mmoles) or 2-carboethoxy-2-carbo-t-butoxy-5,6-dimethoxyindane and 2.25 g (13.2 mmoles) of p-toluenesulfonic acid monohydrate in 460 ml of benzene was heated at reflux using a Deans-Stark trap for 4 hours. The solution was let cool, was washed with water (3 × 50 ml), was dried (anhydrous magnesium sulfate), and was concentrated to provide the desired, crystalline 2-carboethoxy-5,6-dimethoxyindan-2-carboxylic acid weighing 38.9 g 100%) and melting at 146°-148° (from ethyl acetate:cyclohexane).

The ir spectrum (KBr) of the recrystallized product exhibited strong absorptions at 5.77 μ for the ester carbonyl and 5.67 μ for the acid carbonyl.

EXAMPLE 122

Ethyl 5,6-dimethoxyindan-2-carboxylate

A 46.8 g (159 mmole) portion of 2-carboethoxy-5,6-dimethoxyindan-2-carboxylic acid was heated (oil bath 200°–210°) under reduced pressure (oil pump). The desired ethyl 5,6-dimethoxyindan-2-carboxylate was collected by distillation weighing 29.6 g (74.6%); b.p. 170°–176° at 1.0 mm; m.p. 46°–48°.

The ir spectrum (KBr) of the product exhibited a strong absorption at 5.75 μ for the ester carbonyl.

EXAMPLE 123

Dimethoxy 2oxo-3-(5,6-dimethoxyindanyl))butylphosphonate (2j)

A solution of 29.4 g (237 mmoles) dimethyl methylphosphonate (Aldrich) in 300 ml dry tetrahydrofuran was cooled to −78° in a dry nitrogen atmosphere. To the stirred phosphonate solution was added 109 ml of 2.25M n-butyllithium in hexane solution (Alfa Inorganics, Inc.) dropwise over a period of 20 minutes at such a rate that the reaction temperature never rose above −65°. After an additional 5 minutes stirring at −78°, 29.6 g (118 mmole) ethyl 5,6-dimethoxyindanyl-2-carboxylate was added dropwise at a rate that kept the reaction temperature less than −70° (20 minutes). After 1.0 hour at −79° the reaction mixture was allowed to warm to ambient temperature, neutralized with 15 ml acetic acid and rotary evaporated to a white gel. The gelatonous material was taken up in 50 ml water, the aqueous phase extracted with 100 ml portions of methylene chloride (4x), the combined organic extracts were backwashed (100 ml H$_2$O), dried (MgSO$_4$), and concentrated (water aspirator) to a crude residue and distilled, b.p. 240°–243° (0.2 mm) to give 24.3 g (62.7%) dimethyl 2-oxo-3-(2-(5,6-dimethoxyindanyl))ethylphosphonate (2j).

The nmr spectrum (CDCl$_3$) of the distilled product exhibited a singlet at 6.73δ for the aromatic protons, a doublet at 3.78δ (J=23cps) for the CH$_2$ P, a singlet at 3.84δ for the OCH$_3$, a doublet at 3.22δ (J=11cps) for the POCH$_3$, and multiplets at 3.06–3.28δ for the remaining protons.

EXAMPLE 124

2-[3α-p-Phenylbenzoyloxy-5α-hydroxy-2β-(3-oxo-3-(2-(5,6-dimethoxyindanyl))-trans-1-propen-1-yl)cyclopent-1α-yl]acetic acid, γ-lactone (3j)

To a solution, cooled in ice under nitrogen, of 14.7 ml (33.0 mmoles) of a 2.25M solution of n-butyllithium in hexane in 100 ml of dry tetrahydrofuran was added dropwise 11.8 g (36.0 mmoles) of dimethyl 2-oxo-3-(2-(5,6-dimethoxyindanyl))ethylphosphonate (2j). The solution was stirred in the cold for 10 minutes then a slurry of 10.5 g (30.0 mmoles) of the known 2-[3α-p-phenylbenzoyloxy-5α-hydroxy-2β-formylcyclopent-1α-yl]acetic acid, γ-lactone in 150 ml of dry tetrahydrofuran was added. The ice bath was removed; the mixture was stirred for 50 minutes then was quenched by the addition of glacial acetic acid (ph∼5). The mixture was concentrated and the resultant mixture was dissolved in methylene chloride (150 ml). The organic layer was washed with water (75 ml), saturated sodium bicarbonate (30 ml), and saturated brine (30 ml), was dried (anhydrous magnesium sulfate), and was concentrated to a solid. Recrystallization of the crude product from acetone afforded the desired 2-[3α-p-phenylbenzoyloxy-5α-hydroxy-2β-(3-oxo-3-(2-(5,6-dimethoxyindanyl))-trans-1-propen-1-yl)cyclopent-1α-yl]acetic acid, γ-lactone (3j) which melted at 178°–180° and weighed 11.6 g (70.4%).

The ir spectrum (CHCl$_3$) of the product exhibited absorptions at 1775 cm$^{-1}$ for the lactone carbonyl, at 1710 cm$^{-1}$ for the ester carbonyl, 1700 and 1630 cm$^{-1}$ for the ketone carbonyl, and at 975 cm$^{-1}$ for the trans double bond.

EXAMPLE 125

2-[3α-p-Phenylbenzoyloxy-5α-hydroxy-2β-(3α-hydroxy-3-(2-(5,6-dimethoxyindanyl))-trans-1-propen-1-yl)cyclopent-1α-yl]acetic acid, γ-lactone (4j) and 2-[3α-p-phenylbenzoyloxy-5α-hydroxy-2β-(3β-hydroxy-3-(2-(5,6-dimethoxyindanyl))-trans-1-propen-1-yl)cyclopent-1α-yl]acetic acid, γ-lactone (5j)

To a solution, cooled to −45° under nitrogen, of 11.6 g (21.1 mmoles) of 2-[3α-p-phenylbenzoyloxy-5α-hydroxy-2β-(3-oxo-3-(2-(5,6-dimethoxyindanyl))-trans-1-propen-1-yl)cyclopent-1α-yl]acetic acid, γ-lactone (3j) in 300 ml of dry tetrahydrofuran was added dropwise 31.0 ml of a 0.6M solution of lithium triethylborohydride in tetrahydrofuran. After being stirred for 20 minutes, the reaction was quenched by the addition of 50 ml of a 9:1 mixture of water:glacial acetic acid. The reaction was let warm to room temperature then the tetrahydrofuran was removed by rotary evaporation. The aqueous layer was extracted with methylene chloride (3 × 100 ml); the combined organic extracts were dried (anhydrous magnesium sulfate) and concentrated to a white foam. Purification of this crude product by silica gel (1.30 kg of Baker "Analyzed" 60-200 mesh) column chromatography using mixtures of benzene:ethyl acetate as elements (500 ml fractions) afforded after removal of less polar impurities. First the 2-[3α-p-phenylbenzoyloxy-5α-hydroxy-2β-(3α-hydroxy-3-(2-(5,6-dimethoxyindanyl))-trans-1-propen-1-yl)cyclopent-1α-yl]acetic acid, γ-lactone (4j) as a crystalline solid weighing 6.45 g (55.6%) and melting at 154°–156° (from methylene chloride:hexane) and second the 2-[3α-p-phenylbenzoyloxy-5α-hydroxy-2β-(3β-hydroxy-3-(2-(5,6-dimethoxyindanyl))-trans-1-propen-1-yl)cyclopent-1α-yl]acetic acid, γ-lactone (5j) as a viscous oil weighing 3.00 g (25.9%).

The ir spectrum (CHCl$_3$) of the 15α-epimer exhibited absorptions at 1775 cm$^{-1}$ for the lactone carbonyl, at 1710 cm$^{-1}$ for the ester carbonyl, and 970 cm$^{-1}$ for the trans double bond. The ir spectrum (CHCl$_3$) of the 15β-epimer was superimpossible on that of the 15α-epimer.

EXAMPLE 126

2-[3α,5α-Dihydroxy-2β-(3α-hydroxy-3-(2-(5,6-dimethoxyindanyl))-trans-1-propen-1-yl)cyclopent-1α-yl]acetic acid, γ-lactone (6j)

A heterogenous mixture of 4.76 g (8.62 mmole) of 2-[3α-p-phenylbenzoyloxy-5α-hydroxy-2β-(3α-hydroxy-3-(2-(5,6-dimethoxyindanyl))-trans-1-penten-1-yl)cyclopent-1α-yl]acetic acid, γ-lactone (4j), 48 ml of absolute methanol, 40 ml of tetrahydrofuran, and 1.42 g of finely powdered, anhydrous potassium carbonate was stirred at room temperature for 1.5 hour, then cooled to 0°. To the cooled solution was added 21.0 ml of 1.0N aqueous hydrochloric acid. After stirring at 0° for an additional 10 minutes, 90 ml of water was added with concomitant formation of methyl p-phenylbenzoate which was collected by filtration. The filtrate was concentrated by rotary evaporation then was extracted with ethyl acetate (3x), the combined organic extracts were washed with saturated brine, were dried (MgSO$_4$), and were concentrated to give 2.22 g (68.8%) of white, crystalline 2-[3α,5α-dihydroxy-2β-(3α-hydroxy-3-(2-(5,6-dimethoxyindanyl))-trans-1-penten-1-yl)cyclopent-1α-yl]acetic acid, γ-lactone (6j) which melted at 172°–173° after trituration with 50 ml of ether.

The ir spectrum (KBr) exhibited a strong adsorption at 5.57 μ for the lactone carbonyl and a medium adsorption at 10.25 μ for the trans double bond.

EXAMPLE 127

2-[5α-Hydroxy-3α-(tetrahydropyran-2-yloxy)-2β-(3α-tetrahydropyran-2-yloxy]-3-(2-(5,6-dimethoxyindanyl))-trans-1-propen-1-yl)cyclopent-1α-yl]acetic acid, γ-lactone (7j)

To a solution of 2.22 g (5.94 mmole) 2-[3α,5α-dihydroxy-2β-(3α-hydroxy-3-(2-(5,6-dimethoxyindanyl))-trans-1-propen-1-yl)cyclopent-1α-yl]acetic acid, γ-lactone (6j) in 50 ml anhydrous methylene chloride and 2.5 ml of 2,3 dihydropyran at 0° in a dry nitrogen atmosphere was added a few crystals of p-toluenesulfonic acid, monohydrate. After stirring for 20 minutes, the reaction mixture was combined with 100 ml ether, the ether solution washed with saturated sodium bicarbonate (1 × 15 ml) then saturated brine (1 × 15 ml), dried (MgSO$_4$) and concentrated to yield 3.65 g (>100%) crude 2-[5α-hydroxy-3α-(tetrahydropyran-2-yloxy)-2β-(3α[tetrahydropyran-2-yloxy]-3-(2-(5,6-dimethoxyindanyl))-trans-1-propen-1-yl)cyclopent-1α-yl]acetic acid, γ-lactone (7j) which was used without purification.

The ir spectrum (CHCl$_3$) of the product exhibited a strong absorption at 1770 cm$^{-1}$ for the lactone carbonyl and a medium absorption at 970 cm$^{-1}$ for the trans double bond.

EXAMPLE 128

2-[5α-Hydroxy-3α-(tetrahydropyran-2-yloxy)-2β-(3α-[tetrahydropyran-2-yloxy]-3-(2-(5,6-dimethoxyindanyl))-trans-1-propen-1-yl)cyclopent-1α-yl]acetaldehyde, γ-hemiacetal (8j)

A solution of 3.55 g (5.94 mmole) 2-[5α-hydroxy-3α-(tetrahydropyran-2-yloxy)-2β-(3α-[tetrahydropyran-2-yloxy]-3-(2-(5,6-dimethoxyindanyl))-trans-1-propen-1-yl)cyclopent-1α-yl]acetic acid, γ-lactone (7j) in 35 ml dry toluene was cooled to −78° in a dry nitrogen atmosphere. To this cooled solution was added 8.7 ml of 20% diisobutylaluminum hydride in n-hexane (Alfa Inorganics) dropwise at such a rate so that the internal temperature never rose above −65° (15 minutes). After an additional 45 minutes of stirring at −78°, anhydrous methanol was added until gas evolution ceased and the reaction mixture was allowed to warm to room temperature and was concentrated by rotary evaporation. The resultant oil was slurried in methanol then was filtered to remove aluminum salts. Concentration of the filtrate afforded the crude product which was purified by silica gel (Baker "Analyzed" 60–200 mesh) column chromatography using mixtures of benzene:ethyl acetate as elements. After removal of less polar impurities the desired 2-[5α-hydroxy-3α-(tetrahydropyran-2-yloxy)-2β-(3α-[tetrahydropyran-2-yloxy]-3-(2-(5,6-dimethoxyindanyl))-trans-1-propen-1-yl)cyclopent-1α-yl]acetaldehyde, γ-hemiacetal (8j) as a viscous oil weighing 2.69 g (83.3%).

The ir spectrum (CHCl$_3$) of the purified product exhibited a medium absorption at 970 cm$^{-1}$ for the trans double bond and no carbonyl absorption.

EXAMPLE 129

9α-Hydroxy-11α,15α-bis-(tetrahydropyran-2-yloxy)-15-(2-(5,6-dimethoxyindanyl))-cis-5-trans-13-ω-pentanorprostadienoic acid (9j)

To a solution of 4.0 g (9.0 mmole) (4-carbohydroxy-n-butyl)-triphenylphosphonium bromide in a dry nitrogen atmosphere in 8.0 ml dry dimethyl sulfoxide was added 8.97 ml (17.5 mmole) of a 1.95M solution of sodium methylsufinylmethide in dimethyl sulfoxide. To this red ylide solution was added a solution of 1.62 g (3.0 mmole) 2-[5α-hydroxy-3α-(tetrahydropyran-2-yloxy)-2β-(3α-[tetrahydropyran-2-yloxy]-3-(2-(5,6-dimethoxyindanyl))-trans-1-propen-1-yl)cyclopent-1α-yl]acetaldehyde, γ-hemiacetal (8j) in 6.0 ml dry dimethyl sulfoxide. After an additional 30 minutes stirring at room temperature, the reaction mixture was poured onto ice water. The basic aqueous solution was acidified to pH 3 with 10% aqueous hydrochloric acid. The acidic solution was extracted with ethyl acetate (3x) and the combined organic extracts washed with water (2x), dried (MgSO$_4$) and evaporated to an oily residue. The oily product was purified by column chromatography on silica gel (Baker "Analyzed" reagent 60-200 mesh) using mixtures of chloroform:ethyl acetate as eluents. After removal of high R$_f$ impurities, 1.81 g (96.0%) of 9α-hydroxy-11α,15α-bis-(tetrahydropyran-2-yloxy)-15-(2-(5,6-dimethoxyindanyl))-cis-5-trans-13-ω-pentanorprostadienoic acid (9j) was collected.

The ir spectrum (CHCl$_3$) of the purified product exhibited a strong absorption at 1708 cm$^{-1}$ for the acid carbonyl and a medium absorption at 970 cm$^{-1}$ for the trans double bond.

EXAMPLE 130

9α,11α,15α-trihydroxy-15-(2-(5,6-dimethoxyindanyl))-cis-5-trans-13-ω-pentanorprostadienoic acid (12j)

A solution of 720 mg 9α-hydroxy-11α,15α-bis-(tetrahydropyran-2-yloxy)-15-(2-(5,6-dimethoxyindanyl))-cis-5-trans-13-ω-pentanorprostadienoic acid (9j) in 15.0 ml of a 65:35 mixture of glacial acetic acid:water was stirred under nitrogen at room temperature for 18 hours then was concentrated by rotary evaporation. The resultant crude oil was purified by column chromatography on silica gel (Mallinckrodt CC-7 100-200 mesh) using mixtures of chloroform:ethyl acetate as eluents. After elution of less polar impurities the 9α,11α,15α-trihydroxy-15-(2-(5,6-dimethoxyindanyl))-cis-5-trans-13-ω-pentanorprostadienoic acid (12j) was collected as a white solid weighing 410 mg (78.4%) and melting at 90°–93° (from ethyl acetate:hexane).

The ir spectrum (CHCl$_3$) of the product exhibited a strong absorption at 1705 cm$^{-1}$ for the acid carbonyl and a medium absorption at 970 cm$^{-1}$ for the trans double bond.

EXAMPLE 131

9-Oxo-11α,15α-bis-(tetrahydropyran-2-yloxy)-15-(2-(5,6-dimethoxyindanyl))-cis-5-trans-13-ω-pentanorprostadienoic acid (10j)

To a solution cooled to −10° under nitrogen of 1.08 g (1.72 mmole) 9α-hydroxy-11α,15α-bis-(tetrahydropyran-2-yloxy)-15-(2-(5,6-dimethoxyindanyl))-cis-5-trans 13-ω-pentanorprostadienoic acid (9j) in 40 ml reagent grade acetone was added dropwise 0.87 ml of Jones' reagent. After 15 minutes at −10°, 0.87 ml 2-propanol was added and the reaction mixture was allowed to stir an additional 5 minutes at which time it was combined with ethyl acetate, washed with water (2x), dried (MgSO$_4$) and concentrated to give 892 mg (82.6%) of 9-oxo-11α,15α-bis-(tetrahydroyran-2-yloxy)-15-(2-(5,6-dimethoxyindanyl)-cis-5-trans-13-ω-pentanorprostadienoic acid (10j) which was used without purification.

EXAMPLE 132

9-Oxo-11α,15α-dihydroxy-15-(2-(5,6-dimethoxyindanyl))-cis-5-trans-13-ω-pentanorprostadienoic acid (11j):

A solution of 892 mg 9-oxo-11α,15α-bis-(tetrahydropyran-2-yloxy)-15-(2-(5,6-dimethoxyindanyl))-cis-5-trans-13-ω-pentanorprostadienoic acid (10j) in 20 ml of 65:35 mixture of glacial acetic acid:water was stirred under nitrogen at room temperature for 18 hours then was concentrated by rotary evaporation. The resultant crude oil was purified by column chromatography on silica gel (Mallinckrodt CC-4 100–200 mesh) using mixtures of chloroform:ethyl acetate as eluents. After elution of less polar impurities the solid 9-oxo-11α,15α-dihydroxy-15-(2-(5,6-dimethoxyindanyl)-cis-5-trans-13-ω-pentanorprostadienoic acid (11j) was collected weighing 481 mg (74.5%) and melting at 125°–126° (from ethyl acetate: hexane).

The ir spectrum (CHCl$_3$) of the product exhibited strong adsorptions at 1740 cm$^1$ for the ketone carbonyl and 1700 cm$^{-1}$ for the acid carbonyl and a medium absorption at 970 cm$^{-1}$ for the trans double bond.

EXAMPLE 133

N-Methanesulfonyl 9α-hydroxy-11α,15α-bis-(tetrahydropyran-2-yloxy)-15-(2-(5,6-dimethoxyindanyl))-cis-5-trans-13-ω-pentanorprostadienamide (9j)

To a solution of 1.51 g (2.90 mmole) (methanesulfonylamino-carbonyl-n-butyl)triphenylphosphonium bromide in a dry nitrogen atmosphere in 4.0 ml dry dimethyl sulfoxide was added 3.03 ml (5.30 mmole) of a 1.75M solution of sodium methylsufinylmethide in dimethyl sulfoxide. To this red ylide solution was added dropwise a solution of 527 mg (0.97 mmole) 2-[5α-hydroxy-3α-(tetrahydropyran-2-yloxy)-2β-(3α-[tetrahydropyran-2-yloxy]-3-(2-(5,6-dimethoxyindanyl))-trans-1-propen-1-yl)cyclopent-1α-yl] acetaldehyde, γ-hemiacetal (8j) in 4.0 ml dry dimethyl sulfoxide. After an additional 30 minutes stirring at room temperature, the reaction mixture was poured onto ice water. The basic aqueous solution was acidified to pH ∼3 with 10% aqueous hydrochloric acid. The acidic solution was extracted with ethyl acetate (3x) and the combined organic extracts washed once with water (10 ml), dried (MgSO$_4$) and evaporated to a solid residue. This solid residue was triturated with ether and filtered. The filtrate was purified by column chromatography on silica gel (Baker "Analyzed" Reagent 60–200 mesh) using mixtures of chloroform:ethyl acetate as eluents. After removal of high R$_f$ impurities, 259 mg (37.8%) of N-methanesulfonyl 9α-hydroxy-11α,15α-bis-(tetrahydropyran-2-yloxy)-15-(2-(5,6-dimethoxyindanyl))-cis-5-trans-13-ω-pentanorprostadienamide (9j) was collected.

The ir spectrum (CHCl$_3$) of the product exhibited medium aborptions at 1710 cm$^{-1}$ for the carbonyl group and at 970 cm$^{-1}$ for the trans double bond.

EXAMPLE 134

N-Methanesulfonyl 9α,11α,15α-trihydroxy-15-(2-(5,6-dimethoxyindanyl))-cis-5-trans-13-ω-pentanorprostadienamide (12j)

A solution of 259 mg N-methanesulfonyl 9α-hydroxy-11α,15α-bis-(tetrahydroyran-2-yloxy)-15-(2-(5,6-dimethoxyindanyl))-cis-5-trans-13-ω-pentanorprostadienamide (9j) in 10 ml of a 65:35 mixture of glacial acetic acid:water was stirred under nitrogen at room temperature for 18 hours then was concentrated by rotary evaporation. The resultant crude oil was purified by column chromatography on silica gel (Mallinckrodt CC-7 100–200 mesh) using mixtures of chloroform:ethyl acetate as eluents. After elution of less polar impurities the N-methanesulfonyl 9α,11α,15α-trihydroxy-15-(2-(5,6-dimethoxyindanyl))-cis-5-trans-13-ω-pentanorprostadienamide (12j) was collected as a viscous oil weighing 120 mg (61.0%).

The ir spectrum (CHCl$_3$) of the product exhibited a strong absorption at 1705 cm$^{-1}$ for the carbonyl group and a medium absorption at 970 cm$^{-}$ for the trans double bond.

EXAMPLE 135

2-Descarboxy-2-(tetrazol-5-yl)-9α-hydroxy-11α,15α-bis-(tetrahydropyran-2-yloxy)-15-(2-(5,6-dimethoxyindanyl))-cis-5-trans-13-ω-pentanorprostadienoic acid (9j)

To a solution of 1.35 g (2.90 mmole) (4-(tetrazol-5-yl)-n-butyl)triphenylphosphonium bromide in a dry nitrogen atmosphere in 4.0 ml dry dimethyl sulfoxide was added 3.03 ml (5.30 mmole) of a 1.75M solution of sodium methylsulfinylmethide in dimethyl sulfoxide. To this red ylide solution was added dropwise a solution of 527 mg (0.97 mmole) 2-[5α-hydroxy-3α-tetrahydropyran-2-yloxy)-2β-(3α-[tetrahydropyran-2-yloxy]-3-(2-(5,6-dimethoxy indanyl))-trans-1-propen-1-yl)cyclopent-1α-yl) acetaldehyde, γ-hemiacetal (8j) in 4.0 ml dry dimethyl sulfoxide. After an additional 16 hours stirring at room temperature, the reaction mixture was poured onto ice water. The basic aqueous solution was acidified to pH ∼3 with 10% aqueous hydrochloric acid. The acidic solution was extracted with ethyl acetate (3x) and evaporated to a solid residue. This solid residue was triturated with ether and filtered. The filtrate was purified by column chromatography on silica gel (Baker "Analyzed" Reagent 60–200 mesh) using mixtures of chloroform:ethyl acetate as eluents. After removal of high R$_f$ impurities, 343 mg (54.2%) of 2-descarboxy-2-(tetrazol-5-yl)-9α-hydroxy-11α,15α-bis-(tetrahydropyran-2-yloxy)-15-(2-(5,6-dimethoxyindanyl))-cis-5-trans-13-ω-pentanorprostadienoic acid (9j) was collected.

The ir spectrum (CHCl$_3$) of the product exhibited a medium absorption 979 cm$^{-1}$ for the trans double bond.

EXAMPLE 136

2-Descarboxy-2-(tetrazol-5-yl)-9α,11α,15α-trihydroxy-15-(2-(5,6-dimethoxyindanyl))-cis-5-trans-13-ω-pentanorprostadienoic acid (12j)

A solution of 343 mg 2-descarboxy-2-(tetrazol-5-yl)-9α-hydroxy-11α,15α-bis-(tetrahydropyran-2-yloxy)-15-(2-(5,6-dimethoxyindanyl))-cis-5-trans-13-ω-pentanorprostadienoic acid (9j) in 10 ml. of a 65:35 mixture of glacial acetic acid:water was stirred under nitrogen at room temperature for 15 hours then was concentrated by rotary evaporation. The resultant crude oil was purified by column chromatography on silica gel (Mallinckrodt CC-7 100–200 mesh) using mixtures of chloroform:ethyl acetate as eluents. After elution of less polar impurities the 2-descarboxy-2-(tetrazol-5-yl)-9α,11α,15α-dihydroxy-15-(2-(5,6-dimethoxyindanyl)-cis-5-trans-13-ω-pentanorprostadienoic acid (12j) was collected as a foam weighing 124 mg. (48.6%).

The ir spectrum (mull) of the product exhibited a strong absorption at 970 cm$^{-1}$ for the trans double bond.

EXAMPLE 137

5-Indanyl 9α,11α,15α-trihydroxy-15(2-(5,6-dimethoxyindanyl))-cis-5-trans-13-ω-pentanorprostadienoate To a mixture of 92 mg. (0.20 mmole) of 9α,11α,15α-trihydroxy-15-(2-(5,6-dimethoxyindanyl))-cis-5-trans-13-ω-pentanorprostadienoate and 268 mg (2.0 mmoles) of 5-indanol in 9 ml. of dry methylene chloride was added 2.20 ml. of 0.1M solution of dicyclohexylcarbodiimide in methylene chloride. The mixture was stirred for 16 hours at room temperature under nitrogen then was concentrated. Purification of the oily residue by silica gel (Baker "Analyzed" 60–200 mesh) chromatography using mixtures of chloroform:ethyl acetate as eluents provided, after removal of less polar impurities, the 5-indanyl 9α,11α,15α-trihydroxy-15-(2-(5,6-dimethoxyindanyl)-cis-5-trans-13-ω-pentanorprostadienoate weighing 90 mg.

EXAMPLE 138

5-Indanyl 9-oxo-11α,15α-dihydroxy-15-(2-(5,6-dimethoxyindanyl)-cis-5-trans-13-ω-pentanorprostadienoate:

To a mixture of 91 mg. (0.20 mmole) of 9-oxo-11α,15α-dihydroxy-15-(2-(5,6-dimethoxyindanyl))-cis-5-trans-13-ω-pentanorprostadienoate and 268 mg (2.0 mmoles) of 5-indanol in 9 ml. of dry methylene chloride was added 2.20 ml. of 0.1M solution of dicyclohexylcarbodiimide in methylene chloride. The mixture was stirred for 16 hours at room temperature under nitrogen then was concentrated. Purification of the oily residue by silica gel (Baker "Analyzed" 60–200 mesh) chromatography using mixtures of chloroform:ethyl acetate as eluents provided, after removal of less polar impurities, the 5-indanyl 9-oxo-11α,15β-dihydroxy-15-(2-(5,6-dimethoxyindanyl)-cis-5-trans-13-ω-pentanorprostadienoate weighing 90 mg.

EXAMPLE 139

15-(2-indanyl)-ω-pentanorprostaglandin $F_{2\beta}$

To a solution under nitrogen cooled in ice of 100 mg. of 15-(2-indanyl)-ω-pentanorprostaglandin $E_2$ in 10 ml. of absolute methanol is added an ice-cooled solution of 300 mg. of sodium borohydride in methanol. The solution is stirred at 0° for 20 minutes then at room temperature for 1.0 hour. The solution is then quenched by the addition of 2.0 ml. of water and the methanol is removed by rotary evaporation. The resultant aqueous solution is overlaid with ethyl acetate (10 ml.), is acidified by the addition of 10% hydrochloric acid, and is extracted with ethyl acetate (4 × 5 ml.). The combined organic extracts are washed with water (5 ml.) and saturated brine (5 ml.), is dried (anhydrous magnesium sulfate), and is concentrated. Purification of the crude residue by silica gel chromatography using mixtures of methylene chloride:methanol as eluent provides 15-(2-indanyl)-ω-pentanorprostaglandin $F_{2\alpha}$ and 15-(2-indanyl)-ω-pentanorprostaglandin $F_{2\beta}$.

EXAMPLE 140

N-methanesulfonyl 15-(2-indanyl)-ω-pentanorprostaglandin $F_{2\beta}$ carboxamide To a solution under nitrogen cooled in ice of 100 mg. of N-methanesulfonyl 15-(2-indanyl)-ω-pentanorprostaglandin $E_2$ in 10 ml. of absolute methanol is added an ice-cooled solution of 300 mg. of sodium borohydride in methanol. The solution is stirred at 0° for 20 minutes then at room temperature for 1.0 hour. The solution is then quenched by the addition of 2.0 ml. of water and the methanol is removed by rotary evaporation. The resultant aqueous solution is overlaid with ethyl acetate (10 ml.), is acidified by the addition of 10% hydrochloric acid, and is extracted with ethyl acetate (4 × 5 ml.). The combined organic extracts are washed with water (5 ml.) and saturated brine (5 ml.), is dried (anhydrous magnesium sulfate), and is concentrated. Purification of the crude residue by silica gel chromatography using mixtures of methylene chloride:methanol as eluent affords N-methanesulfonyl 15-(2-indanyl)-ω-pentanorprostaglandin $F_{2\alpha}$ carboxamide and N-methanesulfonyl 15-(2-indanyl)-ω-pentanorprostaglandin $F_{2\beta}$ carboxamide.

EXAMPLE 141

2-Descarboxy-2-(tetrazol-5yl)-15-(2-indanyl)-ω-pentanorprostaglandin $F_{2\beta}$ To a solution under nitrogen cooled in ice of 100 mg. of 2-descarboxy-2-(tetrazol-5-yl)-15-(2-indanyl)-ω-pentanorprostaglandin $E_2$ in 10 ml. of absolute methanol is added an ice-cooled solution of 300 mg. of sodium borohydride in methanol. The solution is stirred at 0° for 20 minutes then at room temperature for 1.0 hr. The solution is then quenched by the addition of 2.0 ml. of water and the methanol is removed by rotary evaporation. The resultant aqueous solution is overlaid with ethyl acetate (10 ml.), is acidified by the addition of 10% hydrochloric acid, and is extracted with ethyl acetate (4 × 5 ml.). The combined organic extracts are washed with water (5 ml.) and saturated brine (5 ml.), is dried (anhydrous magnesium sulfate), and is concentrated. Purification of the crude residue by silica gel chromatography using mixtures of methylene chloride:methanol as eluent provides 2-descarboxy-2-(tetrazol-5-yl)-15-(2-indanyl)-ω-pentanorprostaglandin $F_{2\alpha}$ and 2-descarboxy-2-(tetrazol-5-yl)-15-(2-indanyl)-ω-pentanorprostaglandin $F_{2\beta}$.

EXAMPLE 142

15-(2-(1,2,3,4-tetrahydronaphthyl))-ω-pentanor prostaglandin $F_{2\beta}$

To a solution under nitrogen cooled in ice of 100 mg. of 15-(2-(1,2,3,4-tetrahydronaphthyl)-ω-pentanorprostaglandin $E_2$ in 10 ml. of absolute methanol is added an ice-cooled solution of 300 mg. of sodium borohydride in methanol. The solution is stirred at 0° for 20 minutes then at room temperature for 1.0 hour. The solution is then quenched by the addition of 2.0 ml. of water and the methanol is removed by rotary evaporation. The resultant aqueous solution is overlaid with ethyl acetate (10 ml.), is acidified by the addition of 10% hydrochloric acid, and is extracted with ethyl acetate (4 × 5 ml.). The combined organic extracts are washed with water (5 ml.) and saturated brine (5 ml.), is dried (anhydrous magnesium sulfate), and is concentrated. Purification of the crude residue by silica gel chromatography using mixtures of methylene chloride:methanol as eluent affords 15-(2-(1,2,3,4-tetrahydronaphthyl)-ω-pentanorprostaglandin $F_{2\alpha}$ and 15-(2-(1,2,3,4-tetrahydronaphthyl)-ω-pentanorprostaglandin $F_{2\beta}$.

EXAMPLE 143

15-(2-(5,6-dimethoxyindanyl)-ω-pentanorprostaglandin $F_{2\beta}$

To a solution under nitrogen cooled in ice of 100 mg. of 15-(2-(5,6-dimethoxyindanyl))-ω-pentanorprostaglandin $E_2$ in 10 ml. of absolute methanol is added an ice-cooled solution of 300 mg. of sodium borohydride in methanol. The solution is stirred at 0° for 20 minutes then at room temperature for 1.0 hour. The solution is then quenched by the addition of 2.0 ml. of water and the methanol is removed by rotary evaporation. The resultant aqueous solution is overlaid with ethyl acetate (10 ml.), is acidified by the addition of 10% hydrochloric acid, and is extracted with ethyl acetate (4 × 5 ml). The combined organic extracts are washed with water (5 ml.) and saturated brine (5 ml.), is dried (anhydrous magnesium sulfate), and is concentrated. Purification of the crude residue by silica gel chromatography using mixtures of methylene chloride:methanol as eluent affords 15-(2-(5,6-dimethoxyindanyl)-ω-pentanorprostaglandin $F_{2\alpha}$ and 15-(2-(5,6-dimethoxyindanyl))-ω-pentanorprostaglandin $F_{2\beta}$.

EXAMPLE 144

2-[5α-Hydroxy-3α-(tetrahydropyran-2-yloxy)-2β-(3α-(tetrahydropyran-2-yloxy)-3-(2-indanyl)-prop-1-yl)cyclopent-1α-yl]acetic acid, γ-lactone A heterogeneous mixture of 1.56 g. of the 2-[5α-hydroxy-3α-(tetrahydropyran-2-yloxy)-2β-(3α-(tetrahydropyran-2-yloxy)-3-(2-indanyl)-trans-1-propen-1-yl)cyclopent-1α-yl]acetic acid, γ-lactone (7i) prepared above and 156 mg. of 5% palladium on carbon in 15 ml. of absolute methanol is stirred under 1 atmosphere of hydrogen for 2 hours. The reaction mixture is filtered (Celite) and concentrated to provide the 2-[5α-hydroxy-3α-(tetrahydropyran-2-yloxy)2β-(3α-(tetrahydropyran-2-yloxy)-5-(2-indanyl)-prop-1yl) cyclopent-1α-yl]acetic acid, γ-lactone (dihydro 7i).

The product of this reaction may be converted to the 13,14-dihydro-15-(2-indanyl)-ω-pentanorprostaglandins of the A, E and F series of this invention by the procedures of Examples 61–77, 103–110, 140–141, 156–165, and 169–170.

EXAMPLE 145

2-[5α-Hydroxy-3α-(tetrahydropyran-2-yloxy)-2β-(3α-tetrahydropyran-2-yloxy)-4-(2-indanyl)-but-1yl)cyclopent-1α-yl]acetic acid, γ-lactone A heterogeneous mixture of 1.56 g. of the 2-[5α-hydroxy-3α-(tetrahydropyran-2-yloxy)-2β-(3α-(tetrahydropyran-2-yloxy)-4-(2-indanyl)-trans-1-buten-1-yl)cyclopent-1α-yl]acetic acid, γ-lactone (7k) and 156 mg. of 5% palladium on carbon in 15 ml. of absolute methanol is stirred under 1 atmosphere of hydrogen for 2 hours. The reaction mixture is filtered (Celite) and concentrated to provide the 2-[5α-hydroxy-3α-(tetrahydropyran-2-yloxy)-2β-(3α-(tetrahydropyran-2-yloxy)-4-(2-indanyl)-but-1-yl)cyclopent-1α-yl]acetic acid, γ-lactone (dihydro 7K).

The product of this reaction may be converted to the 13,14-dihydro,16-(2-indanyl)-ω-tetranorprostaglandins of the A, E and F series of this invention by the procedures of examples 61–77, 103–110, 140–141, 156–165, and 169–170.

EXAMPLE 146

2-[3α,5α-Dihydroxy-2β-(3α-hydroxy-4-cyclohexylbut-1-yl)cyclopent-1α-yl]acetic acid, γ-lactone A heterogeneous mixture of 2.39 g. 2-[3α,5α-dihydroxy-2β-(3α-hydroxy-4-cyclohexyl-trans-1-buten-1-yl)cyclopent-1α-yl]acetic acid, γ-lactone and 239 mg. of 5% palladium in carbon in 25 ml. of absolute methanol is stirred under 1 atmosphere of hydrogen for 2 hours. The reaction mixture is filtered (Celite) and concentrated to provide 2-[3α,5α-dihydroxy-6β-(3α-hydroxy-4-cyclohexylbut-1-yl) cyclopent-1α-yl]acetic acid, γ-lactone.

This product is transformed into 13,14-dihydro-16-cyclohexyl prostaglandins of the A, E or F series via the procedures of examples 29–43, 103–110, 140–141, 156–165, and 169–170.

EXAMPLE 147

2-[3α,5α-Dihydroxy-2β-(3α-hydroxy-8-cyclopentyloct-1-yl)cyclopent-1α]acetic acid, γ-lactone (241)

A heterogeneous mixture of 2.39 g. 2-[3α,5α-dihydroxy-2β-(3α-hydroxy-8-cyclopentyl-trans-1-octen1-yl)cyclopent-1α-yl]acetic acid, γ-lactone (7l) and 239 mg. of 5% palladium in carbon in 25 ml. of absolute methanol is stirred under 1 atmosphere of hydrogen for 2 hours. The reaction mixture is filtered (Celite) and concentrated to provide 2-[3α,5α-dihydroxy-2β-(3-hydroxy-8-cyclopentyloct1-yl)cyclopent-1α-yl]acetic acid, γ-lactone (24e).

This product is transformed into 13,14 dihydro-20-cyclopentyl prostaglandins of the A, E or F series via the procedures of examples 19–43, 103–110, 140–141, 156–165, and 169–170.

EXAMPLE 148

9α-Hydroxyl-11α,15α-bis-(tetrahydropyran-2-yloxy)-15-cyclodecyl-ω-pentanorprostanoic acid (23m)

A heterogeneous mixture of 1.52 g. of the 9α-hydroxy-11α,15α-bis(tetrahydropyran-2-yloxy)-5-cis-13-trans-15-cyclodecyl-ω-pentanorprostadienoic acid (9m) and 152 mg. of 5% palladium on carbon in 15 ml. of absolute methanol is stirred under 1 atmosphere of hydrogen at 0° for 4 hours. The reaction mixture is filtered (Celite) and concentrated to provide 9α-hydroxy-11α,15α-bis-(tetrahydropyran-2-yloxy)-15-cyclodecyl-ω-pentanorprostanoic acid (23m).

The product is transformed into 15-cyclodecyl-ω-pentanorprostaglandins of the $A_o$, $E_o$, and $F_o$ series via the procedures of examples 65–67 and 77.

EXAMPLE 149

9α-Hydroxy-11α,15α-bis(tetrahydropyran-2-yloxy)-15-(2-(R-1,2,3,4-13-trans-ω-pentanorprostenoic acid (21n)

A heterogeneous mixture of 965 mg. of the 9α-hydroxy-11α,15α-bis(tetrahydropyran-2-yloxy)-15-(2-

(R-1,2,3,4-tetrahydronaphthyl))-5-cis-13-trans-ω-tetranorprostenoic acid (9n) and 96 mg. 5% palladium on carbon in 10 ml. of absolute methanol is stirred under 1 atmosphere of hydrogen at −22° for 5 hours. The mixture is then filtered (Celite) and the filtrate is concentrated to afford 9α-hydroxy-11α,15α-bis-(tetrahydropyran-2-yloxy-15-(2-(R-1,2,3,4-tetrahydronaphthyl))-13-trans-ω-pentanorprostenoic acid (21n).

The product is transformed into 15-(R-1,2,3,4-tetrahydronaphthyl))-ω-pentanorprostaglandins of the $A_1$, $E_1$ and $F_1$ series via the procedures of Examples 65–67 and 77.

EXAMPLE 150

N-methanesulfonyl 9α-Hydroxy-11α,15α-bis-(tetrahydropyran-2-yloxy)-15-(2-indanyl)-13-trans-ω-pentanorprostenamide (21i)

A heterogeneous mixture of 836 mg. of N-methanesulfonyl 9α-hydroxy-11α,15α-bis(tetrahydropyran-2-yloxy)-15-(2-indanyl)-5-cis-13-trans-ω-pentanorprostdienamide (9i) and 84 mg. 5% palladium on carbon in 10 ml. of absolute methanol is stirred under 1 atmosphere of hydrogen at −22° for 5 hours. The mixture is then filtered (Celite) and the filtrate is concentrated to afford N-methanesulfonyl 9α-hydroxy-11α,15α-bis-(tetrahydropyran-2-yloxy)-15-(2-indanyl)-13-trans-ω-pentanorprostenamide (21i).

The product is transformed into N-methanesulfonyl 15-(2-indanyl)-γ-pentanorprostaglandin carboxamides of the $A_1$, $E_1$ and $F_1$ series via the procedures of Examples 65–67 and 77.

EXAMPLE 151

2-Descarboxy-2-(tetrazol-5-yl)-9α-Hydroxy-11α,15α-bis-(tetrahydropyran-2-yloxy)-15-(2-(5,6-dimethoxyindanyl))pentanorprostanoic acid (23i)

A heterogeneous mixture of 1.11 g. of the 2-descarboxy-2-(tetrazol-5-yl)-bis-(tetrahydropyran-2-yloxy)-5-cis-13-trans-15-(2-(5,6-dimethoxyindanyl))-γ-pentanorprostadienoic acid (9i) prepared above and 111 mg. of 5% palladium on carbon in 11 ml. of absolute methanol is stirred under 1 atmosphere of hydrogen at 0° for 4 hours. The reaction mixture is filtered (Celite) and concentrated to provide 2-descarboxy-2-(tetrazol-5-yl)-9α-hydroxy-11α,15α-bis-(tetrahydropyran-2-yloxy)-15-(2-(5,6-dimethoxyindanyl))-γ-pentanorprostanoic acid (23i).

The product is transformed into 2-descarboxy-2-(tetrazol-5-yl)-15-(2-(5,6-dimethoxyindanyl))-ω-pentanorprostaglandins of the $A_o$, $E_o$, and $F_o$ series via the procedures of Examples 65–67 and 77.

EXAMPLE 152

15-(2-indanyl)-ω-pentanorprostaglandin $F_{2\alpha}$

A heterogeneous mixture of 400 mg. (1.0 mmole) of 15-epi-15-(2-indanyl)-ω-pentanorprostaglandin $F_{2\alpha}$ and 4.5 g. of activated maganese dioxide in 45 ml. of dry methylenechloride is stirred overnight at room temperature, filtered, and concentrated to afford 15-keto-15-(2-indanyl-ω-pentanorprostaglandin $F_{2\alpha}$ which is used without purification.

To a solution, cooled in ice, of 200 mg. (0.50 mmole) of 15-keto-15-(2-indanyl)-ω-pentanorprostaglandin $F_{2\alpha}$ in 22 ml. of absolute methanol is added an ice-cooled solution of 669 mg. of sodium brohydride in 85 ml. of absolute methanol. After being stirred for 20 minutes at 0° and 1.0 hour at room temperature, the reaction is quenched by the addition of 6.6 ml. of water. The methanol is removed by rotary evaporation and the resultant aqueous solution is overlaid with ethyl acetate, is acidified with 10% hydrochloric acid, and is further extracted with ethyl acetate. The combined organic extracts are washed with water and with saturated brine, are dried, (anhydrous magnesium sulfate), and are concentrated. Purification of the crude residue by silica gel chromatography affords 15-(2-indanyl)-ω-pentanorprostaglandin $F_{2\alpha}$ and 15-epi-15-(2-indanyl)-ω-pentanorprostaglandin $F_{2\alpha}$.

The other 15 epi prostaglandins of this invention having no lower alkyl group at $C_{15}$ may be similarly converted to their $C_{15}$ epimers by the process above.

EXAMPLE 153

9-oxo-15α-hydroxy-16-cyclohexyl-Δ10,11-5-cis-13-trans-ω-tetranorprostatrienoic acid A solution of 75 mg. of 9-oxo-11α,15α-dihydroxy-16-cyclohexyl)-5-cis-13-trans-ω-tetranorprostadienoic acid (11h), in 15 ml. of acetic acid is stirred at 70° for 18 hours. The reaction mixture is then diluted with xylene and concentrated to afford (after chromatographic purification) 9-oxo-15α-hydroxy-16-(cyclohexyl)-Δ10,11-5-cis-13-trans-ω-tetranorprostatrienoic acid (15h).

EXAMPLE 154

2-Descarboxy-2-(tetrazol-5yl)-9-oxo-15α-hydroxy-16-(2-indanyl)-Δ10,11-5-cis-13-trans-ω-tetranorprostatrienoic acid (15k)

A solution of 75 mg. of 2-descarboxy-2-(tetrazol-5-yl)-9-oxo-11α,15α-dihydroxy-16-(2-indanyl)-5-cis-13-trans-ω-tetranorprostadienoic acid (11k), in 15 ml. of acetic acid is stirred at 70° for 17 hours. The reaction mixture is then diluted with xylene and concentrated to afford (after chromatographic purification) 2 descarboxy-2-(tetrazol-5-yl)-9-oxo-15α-hydroxy-16-(2-indanyl)-Δ10,11-5-cis-13-trans-ω-tetranorprostatrienoic acid (15k).

EXAMPLE 155

9-oxo-11α, 15α-dihydroxy-15β-methyl-16-(2-indanyl)-5-cis-13-trans-ω-tetranorprostadienoic acid (13k)

To a solution of 285 mg. 9α,11α,15α-trihydroxy-16-(2-indanyl)-5-cis-13-trans-ω-tetranorprostadienoic acid (12k) in 15 ml. of dioxane under nitrogen and warmed to 50° is added 220 mg. of 2,3-dichloro-5,6-dicyano-1,4-benzoquinine. The mixture is stirred at 45°–50° overnight under nitrogen, is let cool, and is filtered through Celite. The filtrate is diluted with methylene chloride, is washed with saturated brine, is dried (anhydrous magnesium sulfate), and is concentrated by rotary evaporation. Purification of the crude product by silica gel chromatography affords 9α,11α-dihydroxy-15-oxo-16-(2-indanyl)-5-cis-13-trans-ω-tetranorprostadienoic acid (II).

The above 15-keto-$PGR_{2\alpha}$ compound (561 mg.) is dissolved in dry tetrahydrofuran (50 ml.) and is treated with 1,1,1,3,3,3-hexamethyldisilazane (6ml.) and trimethychlorosilane (1 ml.) at room temperature for 18 hours under nitrogen, then is diluted with xylene. The mixture is filtered, and is concentrated to afford the desired trimethylsilyl derivative of 9α,11α-dihydroxy-15-oxo-16-(2-indanyl)-5-cis-13-trans-ω-tetranorprostadienoic acid.

To a solution of the trimethylsilyl derivative from above (350 mg) in anhydrous ether (35 ml.) is added dropwise 1.5 ml. of a 3M solution of methyl magnesium bromide in ether. The mixture is stirred for 1.0 hour then is quenched by pouring into 100 ml. of saturated aqueous ammonium chloride. The aqueous layer is extracted with ether (2x), and the combined organic extracts is washed with saturated brine, is dried (anhydrous magnesium sulfate), and is concentrated by rotary evaporation. The residue is dissolved in a 65:35 mixture of acetic acid: water. After being stirred for 5 hours at room temperature, the solution is concentrated. Purification of the crude product by column chromatography affords 9α,11α,15β-trihydroxy-15α-methyl-16-(2-indanyl)-5-cis-13-trans-ω-tetranorprostadienoic acid epi III and 9α,11α,15α-trihydroxy-15β-methyl-16-(2-indanyl)-5-cis-13-trans-ω-tetranorprostadienoic acid (III).

A solution cooled to −45° of 143 mg. (0.33 mmole) of the 9α,11α,15α-trihydroxy-15β-methyl-16-(2-indanyl)-5-cis-13-trans-ω-tetranorprostadienoic acid prepared above in 2 ml. of acetone and 128 mg. (0.9 mmole) of trimethylsilyldiethylamine is stirred under nitrogen for 24 hours, then is concentrated. The crude residue is dissolved in 2.0 ml. of dry methylene chloride and 3.5 ml. (0.35 mmole) of a 0.1 0.1M solution of Collin's reagent in methylene chloride is added. The resultant black solution is stirred for 15 minutes at room temperature, then is filtered through a column of silica gel. Concentration of the eluent affords a crude residue which, without purification, is dissolved in 2 ml. of a 65:35 mixture of acetic acid: water. After being stirred for 3 hours at room temperature the solution is concentrated. Purification of the crude residue by column chromatography provides the 9-oxo-11α,15α-dihydroxy-15β-methyl-16-(2-indanyl)-5-cis-13-trans-ω-bisnorprostadienoic acid (13k).

The other 15 lower alkyl prostaglandin analogs of this invention are prepared according to this procedure by the substitution of the desired grignard reagent corresponding to the lower alkyl desired and by the substitution of the appropriate prostaglandin of the F series in the place of 12k.

EXAMPLE 156

N-methanesulfonyl-9-oxo-11α,15α,-dihydroxy-15-(2-indanyl)-13-trans-ω-pentanorprostenamide:

A solution of 86 mg. (0.18 mmole) N-methenesulfonyl-9-oxo-11α,15α-dihydroxy-15-(2-indanyl)-cis-5-trans-13-ω-tetranorprostadienamide (11i) in 6 ml. of anhydrous ether is treated with 448 mg. (3.6 mmole) dimethylisopropyl chlorosilane and 36.0 mg. (3.6 mmoles) triethylamine at room temperature under nitrogen for 48 hours. The reaction mixture is cooled to 0°, methanol is added, and the resulting solution is washed with water, is dried (anhydrous magnesium sulfate), and is concentrated. The residue is dissolved in methanol (6 ml.), 5% palladium on carbon (30 mg.) is added, and the resultant heterogeneous mixture is stirred at −22° under 1 atmosphere of hydrogen for 4 hours. After filtration (Celite) and concentration of the filtrate, the residue is dissolved in a 65:35 mixture of acetic acid:water. The solution is stirred for 10 minutes at room temperature, is then diluted with water, and is extracted with ethyl acetate (4x). The combined organic extracts are washed with brine, are dried (anhydrous magnesium sulfate), and are concentrated to afford, after purification by silica gel chromatography, N-methanesulfonyl 9-oxo-11α,15α-dihydroxy-15-(2-indanyl)-13-trans-ω-tetranorprostenamide.

The other prostaglandin E$_1$ analogs of the present invention are similarly prepared from the corresponding E$_2$ precursors.

EXAMPLE 157

2-Descarboxy-2-(tetrazol-5-yl)-9-oxo-11α,15α-dihydroxy-15-(2-(5,6-dimethoxyindanyl))-13-trans-ω-tetranorprostenoic acid A solution of 88 mg. (0.18 mmole)-2-descarboxy-2-(tetrazol-5-yl)-9-oxo-11α,15α-dihydroxy-15-(2-(5,6-dimethoxyindanyl)-cis-5-trans-13- -tetranorprostadienoic acid (11i) in 6 ml. of anhydrous ether is treated with 448 mg. (3.6 mmole) dimethylisopropyl chlorosilane and 36.0 mg. (3.6 mmoles) triethylamine at room temperature under nitrogen for 48 hours. The reaction mixture is cooled to 0°, methanol is added, and the resulting solution is washed with water, is dried (anhydrous magnesium sulfate), and is concentrated. The residue is dissolved in methanol (6ml.), 5% palladium on carbon (30 mg.) is added, and the resultant heterogeneous mixture is stirred at −22° under 1 atmosphere of hydrogen for 4 hours. After filtration (Celite) and concentration of the filtrate, the residue is dissolved in a 65:35 mixture of acetic acid:water. The solution is stirred for 10 minutes at room temperature, is then diluted with water, and is extracted with ethyl acetate (4x). The combined organic extracts are washed with brine, and dried (anhydrous magnesium sulfate), and are concentrated to afford, after purification by silica gel chromatography, 2-descarboxy-2-(tetrazol-5-yl)-9-oxo-11α,15α-dihydroxy-15-(2-(5,6-dimethoxyindanyl))-13-trans-ω-tetranorprostenoic acid.

The other prostaglandin E$_1$ analogs of the present invention are similarly prepared from the corresponding E$_2$ precursors.

EXAMPLE 158

9α,11α,15α-trihydroxy-15-(1,2,3,4-tetrahydronaphthyl)-13-trans-ω-tetranorprostenoic acid A solution of 75 mg. (0.18 mmole) 9α-11α,15α-trihydroxy-15-(1,2,3,4-tetrahydronaphthyl)-cis-5-trans-13-ω-tetranorprostadienoic acid (11o) in 6 ml. of anhydrous ether is treated with 448 mg. (3.6 mmole) dimethylisopropyl chlorosilane and 36.0 mg. (3.6 mmoles) triethylamine at room temperature under nitrogen for 48 hours. The reaction mixture is cooled to 0°, methanol is added, and the resulting solution is washed with water, is dried (anhydrous magnesium sulfate), and is concentrated. The residue is dissolved in methanol (6 ml. ), 5% palladium on carbon (30 mg.) is added, and the resultant heterogeneous mixture is stirred at −22° under 1 atmosphere of hydrogen for 4 hours. After filtration (Celite) and concentration of the filtrate, the residue is dissolved in a 65:35 mixture of acetic acid:water. The solution is stirred for 10 minutes at room temperature, is then diluted with water, and is extracted with ethyl acetate (4x). The combined organic extracts are washed with brine, are dried (anhydrous magnesium sulfate), and are concentrated to afford, after purification by silica gel chromatography, 9α,11α,15α-dihydroxy-15-(1,2,3,4-tetrahydronaphthyl)-13-trans-ω-tetranorprostenoic acid.

The other prostaglandin $F_{1\alpha}$ analogs of the present invention are similarly prepared from the corresponding $F_{2\alpha}$ precursors.

EXAMPLE 159

N-Acetyl-9-oxo-11α, 15α-dihydroxy-16-cyclohexyl-ω-tetranorprostanamide

A heterogeneous mixture of 147 mg. N-acetyl 9-oxo-11α,15α-dihydroxy-16-cyclohexyl-5-cis-13-trans-ω-tetranorprostadienoic acid (11h) and 15 mg. of 5% palladium on carbon in 15 ml. of absolute methanol is stirred under 1 atmosphere of hydrogen at 0° for 3 hours. The reaction mixture is filtered (Celite) and concentrated. The crude residue is purified by silica gel chromatography to provide N-acetyl-9-oxo-11α,15α-dihydroxy-16-cyclohexyl-ω-tetranorprostanoic acid.

By the above procedure the other prostaglandin analogs of this invention of the $E_2$, $F_{2\alpha}$ or $F_{2\beta}$ type may be converted to the corresponding analog of the "zero" series.

EXAMPLE 160

2-Descarboxy-2-(tetrazol-5-yl)-9-oxo-11α, 15α-dihydroxy-15-cyclodecyl-ω-pentanorprostanoic acid A heterogeneous mixture of 98 mg. 2-descarboxy-2-(tetrazol-5-yl)-9-oxo-11α,15α-dihydroxy-15-cyclodecyl-5-cis-13 trans-ω-pentanorprostadienoic acid (11m) and 10 mg. of 5% palladium on carbon in 10 ml. of absolute methanol is stirred under 1 atomsphere of hydrogen at 0° for 3 hours. The reaction mixture is filtered (Celite) and concentrated. The crude residue is purified by silica gel chromatography to provide 2-descarboxy-2-(tetrazol-5-yl)-9-oxo-11α,15α-dihydroxy-15-cyclodecyl-ω-pentanorprostanoic acid.

By the above procedure the other prostaglandin analogs of this invention of the $E_2$, $F_{2\alpha}$ $F_{2\beta}$ type may be converted to the corresponding analog of the "zero" series.

EXAMPLE 161

N-methanesulfonyl-9α,11α,15α-trihydroxy-16-(2-indanyl)-ω-tetranorprostanoic acid A heterogeneous mixture of 136 mg. N-methanesulfonyl 9α,11α,15α-trihydroxy-16-(2-indanyl)-5-cis-13 trans-ω-tetranorprostadienoic acid (11k) and 14 mg. of 5% palladium on carbon in 14 ml. of absolute methanol is stirred under 1 atmosphere of hydrogen at 0° for 3 hours. The reaction mixture is filtered (Celite) and concentrated. The crude residue is purified by silica gel chromatography to provide N-methanesulfonyl-9α,11α,15α-trihydroxy-16-(2-indanyl)-ω-tetranorprostanoic acid.

By the above procedure the other prostaglandin analogs of this invention of the $E_2$, $F_{2\alpha}$ or $F_{2\beta}$ type may be converted to the corresponding analog of the "zero" series.

EXAMPLE 162

N-Acetyl 9α-hydroxy-11α,15α-bis-(tetrahydropyran-2-yloxy)-15-(2-indanyl)-cis-5-trans-13-ω-pentanorprostadienamide To a solution of 6.78 g. (15.0 mmoles) (acetylaminocarbonyl-n-butyl)triphenylphosphonium bromide in a dry nitrogen atmosphere in dry dimethyl sulfoxide is added 14.5 ml. (29.0 mmole) of a 2. 00M solution of sodium methylsulfinylmethide in dimethyl sulfoxide. To this red ylide solution is added a solution of 735 mg (1.52 mmole) 2-[5α-hydroxy-3α-(tetrahydropyran-2-yloxy)-2β-(3α-[tetrahydropyran-2-yloxy]-3-(2-indanyl)-trans-1-propen-1-yl) cyclopent-1α-yl]acetaldehyde, γ-hemiacetal (8i) in 6.0 ml. dry dimethylsulfoxide. After an additional 1 hour stirring at room temperature, the reaction mixture is poured onto ice water. The basic aqueous solution is acidified to pH~3 with 10% aqueous hydrochloric acid. The acidic solution is extracted with ethyl acetate (3x) and the combined organic extracts washed once with water (10 ml.), dried (MgSO4) and evaporated to a solid residue. The crude product is purified by column chromatography on silica gel (Baker "Analyzed" Reagent 60-200 mesh) using mixtures of chloroform:ethyl acetate as eluents. After removal of high $R_f$ impurities, the acetyl 9α-hydroxy-11α,15α-bis-(tetrahydropyran-2-yloxy)-15-(2-indanyl)-cis-5-trans-13-ω-pentanorprostadienamide (9i) is collected.

EXAMPLE 163

N-Acetyl 9α,11α,15α-trihydroxy-15-(2-indanyl)-cis-5-trans-13-ω-pentanorprostadienamide A solution of 413 mg. N-acetyl 9α-hydroxy-11α,15α-bis-(tetrahydropyran-2-yloxy)-15-(2-indanyl)-cis-5-trans-13-ω-pentanorprostadienamide (9i) in 10 ml. of 65:35 mixture of glacial acetic acid:water is stirred under nitrogen at room temperature for 18 hours then is concentrated by rotary evaporation. The resultant crude oil is purified by column chromatography on silica gel (Mallinckrodt CC7 100-200 mesh) using mixture of chloroform: ethyl acetate as eluents. After elution of less polar impurities the N-acetyl 9α,11α,15α-trihydroxy-15-(2-indanyl)-cis-5-trans-13-ω-pentanorprostadienamide (12i) is collected.

EXAMPLE 164

N-acetyl-9-oxo-11α,15α-bis-(tetrahydropyran-2-yloxy)-15-(2-indanyl)-cis-5-trans-13-ω-pentanorprostadienamide To a solution cooled to −10° under nitrogen of 421 mg. N-acetyl 9α-hydroxy-11α,15α-bis-(tetrahydropyran-2-yloxy)-15-(2-indanyl)-cis-5-trans-13-ω-pentanorprostadienamide (9i) in 15 ml. reagent grade acetone is added dropwise to 0.31 ml. of Jones' reagent. After 15 minutes at −10°, 0.31 ml 2-propanol is added and the reaction mixture is allowed to stir an additional 5 minutes at which time it is combined with ethyl acetate, washed with water (2x), dried (MgSO4) and concentrated to give the N-acetyl 9-oxo-11α,15α-bis-(tetrahydropyran-2-yloxy)-15-(2-indanyl)-cis-5-trans-13-ω-pentanorprostadienamide (10i) which is used without purification.

EXAMPLE 165

N-acetyl-9-oxo-11α,15α-dihydroxy-15-(2-indanyl-cis-5-trans-13-ω-pentanorprostadienamide A solution of 401 mg. N-acetyl 9-oxo-11α,15α-bis-(tetrahydropyran-2-yloxy)-15-(2-indanyl)-cis-5-trans-13-ω-pentanorprostadienamide (10i) in 10 ml. of a 65:35 mixture of glacial acetic acid:water is stirred under nitrogen at room temperature for 16 hours then was concentrated by rotary evaporation. The resultant crude oil is purified by column chromatography on silica gel (Mallinckrodt CC-7 100-200 mesh) using mixtures of chloroform: ethyl acetate as eluents. After elution of less polar impurities the N-acetyl 9-oxo-11α,15α- dihydroxy-15-(2-indanyl)-cis-5-trans-13-ω-pentanorprostadienamide (11i) is collected.

EXAMPLE 166

Dimethyl 2-oxo-2-(2-(1,2,3,4-tetrahydronaphthyl))ethylphosphate (2)

A solution of 49.6 g. (0.40 mole) dimethyl methylphosphonate (Aldrich) in 500 ml. dry tetrahydrofuran is cooled to −78° in a dry nitrogen atmosphere. To the stirred phosphonate solution is added 188 ml. of 2.3M n-butyllithium in hexane solution (Alfa Inorganics, Inc.) dropwise over a period of 40 minutes at such a rate that the reaction temperature never rose above −65°. After an additional 5 minutes stirring at −78°, 38.0 g. (0.20 mole) methyl 1,2,3,4-tetrahydronaphthyl-2-carboxylate is added dropwise at a rate that kept the reaction temperature less than −70° (20 minutes). After 1.0 hours at −78° the reaction mixture is allowed to warm to ambient temperature, neutralized with 25 ml. acetic acid and rotary evaporated to a white gel. The gelatonous material is taken up in 75 ml. water, the aqueous phase extracted with 100 ml. portions of chloroform (3x), the combined organic extracts are backwashed (50 cc $H_2O$), dried ($MgSO_4$), and concentrated (water aspirator) to a crude residue and purified by chromatography, dimethyl 2-oxo-2-(2-(1,2,3,4-tetrahydronaphthyl))ethylphosphonate.

EXAMPLE 167

Dimethyl-2-oxo-2-(2-R-1,2,3,4-tetrahydronaphthyl))ethylphosphonate (2)

A solution of 49.6 g (0.40 mole) dimethyl methylphosphonate (Aldrich) in 500 ml. dry tetrahydrofuran is cooled to −78° in a dry nitrogen atmosphere. To the stirred phosphonate solution is added 188 ml. of 2.3M n-butyllithium in hexane solution (Alfa Inorganics, Inc.) dropwise over a period of 40 minutes at such a rate tht the reaction temperature never rose above −65°. After an additional 5 minutes stirring at −78°, 38.0 g (0.20 mole) methyl R-1,2,3,4-tetrahydronaphthyl-2-carboxylate is added dropwise at a rate that kept the reaction temperature less than −70° (20 minutes). After 1.0 hours at −78° the reaction mixture is allowed to warm to ambient temperature, neutralized with 25 ml. acetic acid and rotary evaporated to a white gel. The gelatonous material is taken up in 75 ml. water, the aqueous phase extracted with 100 ml. portions of chloroform (3x), the combined organic extracts are backwashed (50 cc $H_2O$), dried ($MgSO_4$), and concentrated (water aspirator) to a crude residue and purified by chromatography, dimethyl 2-oxo-2-(2-(R-1,2,3,4-tetrahydronaphthyl))ethylphosphonate (2n).

The products of this reaction is the starting material for the synthesis of 2-(R-1,2,3,4-tetrahydronaphthyl)-ω-pentanorprostaglandins of the A, E or F series via the procedures of Examples 59–84, 103–110, 140–141, 156–165, and 169–170.

EXAMPLE 168

Dimethyl 2-oxo-2-(2-(S-1,2,3,4-tetrahydronaphthyl)ethylphosphonate (2)

A solution of 49.6 g. (0.40 mole) dimethyl methylphosphonate (Aldrich) in 500 ml. dry tetrahydrofuran is cooled to −78° in a dry nitrogen atmosphere. To the stirred phosphonate solution is added 188 ml. of 2.34 M n-butyllithium in hexane solution (Alfa Inorganics, Inc.) dropwise over a period of 40 minutes at such a rate that the reaction temperature never rose above −65°. After an additional 5 minutes stirring at −78°, 38.0 g. (0.20 mole) methyl S-1,2,3,4-tetrahydronaphthyl-2-carboxylate is added dropwise at a rate that kept the reaction temperature less than −70° (20 minutes). After 1.0 hours at −78° the reaction mixture is allowed to warm to ambient temperature, neutralized with 25 ml. acetic acid and rotary evaporated to a white gel. The gelatonous material is taken up in 75 ml. water, the aqueous phase extracted with 100 ml. portions of chloroform (3x), the combined organic extracts are backwashed (50 cc $H_2O$), dried ($MgSO_4$), and concentrated (water aspirator) to a crude residue and purified by chromatography, dimethyl 2-oxo-2-(2-(S-1,2,3,4-tetrahydronaphthyl))ethylphosphonate (2p).

The products of this reaction is the starting material for the synthesis of 15-2(S-1,2,3,4-tetrahydronaphthyl)-ω-pentanorprostaglandins of the A, E, or F series via the procedures of Examples 59–84, 103–110, 140–141, 156–165 and 169–170. Other precursers required for the synthesis of 16 through 20 substituted prostaglandin analogs of the invention are prepared in the same way from the appropriate methyl esters.

EXAMPLE 169

N-Benzoyl 9-oxo-11α,15α-bis-(tetrahydropyran-2-yloxy)-15-(2-5,6-dimethoxyindanyl))-cis-5-trans-13-ω-pentanorprostadienamide (10j)

To a solution of 932 mg (1.49 mmoles) of the 9-oxo-11α,15α-bis-(tetrahydropyran-2-yloxy)-15-(2-(5,6-dimethoxyindanyl))-cis-5-trans-13-ω-pentanorprostadienoic acid (10j) in 25 ml. of dry tetrahydrofuran is added 2.07 ml. of triethylamine. The solution is stirred under nitrogen at ambient temperature for 5 minutes then 1.49 ml. of a 1.0M solution of benzoyl isocyanate in tetrahydrofuran is added. The solution is stirred for 30 minutes, is quenched by the addition of acetic acid, then is concentrated. The crude residue is dissolved in methylene chloride, is washed with water and saturated sodium bicarbonate, is dried (anhydrous magnesium sulfate), and is concentrated to provide the N-benzoyl 9-oxo-11α,15α-bis(tetrahydropyran-2-yloxy)-15-(2-(5,6-dimethoxyindanyl))-cis-5-trans-3-ω-pentanorprostadienamide (10j).

The product is transformed into N-benzoyl 15-(2-(5,6-dimethoxyindanyl))-ω-pentanorprostaglandin $E_2$ carboxamide via the procedures of Example 165.

The other N-substituted prostaglandin carboxamide analogs of the present invention are similarly prepared from the corresponding acid precursors.

EXAMPLE 170

N-methanesulfonyl 9-oxo-11α,15α-bis-(tetrahydropyran-2-yloxy)-15-(2-indanyl)-cis-5-trans-13-ω-pentanorprostadienamide (10i)

To a solution of 566 mg. (1.00 mmole) of the 9-oxo-11α, 15α-bis-(tetrahydropyran-2-yloxy)-15-(2 -indanyl)-cis-5-trans-13-ω-pentanorprostadienoic acid (10l) in 15 ml. of dry tetrahydrofuran is added 1.39 ml. of triethylamine. The solution is stirred under nitrogen at ambient temperature for 5 minutes then 1.00 ml. of a 1.0M solution of N-methanesulfonyl isocyanate in tetrahydrofuran is added. The solution is stirred for 30 minutes, is quenched by the addition of acetic acid, then is concentrated. The crude residue is dissolved in methylene chloride, is washed with water, is dried (anhydrous magnesium sulfate), and is concentrated to afford the N-methane sulfonyl 9-oxo-11α,15α-bis-(tetrahydropyran-2-yloxy)-15-(2-indanyl)-cis-5-trans-13-ω-pentanorprostadienamide (10i).

The product is transformed into N-methanesulfonyl 15-(2-indanyl)-ω-pentanorprostaglandin $E_2$ carboxamide via the procedure of Example 106.

The other N-substituted prostaglandin carboxamide analogs of the present invention are similarly prepared from the corresponding acid precursors.

EXAMPLE 171

9-oxo-11α,15α-bisformyloxy-15-(2 -(R-1,2,3,4-tetrahydronaphthyl))-5-cis-13-trans-ω-pentanorprostadienoic acid To a solution of 41 mg. (0.1 mmole) of 9-oxo-11α,15α-dihydroxy-15-(2-(R-1,2,3,4-tetrahydronaphthyl))-5-cis-13-trans-ω-pentanorprostadienoic acid (11n) in 0.5 ml. of dry tetrahydrofuran is added 29 mg. (0.33 mmole) of formic acetic anhydride and 35 mg. (0.33 mole) of 2,6-lutidine. The solution is stirred for 1 hour under nitrogen at room temperarture then 36 mg. (2.0 mmoles) of water is added. The mixture is stirred at room temperature for an additional 1.0 hour then is diluted with ethyl acetate. The diluted solution is washed with 0.1 N hydrochloric acid (1x), with water (1x), and with saturated brine (1x), is dried (anhydrous magnesium sulfate), and is concentrated. Purification of the crude residue by silica gel chromatography affords the 9-oxo-11α,15α-bisformyloxy-15-(2-(R-1,2,3,4-tetrahydronaphthyl))-5-cis-13-trans-ω-pentanorprostadienoic acid.

EXAMPLE 172

N-methanesulfonyl 9α,11α,15α-Trispivaloyloxy-15-(2-indanyl)-5-cis-13-trans-ω-pentanorprostadienamide:

To a solution of 96 mg. (0.2 mmole) of N-methanesulfonyl of 9α,11α,15α-trihydroxy-15-(2-indanyl)-5-cis-13-trans-ω-tetranorprostadienoic acid (12i) in 1 ml. of pyridine is added 120 mg. (1.0 mmole) of pivaloyl chloride. The solution is stirred for 4 hours at 45° under nitrogen then is cooled to room temperature. To the solution is then added 36 mg. (2.0 moles) of water. The solution is then stirred at room temperature for 2.0 hours, then is diluted with ethyl acetate. The diluted solution is washed with 0.1n hydrochloric acid (2x), with water (1x), and with saturated brine (1x), is dried (anhydrous magnesium sulfate), and is concentrated. Purification of the crude residue by silica gel chromatography provides the N-methanesulfonyl 9α,11α,15α-trispivaloyloxy-15-(2-indanyl)-5-cis-13-trans-ω-pentanorprostadienoic acid.

EXAMPLE 173

9α,11α,15α-Trisbenzoyloxy-16-(2-indanyl)-5-cis-13-trans -ω-tetranorprostadienoic acid To a solution of 82 mg. (0.2 mmole) of 9α,11α,15α-trihydroxy-16-(2-indanyl)-5-cis-13-trans-ω-tetranorprostadienoic acid (12k) in 1 ml. of pyridine is added 140 mg. (1.0 mmole) of benzoyl chloride. The solution is stirred for 4 hours at 45° under nitrogen then is cooled to room temperature. To the solution is then added 36 mg. (2.0 moles) of water. The solution is then stirred at room temperature for 2.0 hours, then is diluted with ethyl acetate. The diluted solution is washed with 0.1 n hydrochloric acid (2x), with water (1x), and with saturated brine (1x), is dried (anhydrous magnesium sulfate), and is concentrated. Purification of the crude residue by silica gel chromatography provides the 9α,11α,15α-trisbenzoyloxy-16-(2-indanyl)-5-cis-13-trans-ω-tetranorprostadienoic acid.

EXAMPLE 174

9α,11α,15α-Trihydroxy-15-(2-5,6-dimethoxyindanyl))-5-cis-13-trans-ω-pentanorprostadienoic acid tris-hydroxymethylaminomethane salt To a solution of 322 mg. (0.70 mmole) of 9α,11α,15α-trihydroxy-14-(2-(5,6-dimethoxyindanyl))-5-cis-13-trans-ω-pentanorprostadienoic acid (12j) in 35 ml. of dry acetonitrile, heated at 80°, is added with vigorous stirring a solution of 86 mg. (0.68 mmole) of tris-hydroxymethylamino methane in 0.15 ml. of water. The mixture is allowed to cool at room temperature and the 9α,11α,15α-trihydroxy-15-(2-(5,6-dimethoxyindanyl))-5-cis-13-trans-ω-pentanorprostadienoic acid tris-hydroxymethylamino methane salt is collected.

EXAMPLE 175

2-descarboxy-2-(tetrazol-5-yl)-9α,11α,15α-Trihydroxy-15-(2-indanyl)-5-cis-13-trans-ω-pentanorprostadienoic acid tris-hydroxymethylamino methane salts To a solution of 297 mg. (0.70 mmole) of 2-descarboxy-2-(tetrazol-5-yl)-trihydroxy-15-(2-indanyl)-5-cis-13-trans-ω-pentanorprostadienoic acid (12i) in 35 ml. of dry acetonitrile, heated at 80°, is added with vigorous stirring a solution of 86 mg. (0.68 mmole) of tris-hydroxymethylamino methane in 0.15 ml. of water. The mixture is allowed to cool at room temperature and the 2-descarboxy-2-(tetrazol-5-yl)-9α,11α,15α-trihydroxy-15-(2-indanyl)-5-cis-13-trans-ω-pentanorprostadienoic acid tris-hydroxymethylamino methane salt is collected.

EXAMPLE 176

Cyclopropyl 9α,11α,15α-trihydroxy-16-(2-indanyl)-5-cis-13-trans-ω-tetranorprostadienoate To a solution of 82 mg. (0.20 mmole) of 9α,11α,15α-trihydroxy-16-(2-indanyl)-5-cis-13-trans-ω-tetranorprostadienoic acid (12k) in 5 ml. of dry methylene chloride is added 22 mg. (0.22 mmole) of triethylamine. The mixture is stirred for 5 minutes then 24 mg. (0.22 mmole) of pivaloyl chloride is added. The solution is stirred for 45 minutes at room temperature under nitrogen then 58 mg. (1.0 mmole) of cyclopropyl alcohol and 150 μ of pyridine are added. The mixture is stirred at room temperature for an additional 2.0 hours then is diluted with ethyl acetate. The diluted solution is washed with water (2x) and saturated brine (1x), is dried (anhydrous magnesium sulfate), and is concentrated. Purification of the crude residue by silica gel chromatography provides the cyclopropyl 9α,11α,15α-trihydroxy-16-(2-indanyl)-5-cis-13-trans-ω-tetranorprostadienoate.

EXAMPLE 177

Dodecyl 9-oxo-11α,15α-dihydroxy-15-(2-(5,6-dimethoxyindanyl))-5-cis-13-trans-ω-pentanorprostadienoate To a solution of 31 mg. of 9α,11α,15α-trihydroxy-15-(2-(5,6-dimethoxyindanyl)-5-cis-13-trans-ω-norprostadienoic acid (10j) in 5 ml. of ether is added a yellow solution of diazododecane (prepared by oxidation of dodecyl hydrazine) dropwise until the yellow color persists for 5 minutes. Concentration of the solution and silica gel chromatographic purification of the crude residue affords dodecyl 9-oxo-11α,15α-dihydroxy-15-(2-(5,6-dimethoxyindanyl))-5-cis-13-trans-ω-norprostadienoate.

EXAMPLE 178

Methyl 9α,11α,15α-trihydroxy-15-(2-(5-1,2,3,4-tetrahydronaphthyl))-5-cis-13-trans-ω-pentanorprostadienoate To a solution of 75 mg. of 9α,11α,15α-trihydroxy-15-(2-(5-1,2,3,4-tetrahydronaphthyl))-5-cis-13-trans-ω-pentanorprostadienoic acid (12p) in 10 ml. of ether is added a yellow solution of diazomethane in ether (prepared from N-methyl-N'-nitro-N-nitrosoguanidine) dropwise until the yellow color persists for 5 minutes. Concentration of the solution and silica gel chromatographic purification of the crude residue affords methyl 9α,11α,15α-trihydroxy-15-(2-(5-1,2,3,4-tetrahydronaphthyl))-5-cis-13-trans-ω-bisnor prostadienoate.

EXAMPLE 179

Cyclooctyl 9-oxo-11α,15α-dihydroxy-15-cyclodecyl-5-cis-13-trans-ω-pentanorprostadienoate To a solution of 121 mg. (0.30 mmole) of 9-oxo-11α,15α-dihydroxy-15-cyclodecyl-5-cis-13-trans-ω-pentanorprostadienoic acid (12m) in 7 ml. of dry methylene chloride is added 33 mg. (0.33 mmole) of triethyl amine. The mixture is stirred for 5 minutes then 36 mg. (0.33 mmole) of pivaloyl chloride is added. The solution is stirred for 45 minutes at room temperature under nitrogen then 192 mg. (1.5 mmole) of cyclooctyl alcohol and 225 μl of pyridine are added. The mixture is stirred at room temperature for an additional 2.0 hours then is diluted with ethyl acetate. The diluted solution is washed with water (2x) and saturated brine (1x), is dried (anhydrous magnesium sulfate), and is concentrated. Purification of the crude residue by silica gel chromatography provides the cyclooctyl 9-oxo-11α,15α-dihydroxy-15-cyclodecyl-5-cis-13-trans-ω-pentanorprostadienoate.

EXAMPLE 180

2-phenylethyl 9α,11α,15α-Trihydroxy-19-cyclopropyl-5-cis-13-trans-ω-norprostadienoate To a solution of 76 mg. (0.21 mmole) of 9α,11α,15α-trihydroxy-19-cyclopropyl-5-cis-13-trans-ω-norprostadienoic acid (12O) and 257 mg. (2.1 mmoles) of 2-phenylethanol in 10 ml. of dry methylene chloride is added 2.5 ml. (0.25 mmole) of a 0.1M solution of dicyclohexylcarbodiimide in methylene chloride. The solution is stirred under nitrogen at room temperature overnight then is concentrated. The crude product is purified by silica gel column chromatography. After removal of the excess 2-phenylethanol with chloroform, elution with ethyl acetate affords the 2-phenylethyl-9α,11α,15α-trihydroxy-19-cyclopropyl-5-cis-13-trans-ω-norprostadienoate.

What is claimed is:

1. A compound of the structure

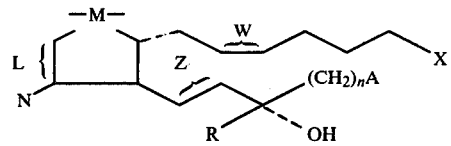

and its $C_{15}$ epimer;

wherein A is 1-adamantyl, 2-norbornyl, 2-(1,2,3,4-tetrahydronaphthyl) wherein said group is racemic or optically active, 2-indanyl or substituted 2-indanyl wherein said substituent is halo, trifluoromethyl, lower alkyl or lower alkoxy;

R is hydrogen or lower alkyl;

n is an integer from 0 to 5;

W and L are each a single bond or cis double bond;

Z is a single bond or trans double bond;

M is keto,

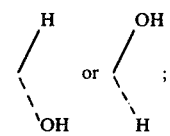

N is hydrogen or α-hydroxyl;

X is

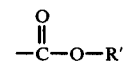

wherein R' is hydrogen, alkyl of from 1 to 10 carbon atoms; aralkyl of from 7 to 9 carbon atoms; cycloalkyl of from 3 to 8 carbon atoms; α- or β-naphthyl; 5-indanyl; phenyl or monosubstituted phenyl, wherein said substituent is halo, lower alkyl, lower alkoxy or phenyl;

and wherein L, M and N are so selected as to complete the structure of the prostaglandin of the A, E or F series.

2. A compound according to claim 1 of the structure:

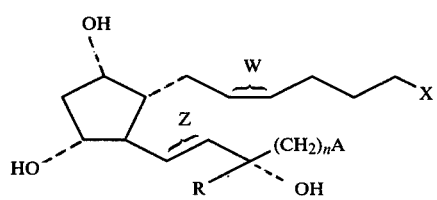

and its $C_{15}$ epimer.

3. The compound of claim 1 wherein M is

L is a single bond, and N is α-hydroxyl.

4. A compound according to claim 1 of the structure:

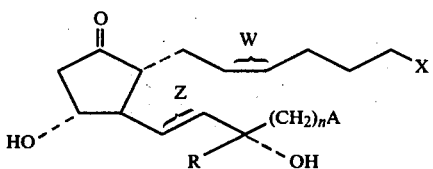

and its C$_{15}$ epimer.

5. A compound according to claim 1 of the structure:

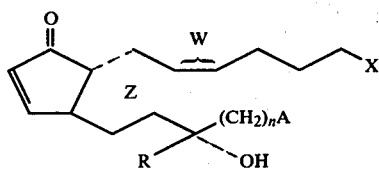

and its C$_{15}$ epimer.

6. A compound of claim 1 wherein n is 0.
7. A compound of claim 1 wherein n is 1.
8. A compound of claim 1 wherein n is 2.
9. A compound of claim 1 wherein n is 3.
10. A compound of claim 1 wherein n is 4.
11. A compound of claim 1 wherein n is 5.
12. A compound of claim 6 wherein said prostaglandin is of the E series.
13. A compound of claim 6 wherein said prostaglandin is of the F series.
14. A compound of claim 7 wherein said prostaglandin is of the E series.
15. A compound of claim 7 wherein said prostaglandin is of the F series.
16. A compound of claim 8 wherein said prostaglandin is of the E series.
17. A compound of claim 8 wherein said prostaglandin is of the F series.
18. A compound of claim 1 wherein A is 2-norbornyl.
19. A compound of claim 1 wherein A is 1-adamantyl.
20. A compound of claim 1 wherein A is 2-indanyl or substituted 2-indanyl wherein said substituent is halo, trifluoromethyl, lower alkyl or lower alkoxyl.
21. A compound of claim 20 wherein A is 2-(5,6-dimethoxy indanyl).
22. A compound of claim 1 wherein W is a cis double bond and Z is a trans double bond.
23. A compound of claim 1 wherein W is a cis double bond and Z is a single bond.
24. A compound of claim 1 wherein W is a single bond and Z is a trans double bond.
25. A compound of claim 1 wherein W is a single bond and Z is a single bond.
26. A compound of claim 12 wherein A is 2-indanyl and the prostaglandin is PGE$_2$.
27. A compound of claim 13 wherein A is 2-indanyl and the prostaglandin is PGF$_{2\alpha}$.
28. A compound of claim 12 wherein A is 2-(5,6,dimethoxy indanyl) and the prostaglandin is PGE$_2$.
29. A compound of claim 13 wherein A is 2-(5,6,dimethoxy indanyl) and the prostaglandin is PGF$_{2\alpha}$.
30. A compound of claim 16 wherein A is 1-adamantyl and the prostaglandins is PGE$_2$.
31. A compound of claim 17 wherein A is 1-adamantyl and the prostaglandin is PGF$_{2\alpha}$.
32. A compound of claim 26 wherein R and R' and each hydrogen.
33. A compound of claim 27 wherein R and R' are each hydrogen.
34. A compound of claim 28 wherein R and R' are each hydrogen.
35. A compound of claim 29 wherein R and R' are each hydrogen.
36. A compound of claim 31 wherein R and R' are each hydrogen.
37. A compound of claim 1 wherein A is 2-[1,2,3,4-tetrahydronaphthyl].
38.

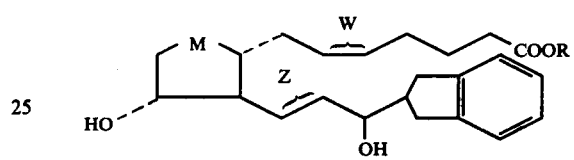

wherein R is hydrogen or CH$_3$, wherein M is keto,

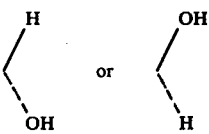

wherein W is a single bond or cis double bond and Z is a single bond or trans double bond.

39. A compound of the formula:

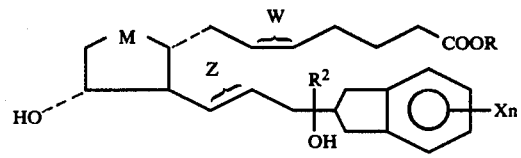

wherein R is hydrogen or alkyl of 1-10 carbon atoms, wherein M is keto,

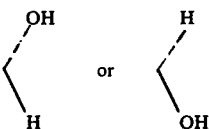

R$_2$ is hydrogen or alkyl of 1-4 carbon atoms, wherein W is a single bond or a cis double bond and Z is a single bond or trans double bond, X is halo, alkyl of 1-4 carbon atoms, alkoxy of 1-4 carbon atoms or trifluoromethyl and n is 0-1.

* * * * *